US012104783B2

(12) United States Patent
Bianchini

(10) Patent No.: US 12,104,783 B2
(45) Date of Patent: Oct. 1, 2024

(54) SMART CANDLE PLATFORM AND SYSTEM

(71) Applicant: LUDELA TECHNOLOGIES LLC, Brea, CA (US)

(72) Inventor: Jamie Bianchini, Minden, NV (US)

(73) Assignee: LUDELA TECHNOLOGIES LLC, Brea, CA (US)

( * ) Notice: Subject to any disclaimer, the term of this patent is extended or adjusted under 35 U.S.C. 154(b) by 343 days.

(21) Appl. No.: 17/615,495

(22) PCT Filed: May 29, 2020

(86) PCT No.: PCT/US2020/035109
§ 371 (c)(1),
(2) Date: Nov. 30, 2021

(87) PCT Pub. No.: WO2020/247254
PCT Pub. Date: Dec. 10, 2020

(65) Prior Publication Data
US 2022/0235929 A1 Jul. 28, 2022

Related U.S. Application Data

(60) Provisional application No. 62/855,918, filed on Jun. 1, 2019.

(51) Int. Cl.
*F21V 37/00* (2006.01)
*A61L 9/03* (2006.01)
(Continued)

(52) U.S. Cl.
CPC .......... *F21V 37/0008* (2013.01); *A61L 9/037* (2013.01); *F21V 23/0471* (2013.01);
(Continued)

(58) Field of Classification Search
CPC . F23Q 25/00; F23N 5/242; F23D 3/16; F21V 23/0471; F21V 37/0008;
(Continued)

(56) References Cited

U.S. PATENT DOCUMENTS 2,696,097 A * 12/1954 Pernici .................... F21V 35/00
431/296
8,337,057 B2 * 12/2012 Chartrand ............... F21V 17/12
362/171
(Continued)

FOREIGN PATENT DOCUMENTS

CN 1782491 A 6/2006
CN 205842651 U 12/2016
(Continued)

OTHER PUBLICATIONS

International Search Report and Written Opinion for International Patent Application No. PCT/US2020/035109, mailed Sep. 15, 2020 (11 pages).
(Continued)

*Primary Examiner* — Vivek K Shirsat
(74) *Attorney, Agent, or Firm* — Perkins Coie LLP

(57) ABSTRACT

A Smart Candle Platform may be configured to produce candle light using a natural wax candle as its fuel source or any other fuel source capable of producing light, including liquid fuels if so configured. The outer shell, inner cover, top cover and base provides a beautiful exterior shell which does not melt but emulates the look of a traditional pillar candle. The outer shell may be changeable/replaceable allowing for style and or seasonal changes. A Smart Candle Platform having multiple interactive systems and sensors for production of natural light via a safe, controllable device which may communicate with other similar configured devices or smart devices having application software embedded therein i.e. a smart phone having an app. is disclosed. The Smart Candle Platform may be configured to allow for auto-extinguishment. The Smart Candle Platform may be configured to allow for the addition of smells or scents.

20 Claims, 95 Drawing Sheets

(51) Int. Cl.
    *F21V 23/04*     (2006.01)
    *F21V 23/06*     (2006.01)
    *F21V 35/00*     (2006.01)
    *F23D 3/16*      (2006.01)
    *F23N 5/24*      (2006.01)
    *F23Q 25/00*     (2006.01)

(52) U.S. Cl.
    CPC .............. *F21V 23/06* (2013.01); *F21V 35/00* (2013.01); *F23D 3/16* (2013.01); *F23N 5/242* (2013.01); *F23Q 25/00* (2013.01); *A61L 2209/12* (2013.01)

(58) Field of Classification Search
    CPC .... F21V 35/00; F21V 35/003; F21V 23/0435; F21V 33/0056; A61L 9/037
    USPC .......................... 431/296, 320, 289, 290, 291
    See application file for complete search history.

(56)  References Cited

U.S. PATENT DOCUMENTS

| | | | |
|---|---|---|---|
| 2003/0086815 A1 | 5/2003 | Wesley | |
| 2008/0129226 A1* | 6/2008 | DeWitt | H05B 47/155 315/307 |
| 2012/0250336 A1 | 10/2012 | Chartrand et al. | |
| 2017/0254532 A1* | 9/2017 | Bauswell | F23D 3/02 |
| 2017/0368219 A1 | 12/2017 | Li | |
| 2019/0293250 A1* | 9/2019 | Angelotti | F21S 10/04 |

FOREIGN PATENT DOCUMENTS

| | | |
|---|---|---|
| CN | 207378729 U | 5/2018 |
| CN | 207438632 U | 6/2018 |
| CN | 109219721 A | 1/2019 |
| EP | 2660510 A1 | 11/2013 |
| JP | S53-098175 A | 8/1978 |
| JP | 2001207938 A | 8/2001 |
| JP | 2005-026047 A | 1/2005 |
| JP | 2015-103481 A | 6/2015 |
| KR | 200270960 Y1 | 4/2002 |

OTHER PUBLICATIONS

Extended European Search Report for European Patent Application No. 20818534.8, mailed Jun. 7, 2023 (6 pages).
Office Action for Chinese Patent Application No. 202080042842.7, mailed Sep. 1, 2023 (18 pages).
Office Action for Japanese Patent Application No. 2021-568795, mailed Apr. 9, 2024 (15 pages).

* cited by examiner

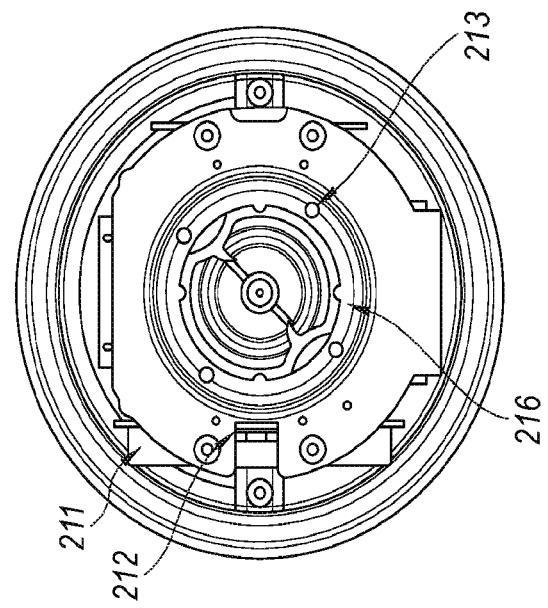
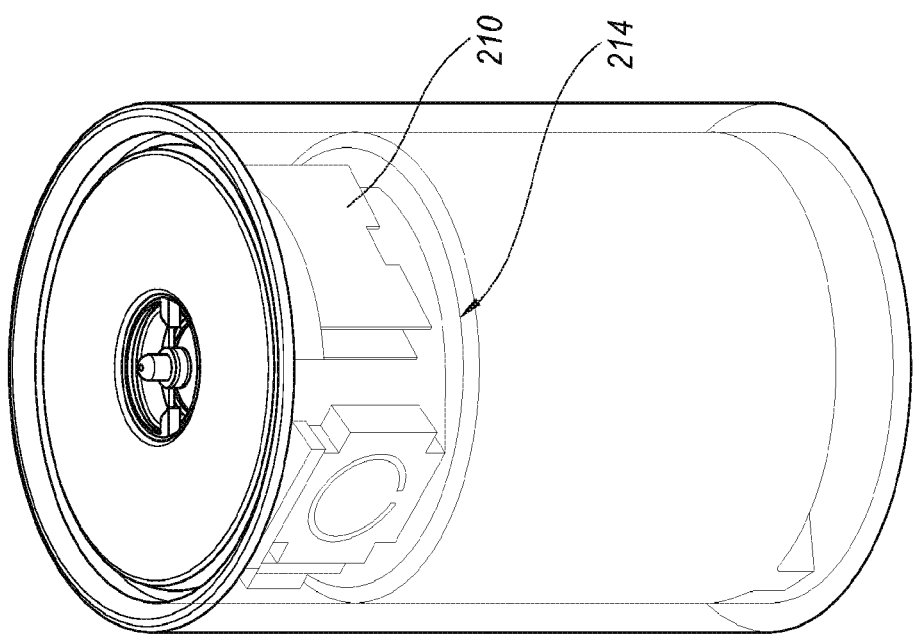
FIG. 36B
FIG. 36A

SMART CANDLE PLATFORM AND SYSTEM

CROSS-REFERENCE TO RELATED APPLICATION(S)

This patent document is a 371 National Phase application of International Patent Application No. PCT/US2020/035109, filed May 29, 2020, which claims the benefit of priority to U.S. Provisional Patent Application No. 62/855,918, filed Jun. 1, 2019. The following patent applications and patents are also incorporated by reference herein in their entireties: U.S. patent application Ser. No. 15/799,249 filed on Oct. 31, 2017 (now U.S. Pat. No. 10,655,843); U.S. patent application Ser. No. 15/452,704 filed Mar. 7, 2017 (now U.S. Pat. No. 9,810,426); U.S. patent application Ser. No. 16/361,187 filed on Mar. 21, 2019 (now U.S. Pat. No. 10,928,059); and U.S. patent Application No. 17/068,516 filed Oct. 12, 2020.

BACKGROUND

As disclosed, the Smart Candle Platform and System is a lighting device and system using natural fuel such as oil or wax providing a structure for an improved lighting experience. In at least one embodiment, the interiorly positioned candle assembly allows for a replaceable outer shell and offers improvements in safety via the spring-loaded bottom feed of the candle assembly. In other embodiments, ignition, control and communication systems may be added to the Smart Candle Platform and System for electrical or electronic control for enhanced safety and enjoyment during operation. Candle light is desirable and consumers enjoy it as a "romantic" or "natural" light source. However, traditional candles and their operation are generally less than desirable because of operating and safety concerns.

The Smart Candle Platform and System as disclosed overcomes many common operating and safety issues of using a living flame "candle", subject to a particular configuration. As is well known, lit candles are a common cause of fires, particularly from accidents involving tipping or falling. For example, when something falls on top of or is too close to the candle flame it can cause a fire. Also, for example, if a candle is not assembled properly then an incidental fire can result and/or accumulation and spillage of hot wax resulting in a mess and annoyance. As is well known, typical candles are manually operated and require direct user contact wherein the user has to go to each candle and light/extinguish it manually and individually. This also limits candle placement options.

SUMMARY

The Smart Candle Platform and System as disclosed contemplates a lighting system providing the beauty and romance of the natural or living flame candle using a frame and structure that allows for use with a multitude of various systems to enhance safety and operation including a plurality of sensors, a control system and a communications system(s) to enhance safety, improve control and generally improve and enhance the user experience while providing an aesthetically pleasing package comparable to a traditional wax pillar candle. In one embodiment, the Smart Candle Platform and System may be configured as a "Simple Candle" using the unique inner frame, top cover, candle assembly (or fuel assembly) and base along with a replaceable cosmetic outer shell for enhanced safety and operation. In one embodiment, a wax overflow trough may be incorporated proximate the top cover aperture. In one embodiment flame position control may be incorporated. The Simple Candle may also incorporate scents via direct injection or via a scent infused ring proximate to the live flame. See FIG. 3E herein illustrating a simplified view of a possible scent ring 47 useful with the present disclosure positioned adjacent to a sensor printed circuit board (PCB) 39 and ignitor ring 36. The Simple Candle may also incorporate the improved safety allowed by a candle or fuel assembly which feeds from the bottom versus the top. The basic structure of the bottom versus the top.

In one embodiment, the Smart Candle Platform and System may also be configured with at least one, if not all of the features of the Simple Candle, and further incorporate at least one of the following additional elements for additional safety to produce a "Safe Candle" having a replaceable outer shell which is safer to operate and implements basic technology which may allow for self-extinguishment during unsafe condition, alone or in combination, including an exhaust fan and/or a pressurized $CO_2$ canister for flame extinguishment. The "Safe Candle" may also incorporate at least one sensor indicating tilt or turnover, an object proximity sensor in relation to the live flame, and at least one sensor indicating continuity failure of the Smart Candle Platform, i.e. dis-engagement of the base from inner sleeve, by way of example, without limitation or restriction. In one embodiment, a microcontroller unit may be implemented to coordinate data collected via the at least one sensor and at least one system for control. The Safe Candle embodiment may include a battery pack or receive power from an external source such as a cigarette lighter or a standard wall plug for use with a home electrical system.

In one embodiment, the Smart Candle Platform and System may also be configured with at least one, if not all of the features of the Simple Candle and the Safe Candle embodiments, and further incorporate at least one of the following additional elements for additional enjoyment to produce a "Smart Candle" configured for communication and control via a smart phone and/or smart phone app.

In one embodiment of the Smart Candle Platform and System, a control system may be added, which may be as simple as an on/off switch, for turning the system on/off. When combined with a smart phone app., this operation may be completed remotely. As will be disclosed herein, in one embodiment, the addition of a tipping/fall sensor (e.g., the one using an accelerometer) triggers (controls) the extinguishing of the flame and prevents the ignitor (burner) from being engaged and may be implemented in some manner or degree with the Simple Candle, the Safe Candle or the Smart Candle, and combinations thereof.

In one embodiment of the Smart Candle Platform and System, the addition of a proximity sensor similarly prevents a flame from being present when something violates the "safe" proximity zone—for example if a curtain is obstructing or contacting the candle shell. In another embodiment of the Smart Candle Platform and System, inclusion of a continuity sensor prevents generation of a flame when the fuel cartridge, the igniter and/or the aperture are not properly assembled or aligned.

In one embodiment, a continuity sensor positioned between the inner sleeve and base prevents generation of a flame if there is improper alignment or dis-engagement between the base and inner sleeve.

In one embodiment of the Smart Candle Platform and System, a fuel level sensor may be incorporated to provide indication to the user of the need to refuel, further, the sensor may be connected to the control system to initiate auto-shutdown in the event of a fuel outage.

In one embodiment of the Smart Candle Platform and System, a flame detection system may be incorporated and may be integrated into a control system to initiate an automatic or semi-automatic shutdown in the event of an unsafe condition, i.e. detection of a flame external to the top cover aperture indicating the potential for ignition external to the live flame.

In one embodiment of the Smart Candle Platform and System, a temperature sensor may be incorporated and may be integrated into a control system to initiate an automatic or semi-automatic shutdown in the event of an unsafe condition, i.e. high temperatures at the top cover indicating the potential for ignition external to the live flame.

In one embodiment of the Smart Candle Platform and System, inclusion of a communication system would allow communication with a remote, computer or smart phone app. wirelessly via sound, voice, Bluetooth, Bluetooth Low Energy, Wi-Fi, RF, cellular and/or other wireless communications methods and/or frequencies, or other existing "smart home standards" networks like i.e. Apple Home Kit, Google/Nest Thread, Zigby, WeMo, Z-wave, alone or in combinations therein to allow infinite user control for flexibility in lighting and extinguishing the smart candle(s) remotely either individually or by groups or zones. As one of ordinary skill will appreciate, this can be done with a single remote control or with a software application on a "smart phone" as an example. The communications can be managed directly via communications and control systems working alone or together to control either an individual smart candle, a group of smart candles communicating between each other or to a single hub and then out to the plurality of smart candles communicating with that hub.

In one embodiment, the Smart Candle Platform and System may also be configured with at least one, if not all, of the features of the embodiments described above, and further incorporate at least one of the following additional features. The Smart Candle Platform and System may include an outer shell having a hollow interior connecting a first opening at an upper end of the outer shell and a second opening at a lower end of the outer shell. The Smart Candle Platform and System may include an inner shell positioned within the hollow interior of the outer shell and having a hollow inner volume. The Smart Candle Platform and System may include a support plate positioned within the hollow inner volume of the inner shell, the support plate having a hollow channel through a mid-section thereof. The Smart Candle Platform and System may include an ignition assembly positioned within the hollow inner volume of the inner shell. The Smart Candle Platform and System may include a fuel source positioned within the hollow inner volume of the inner shell, the fuel source having a cylindrical shape, wherein an upper section of the fuel source has a smaller diameter than a lower section of the fuel source, the fuel source further including a first set of threads thereon for engagement with a corresponding second set of threads of the inner shell so as to allow the fuel source to be secured within the hollow inner volume of the inner shell. The Smart Candle Platform and System may include an ignitor mount positioned within the hollow inner volume of the inner shell, the ignitor mount having a hollow channel through the ignitor mount, and a side wall around the hollow channel through the ignitor mount, wherein the side wall has a groove around the hollow channel through the ignitor mount.

BRIEF DESCRIPTION OF THE DRAWINGS

The accompanying drawings, which are incorporated in and constitute a part of this specification, illustrate embodiments and together with the description, serve to explain and illustrate the principles of the Smart Candle Platform and System (hereinafter referred to simply as the "Smart Candle Platform") as disclosed herein.

FIG. 2B-1 is a bottom view of the base with the base cap removed to illustrate the candle assembly positioned therein.

FIG. 2D-1 is an assembled bottom view of the base and inner cover with the base cap removed.

FIG. 3B-1 is a detailed view of FIG. 3B with the base removed to better illustrate the PCB affixed to the mid-frame and the position of the continuity sensor.

FIG. 3C-1 is a perspective view of the upper portion of the mid-frame with only the fan affixed therein providing a detailed view of the wax collection trough proximate the mid-frame aperture.

FIG. 7A is a top perspective view of the decorative scent pan cover with scent twist adjustment as disclosed while

FIG. 8 is a perspective view of a Smart Candle Platform and System having a scent pan as disclosed wherein

FIG. 8B is a front view of a Smart Candle Platform and System of a decorative scent pan while

FIG. 8F is a bottom perspective view of a scent pan of a Smart Candle Platform and System while

FIG. 9A is a front view of a decorative pan cover of a Smart Candle Platform and System while

FIG. 9B is a top perspective view of a decorative pan cover of a Smart Candle Platform and System while

FIG. 10A is a front view of a molded scent ring of a Smart Candle Platform and System while

FIG. 10B is a top perspective view of a molded scent ring of a Smart Candle Platform and System while

FIG. 11A is a side perspective view of a Smart Candle Platform and System while

FIG. 11C is a front view of a Smart Candle Platform and System of a decorative scent pan while

FIG. 11E is a top perspective view of a scent pan of a Smart Candle Platform and System while

FIG. 12A is a top perspective view of an igniter cover of a Smart Candle Platform and System while

FIG. 12D is a left-side perspective view of an igniter cover of a Smart Candle Platform and System while

FIG. 13A is perspective view of a 2-prong igniter of a Smart Candle Platform and System while FIG. 13B is a front view of a 2-prong igniter of a Smart Candle Platform and System while

FIG. 14A is a top perspective view of an igniter base of a Smart Candle Platform and System while

FIG. 14D is a left-side perspective view of an igniter base of a Smart Candle Platform while

FIG. 20 is a perspective view of a Smart Candle Platform and System providing two different types of cartridges as shown in FIGS. 20A and 20B. FIG. 20A is a perspective view of an extended burn refill bottle while

FIG. 36A is a perspective view of the embodiment of the Smart Candle Platform and System assembly as shown and disclosed herein in FIGS. 33-36 with a clear shell to show the position of the internals.

FIG. 36B is a cut-away top view of the embodiment of the Smart Candle Platform and System assembly as shown and disclosed herein in FIG. 36A.

DETAILED DESCRIPTION

Figure 1:
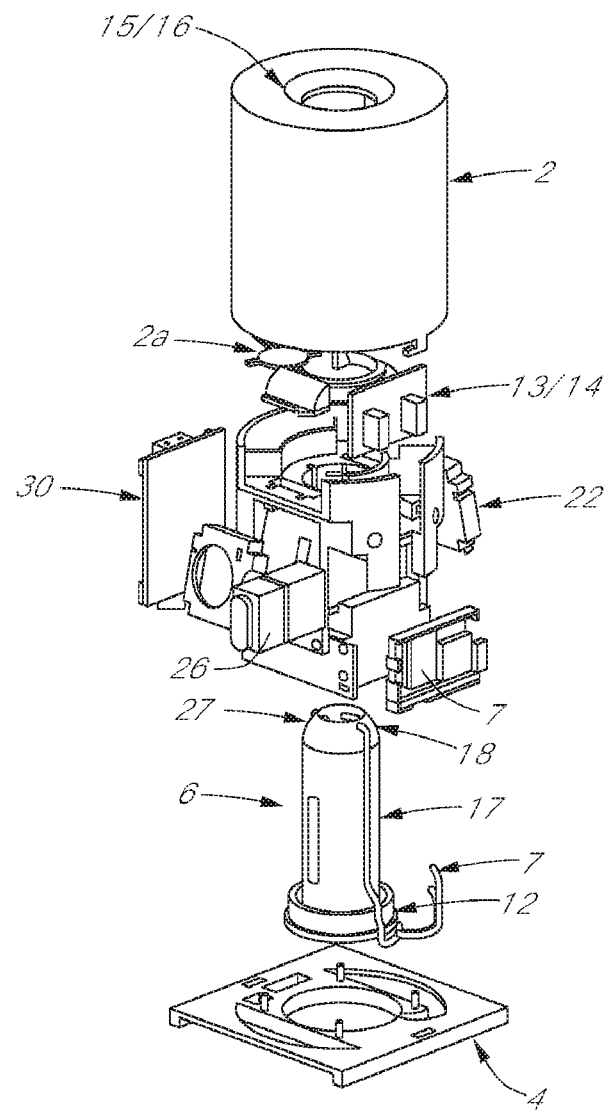
FIG. 1 is an exploded view of an embodiment of the Smart Candle Platform disclosed herein and the various interconnected sub-systems which may comprise the invention.

| Table of Elements | |
|---|---|
| Element Description | Element Number |
| FIGS. | 1-5 |
| Lighting system | 1 |
| Outer shell | 2 |

-continued

Table of Elements

| Element Description | Element Number |
|---|---|
| Opening | 2a |
| Rim | 2b |
| Mid-Frame | 3 |
| Mid-Frame upper annular shelf | 3a |
| Mid-frame lower annular shelf | 3b |
| Mid-frame axial compartment | 3c |
| Mid-frame lower tab | 3d |
| Mid-frame exhaust passage | 3e |
| Mid-frame aperture | 3f |
| Mid-frame opening | 3g |
| Mid-frame securement assembly | 3h |
| Mid-frame notch | 3i |
| Mid-frame base | 3j |
| Base | 4 |
| Base cap | 4a |
| Base ridge | 4b |
| Base shelf | 4c |
| Base - spring mount | 4d |
| Base void | 4e |
| Base - fastener assembly | 4f |
| Base tab | 4g |
| Candle Assembly | 5 |
| Fuel Cartridge | 6 |
| Ignitor (arc) | 7 |
| Fan | 8 |
| On/Off Switch | 9 |
| Smart Candle Platform and System | 10 |
| Sensor system | 11 |
| Continuity sensor | 12 |
| Accelerometer | 13 |
| Gyroscope | 14 |
| Proximity Sensor - magnetic field | 15 |
| Proximity Sensor - visual | 16 |
| Fuel level sensor | 17 |
| Flame sensor | 18 |
|  | 19 |
| Control system | 20 |
| Ignition control system | 21 |
| Ignition control system - electrical leads | 21a |
| Ignitor(s) | 21b |
| Extinguisher system | 22 |
| Infrared (IR) remote control | 23 |
| Timer | 24 |
| Fuel Control System | 25 |
| Power source - battery | 26 |
| Thermo-electric charging (Peltier) | 27 |
| Fuel Feed System | 28 |
| Fuel Storage System | 29 |
| Communications System | 30 |
| Inner cover | 31 |
| Inner cover - main aperture | 31a |
| Inner cover - securement assemblies | 31b |
| Inner cover - shelf | 31c |
| Inner cover - plateau | 31d |
| Top cover | 32 |
| Exhaust duct | 33 |
| Ignitor trough | 34 |
| Ignitor assembly | 35 |
| Ignitor ring | 36 |
| Ignitor channels | 36a |
| Ignitor exhaust aperture | 36b |
| Ignitor mount | 37 |
| Main PCB | 38 |
| Sensor PCB | 39 |
| Feeder tube | 40 |
| Aperture | 40a |
| Channel | 40b |
| Wax candle | 41 |
| Wick | 41a |
| Spring lock (pusher) | 42 |
| Spring | 43 |

-continued

Table of Elements

| Element Description | Element Number |
|---|---|
| Base foot | 44 |
| IR sensor | 45 |
| Thermopile | 46 |
| Scent ring | 47 |
| Restricted access cover (not shown) | 70 |
| Locking tab | 72 |
| Flame | 100 |
| FIGS. | 6-29 |
| Top Cover | 110 |
| Scent pan | 111 |
| Edge | 111a |
| Holder | 112 |
| Scent ring | 113 |
| Scent pan cover | 114 |
| Scent pan cover-with hole | 114a |
| Scent pan cover-without hole | 114b |
|  | 115 |
| Opening | 116 |
| Opening-scent pan cover | 116a |
| Opening-scent pan | 116b |
| Opening-scent ring | 116c |
| Aperture | 117 |
| Aperture-scent pan cover | 117a |
| Aperture-scent pan | 117b |
| Aperture-scent ring | 117c |
|  | 118 |
| Ignition system | 120 |
| Ignition PCB | 121 |
| Ignitor frame | 122 |
| Ignitor top frame | 122a |
| Internal ignition wire routing | 123 |
| Igniter prong | 124 |
| Igniter cover | 125 |
| Igniter base | 126 |
| Igniter finger | 127 |
| Ignitor | 128 |
| Standard igniter assembly | 128a |
| Optional igniter assembly | 128b |
| Igniter wire | 129 |
| Cartridge (fuel source) | 130 |
| Bottle/Container | 131 |
| Extended bottle | 131a |
| Standard bottle | 131b |
| Refill lock | 132 |
| Fuel material (oil, wax, etc.) | 133 |
| Wick | 134 |
| Wick support cap | 134a |
| Release cartridge retention groove | 135 |
| Release cartridge retention | 136 |
| Base | 137 |
|  | 138 |
| Control system | 140 |
| IR remote sensor | 141 |
| Safety tip sensor | 142 |
| Extinguishing fan | 143 |
| Fuel sensor | 144 |
| Tip detection | 145 |
| USB charge port | 146 |
| Wheel | 147 |
| Battery | 148 |
| Push button/Auto extinguish | 149 |
| Shells | 150 |
| Outer shell | 151 |
| Inner cover | 152 |
| Support frame | 152a |
| Protective cover | 152b |
| Shell support | 152c |
| Wax shell support | 153 |
|  | 154 |

-continued

Table of Elements

| Element Description | Element Number |
| --- | --- |
| Injection molded support frame | 155 |
| Push button | 156 |
| Recess storage pocket | 157 |
|  | 158 |
| Push/push cam mechanism | 160 |
| Retention bracket | 161 |
| Fasteners | 162 |
| Push cam | 163 |
| Spring | 164 |
| Push/push spring | 164a |
| Cam wire | 165 |
| Pivoting cam | 166 |
|  | 167 |
|  | 170 |
| Infrared (IR) remote control system | 171 |
| Fuel control system | 172 |
| On/off switch | 173 |
| Ignition control system | 174 |
| Extinguishing system | 175 |
| Fuel storage system | 176 |
| Fuel system | 177 |
| Timer | 178 |
| Password | 179 |
|  | 180 |
| FIGS. | 32-38 |
| Decorative trim plate | 201 |
| Quick igniting wick | 202 |
| High performance igniters | 203 |
| Threaded Refill Bottle | 204 |
| Right-hand Threads | 204a |
| Reverse Threaded Refill Bottle | 205 |
| Reverse Threads | 205a |
| Extinguishing Fan | 206 |
| Ignitor Printed Circuit Board (PCB) | 207 |
| Outer Shell | 208 |
| First Opening of the Outer Shell | 208a |
| Second Opening of the Outer Shell | 208b |
| Inner Shell | 209 |
| Control Printed Circuit Boards (PCBs) | 210 |
| Battery | 211 |
| USB Charging Port | 212 |
| Magnet | 213 |
| Support Plate | 214 |
| Ignitor Mount | 215 |
| Ignition Assembly | 216 |
| Charge Printed Circuit Board (PCB) | 217 |
| Groove | 218 |
| Removable Scent Ring | 219 |
| Optional Scent Pan | 220 |
| Steel Ring for Scent Pan Retention | 221 |
| Space to Accept a Pillar Candle Spike | 222 |
| A Hollow Channel Through the Support Plate | 223 |
| A Hollow Channel Through the Ignitor Mount | 224 |

Before the present Smart Candle Platform is disclosed and described, it is to be understood that the Smart Candle Platform is not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

For the embodiments of the Smart Candle Platform and System 10 shown in FIGS. 1-5, element descriptions and names have been assigned numbers 1-100 as found in the Table of Elements herein. Disclosed are components that can be used with at least one embodiment of the disclosed Smart Candle Platform 10 and one embodiment of a control system 30 which may operate the Smart Candle Platform 10 via a remote control 31. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all potential embodiments of the Smart Candle Platform 10. This applies to all aspects of this application including, but not limited to, components of a Smart Candle Platform 10. Thus, if there are a variety of additional components that can be added it is understood that each of these additional components can be added with any specific embodiment or combination of embodiments of the Candle Platform 10. The present Smart Candle Platform 10 may be understood more readily by reference to the following detailed description of preferred embodiments and the examples included therein and to the Figures and their previous and following description.

In one embodiment, the lighting system of the Smart Candle Platform 10 may be constructed of material of sufficient strength and durability to facilitate low cost production and consumer use for light, decoration and general enjoyment. It is contemplated that the illustrative embodiment shown in the enclosed figures may be constructed of, but not limited to, any metal or combination of metals including bronze, steel and aluminum; plastics or carbon fiber including Kevlar®, foam-blown polyurethane, thermoplastic polyurethane, ethylene vinyl acetate, other polymers, other thermoplastics, carbon rubber, blown rubber polymers, acrylics, composite materials, natural materials (e.g., rubber, leather, etc.), elastomers, combinations thereof, and/or any other material with suitable characteristics (e.g., compressive strength, stability, elasticity, density).

FIG. 1 provides a front perspective view of one illustrative embodiment of the Smart Candle Platform 10 illustrating an exploded view with call-outs to facilitate description of the various interconnected systems which may be implemented in the Smart Candle Platform 10 as disclosed including without limitation or restriction a lighting system 1, a sensing system 11 comprised of at least one condition sensor detecting and receiving input from either the environment or the operation of the Smart Candle Platform 10, a control system 20 and a communications system 30. Illustrative examples could include flame sensing via pyrometer or a thermopile array; flame proximity could be sensed via sensors including an infrared (IR) transmission/receiver type array.

In one embodiment of the Smart Candle Platform 10 as disclosed the lighting system 1 includes an external facade (outer 2) that appears like a typical "dumb" candle and is customizable and may be made of solid wax, which is not used as fuel, plastic, or acrylic or any other material that is suitable and desirable for a particular application. Although shown having a round shape, the outer shell 2 having an opening 2a along its axis (length) therein may have any shape, color, texture and transparency or opacity desirable to consumers and that can be manufactured by those of ordinary skill in the arts. The outer shell 2 could be constructed of any material that allows for transmission or reflection of light and that is sufficient to handle the heat expected during operation of a candle flame including steel, carbon, glass, ceramic, plastic, solid wax, acrylics and or combinations thereof, without limitation and/or restriction. For example, and without limitation or restriction, applicant believes the market desires the outer shell 2 to be manufactured from a wax type material to closely simulate a pillar wax type candle as is well known to one of ordinary skill in the art. The outer shell 2 is mounted to a mid-frame 3 which rests on and is attachable to a base 4. The mid-frame 3 and base 4 could be constructed of any material that is of sufficient strength to support the outer shell 2 and the various sensors and systems contemplated by applicant to be positioned within the outer shell 2, or within close proximity of the outer shell 2 and mid-frame 3, for attachment to the mid-frame 3 therein including various metals, (e.g., steel, aluminum), carbon fiber, plastic and/or combinations thereof, without limitation and/or restriction.

As shown in FIG. 1, the actual fuel for the Smart Candle Platform 10 is supplied via a fuel cartridge 6, positioned on the base 4 within the outer shell 2, and attached to the mid-frame 3. The light and flame are positioned within the opening 2a of outer shell 2, similar to a typical "dumb" solid wax candle well known to those of ordinary skill in the art. As illustrated in FIG. 1, the fuel is typically fed from the bottom such that the lighting system 1 flame (not shown) is generally positioned at the top of the external facade (outer shell 2) of the Smart Candle Platform 10 creating a uniform look and feel for the natural flame candle experience. One of ordinary skill will appreciate that the Smart Candle Platform 10 as disclosed herein may use a wick and solid wax for its fuel in one embodiment. Wax from soy, beeswax, paraffin, soy, palm, essential oils and/or combinations thereof.

One of ordinary skill will also appreciate that the present disclosure may include other types of fuel cartridges 6 which may be used including tanks and gas containers (not shown). Fuel cartridge 6 as disclosed is not limited to a wick and solid wax and that other fuels that may be combusted for production of a pleasant flame and/or odor and may be substituted without limitation including propane, butane, liquid wax, solid wax pellets, and/or natural and man-made oils. The Smart Candle Platform 10 may be configured to produce candle light using a natural wax candle as its fuel source or any other fuel source which is desirable and capable of producing light including wax from soy, beeswax, paraffin, soy, palm, essential oils and/or combinations thereof. The Smart Candle Platform 10 may be configured to produce candle light using a fuel cartridge 6 as shown herein. Liquid fuels (oils) available as fuel may include paraffin, soy, veggie, fatty acid, essential oils and/or combinations thereof. Further, one of ordinary skill will appreciate that the fuel chosen may be odor free or have fragrance added for an enhanced experience, without limitation or restriction. Although not shown, it is contemplated that fragrance could be added to the Smart Candle Platform 10 as disclosed by either addition directly to the fuel or via a separate tank or container type system having its own controls, without limitation or restriction. Although not shown, it is also contemplated that fragrance could be added to the Smart Candle Platform as disclosed via an electrical system that only "heats" or "re-heats" the scented/fragrant oils/materials through a system of electrical resistors vs. combustion. Applicant incorporates by reference herein the following U.S. patents related to fuel control systems and auto-feeding systems as related to candles and lighting systems including: U.S. Pat. Nos. 4,186,430; 6,030,093; 5,722,763; 5,688,040; 5,424,928; 4,566,055; 4,260,365; 4,186,430; 3,867,625; 3,091,106; and 343,461. Applicant incorporates the preceding U.S. Patents for further enablement and description of the present disclosure without admission as to the scope of teaching or the relevance of any particular reference or combinations of references as related to the patentability of the present disclosure.

In this particular embodiment of the Smart Candle Platform 10, a basic control system 20 includes a "hard" on/off switch 9 which could be positioned on the base 4 or the interior or exterior of the outer shell 2 for convenient access with minimal aesthetic distraction. (Not shown) As will be discussed further herein, a proximity sensor (either a magnetic field type 15 and/or a visual type 16) may be positioned proximate the opening 2a and on or within the outer shell 2 to detect whether there is a physical obstruction or barrier from the outside environment, in relation to the Smart Candle Platform 10. As shown, the Smart Candle Platform 10 may be powered internally via a battery 26 that may be mounted to the mid-frame or positioned in the base 4 or within the interior of the shell 2. Although not shown, one of ordinary skill will appreciate that the Smart Candle Platform 10 may be powered externally. In another embodiment, a thermo-electric charging system 27 could be installed alone or in combination with a battery 26, based on Peltier principles, to produce electrical current for use or supplementation of other power sources, using the heat produced by the burning fuel. In other embodiments, power could be provided from an external source including a common electrical outlet or solar power system (not shown), all of which are well known to those of ordinary skill in arts.

The Smart Candle Platform 10 as disclosed has an ignition control system 21 which ignites the fuel delivered via the fuel cartridge 6 through generation of an arc via an ignitor 7, which is well known to one of ordinary skill in the art. In one embodiment of the Smart Candle Platform 10 disclosed, a continuity sensor 12 could be positioned proximate the ignitor 7 and in communication with the control system 20 to monitor the position of the fuel cartridge in the base 4 to ensure proper engagement/contact prior to ignition of the fuel (wick). (Not shown) (See FIGS. 2E-3B and supporting description therein for additional enabling description for this embodiment)

As disclosed and contemplated, in one embodiment, the control system 20 of the Smart Candle Platform 10 may also include a fuel control system 25 connected to a fuel level sensor 17 which could be used to provide an alert to the user that more fuel is needed, per any one of the communication methods described further herein. In other embodiments, and subject to the particular fuel and configuration selected, the fuel level sensor 17 can be connected to an automated fuel feed system 28 (not shown) allowing for the introduction of more fuel from a fuel storage system 29 (not shown) into the fuel cartridge 6. In one embodiment, the fuel level could be sensed via an optical camera system. In another embodiment, the fuel level sensor 17 can signal the fuel control system 25 to auto-feed the wick and/or the wax of the system, subject to the particular fuel and configuration chosen. (See also FIGS. 2E-3B and supporting description therein for additional enabling description for this embodiment)

As disclosed and contemplated, in one embodiment, the control system 20 of the Smart Candle Platform 10 may also include an extinguisher sub-system 22 that could be comprised of an electrically powered fan 8 (electrically connected to a power source—not shown) to "blow out" the flame when the Smart Candle Platform 10 is turned off via the control system 20 or when one of the installed sensors of the sensor system 11 detects a dangerous condition including for example and without limitation the following: an accelerometer 13 and/or gyroscope 14 working alone or in combination has/have detected the Smart Candle Platform 10 has changed position (tipping/tipped over) producing a fire hazard, sending a signal to the control system 20 to activate the fan 8 to "blow out" the flame (burning fuel) re-establishing "safe" conditions to the operation the Smart Candle Platform 10. (See FIGS. 2E-3B and supporting description therein for additional enabling description for this embodiment) Further, although not shown, other types of extinguisher systems 22 are contemplated and would include without restriction or limitation pneumatic piston and bladder combinations that would generate and disperse a blast of air useful in putting out a live flame. Additionally, a mechanical choke, such as butterfly valve, could be positioned proximate the flame and could be engaged for a similar purpose to snuff out the flame by limiting or restricting air to the live flame.

In at least one embodiment of the Smart Candle Platform 10, if any of the sensors (continuity sensor 12, accelerometer 13, gyroscope 14, proximity sensor—magnetic field 15, proximity sensor—visual 16, fuel level sensor 17, flame sensor 18 of the sensor system 11), alone or in combinations, detects a "unsafe" condition or conditions that violate the contemplated controlled operation of the Smart Candle Platform 10, then the control system 20 may initiate extinguishment of the flame via the extinguisher system 22 (via exhaust duct 33 and fan 8 as discussed at FIGS. 2-3) and/or the ignition system 21 by removing fuel from the flame and/or disabling the ignitor 7, to disable operation of the Smart Candle Platform 10. (See FIGS. 2E-3 and supporting description therein for additional enabling description for this embodiment)

As disclosed and contemplated, in another embodiment, the Smart Candle Platform 10 would have at least one control system 20, which could be an infrared (IR) remote control type 23 working within line-of-sight of the Smart Candle Platform 10. As disclosed, the remote control 23 would control the on/off switch 9 (not shown) mounted on the Smart Candle Platform 10 which may also control (trigger) the ignitor 7 of the ignition control system 21 and the fan 8 of the extinguisher system 22 deployed in the Smart Candle Platform 10. As disclosed and contemplated, in another embodiment, the Smart Candle Platform 10 would have at least one control system 20, which could be a timer system 24 which could work with the ignition system 21 and extinguisher control system 22 of the Smart Candle Platform 10. As disclosed, the timer 24 would also control the on/off switch 9 (not shown) mounted on the Smart Candle Platform 10 which may also control (trigger) the ignitor 7 of the ignition control system 21 and the fan 8 of the extinguisher system 22 deployed in the Smart Candle Platform 10, on either a pre-programmed time period (e.g., 1 h, 2 h and/or 4 h) or a variable period time to be selected by the user (e.g., 59 minutes). Upon expiration of the selected time period, the Smart Candle Platform 10 would shut down automatically.

The Smart Candle Platform 10 disclosed and claimed herein may be configured with a communication system 30 including appropriate transmitters and receivers, subject to the particular communication installed therein. The communication system 30 may allow communication and control between individual Smart Candle Platforms 10 and a smart phone (not shown) having a software application installed therein via communication with WiFi, Bluetooth, cellular and/or audio type systems and combinations thereof. The communication system 30 may also be configured to allow communication between groups of Smart Candle Platforms 10 allowing multi-device and zone type control via the various types of communication systems that may be installed therein.

The following modifications, although not shown, would be obvious to one of ordinary skill in the art in view of the present disclosure. The various elements of the Smart Candle Platform 10 may be separately formed and later engaged with one another (e.g., via mechanical fasteners, material fusing, chemical adhesives, etc.) or integrally formed. The materials used to construct the Smart Candle Platform 10 and various elements thereof will vary depending on the specific application of the Smart Candle Platform 10, but it is contemplated that steel, aluminum, polymers, other synthetic materials, natural materials, and/or combinations thereof will be especially useful for some applications. Accordingly, the above-referenced elements may be constructed of any material known to those skilled in the art or later developed, which material is appropriate for the specific application of the Smart Candle Platform 10, without departing from the spirit and scope of the Smart Candle Platform 10 as disclosed and claimed herein.

Figure 2:
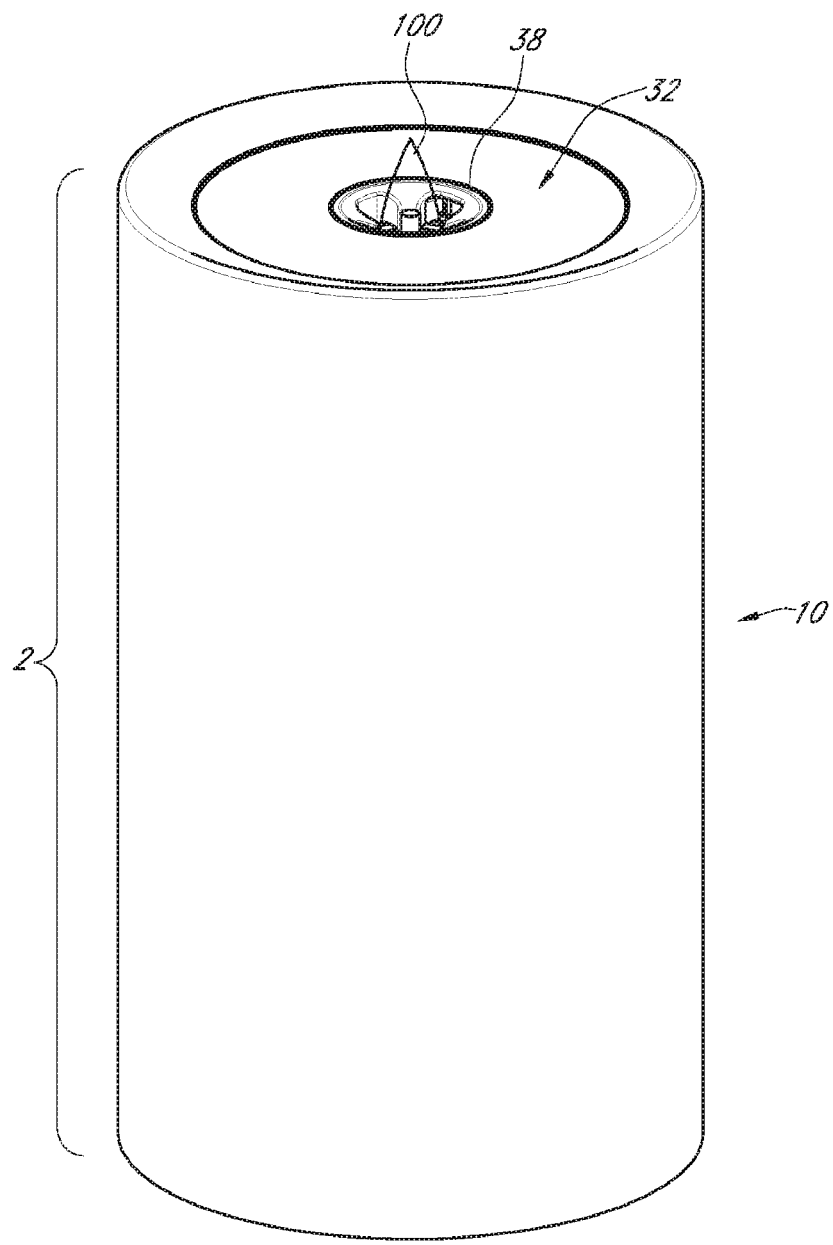
FIG. 2 is a perspective of the exterior portion of one embodiment of the Smart Candle Platform as disclosed herein during operation.

In another embodiment of the Smart Candle Platform 10 as disclosed and shown throughout FIGS. 2-3 includes an external facade (outer shell 2) that appears like a typical "dumb" candle and is customizable. Although shown having a round shape, the outer shell 2 having opening 2a therein may have any shape, color, texture and transparency or opacity desirable to consumers and that can be manufactured by those of ordinary skill in the arts that allows for transmission or reflection of all or portions of the electromagnetic spectrum or selected portions of the electromagnetic spectrum to enable a sensor(s), as disclosed or in use, that is sufficient to handle the heat expected during operation of a candle flame including steel, carbon, glass, ceramic, plastic and/or combinations thereof, without limitation and/or restriction. The outer shell 2 could also be constructed of any material that is pleasing to a user and may be constructed of plastic or wax to emulate a pillar candle. The outer shell can be constructed to be removable and/or replaceable so that the user may switch the outer shells to better match their décor or holiday themes—red or green for Christmas and black or orange for Halloween or Fall by way of example and without limitation.

Figure 2A:
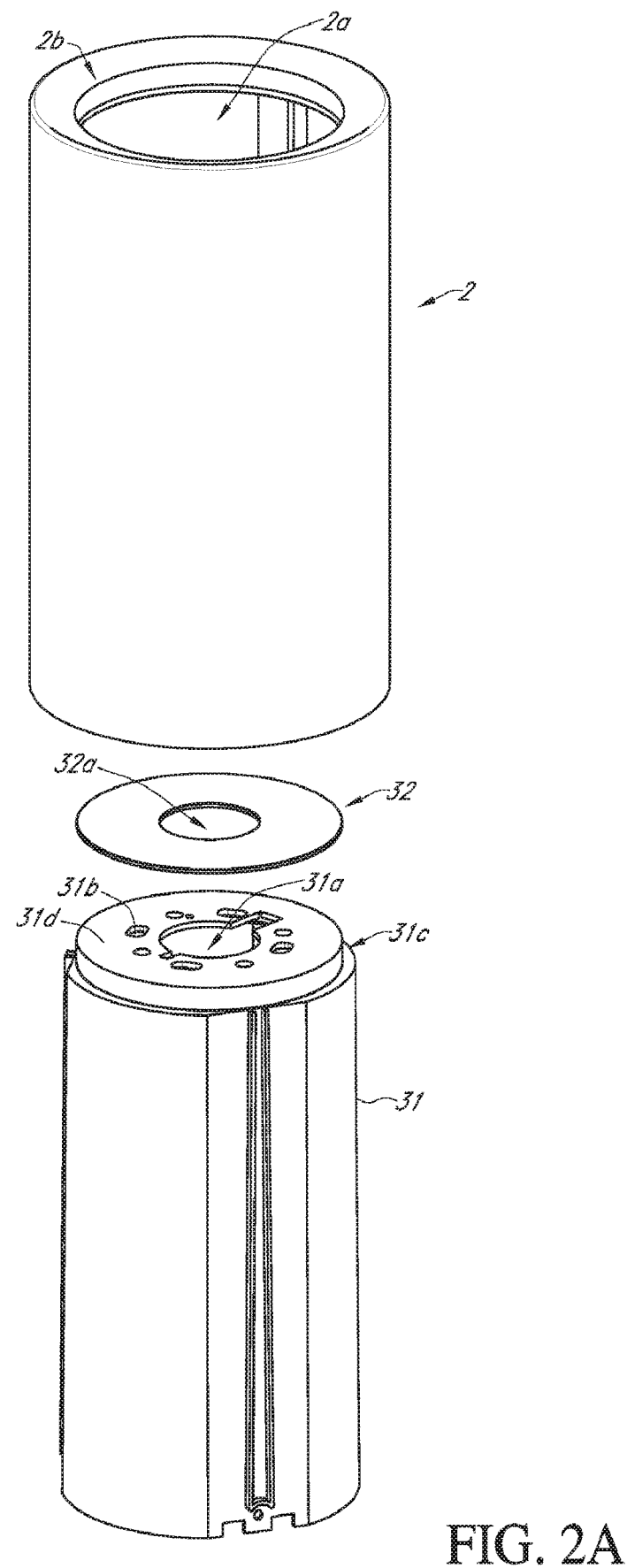
FIG. 2A is an exploded view of the Smart Candle Platform of FIG. 2 providing further construction and assembly details for the outer shell, top cover and inner cover.

FIG. 2 is a perspective of the exterior portion of another embodiment of the Smart Candle Platform 10 as disclosed herein during operation. As shown, the Smart Candle Platform 10 has a live flame 100 positioned with discharge from an ignitor ring 36 surrounded by a top cover 32 positioned in the upper portion of the outer shell 2. In this particular embodiment of a Smart Candle Platform 10, a candle 41 composed of wax having a wick 41a is the fuel and may have all attributes previously attributed and discussed regarding FIG. 1. One of ordinary skill will appreciate that scented operation could be added to the Smart Candle Platform 10 via scents in candle 41. (See infra) FIG. 2A is an exploded view of the Smart Candle Platform of FIG. 2 providing further construction and fabrication details. As shown in FIG. 2, the Smart Candle Platform 10 may be fabricated with an outer shell 2 having an opening 2a therein. An inner cover 31, also having a main aperture 31a is shown positioned within and enclosed by outer shell 2 with the top cover 32 positioned upon the upper portion of the inner cover 31. As shown, the outer shell 2 has a hollow interior connecting an upper end and a lower end with a rim 2b positioned around the interior of the upper end, together forming a first opening 2a. An inner cover 31 having a hollow interior connecting an upper end and an open lower end is shown with a generally flat plateau at the upper end 31d formed by shelf 31c. A main aperture 31a is formed therein. The inner cover 31 is positioned within the first opening of the outer shell 2a. One of ordinary skill will appreciate that other embodiments of outer shell 2 and inner sleeve 31 may be constructed without rim 2b, plateau 31d and shelf 31c without restriction or limitation as required for a particular configuration or application. One of ordinary skill will note that various smaller apertures 31b for securement of assemblies are positioned proximate and around the main aperture 31a which when assembled are also proximate to and positioned around the opening 2a of the outer shell 2. Top cover 32 is non-conductive and acts as an insulator between inner cover 31 and outer shell 2. Top cover aperture 32a, first opening 2a, and main aperture 31a align. Further, top cover 32 may be aesthetically pleasing and may be light reflective in support of wick 41a and flame 100 during operation. One of ordinary skill will appreciate that although top cover 32 is disclosed and described as being composed of glass, any material suitable for the particular application of a Smart Candle Platform 10 may be chosen including wax, plastic, ceramics as well as various metals including steel, aluminum or bronze and/or various combinations thereof which may be reflective or optically transparent, as required by a particular application. Further, top cover 32 may be configured to have an outer surface similar to outer shell 2 which may also be wax, having heat resistant properties as required by its proximity to the live flame.

Figure 2B:
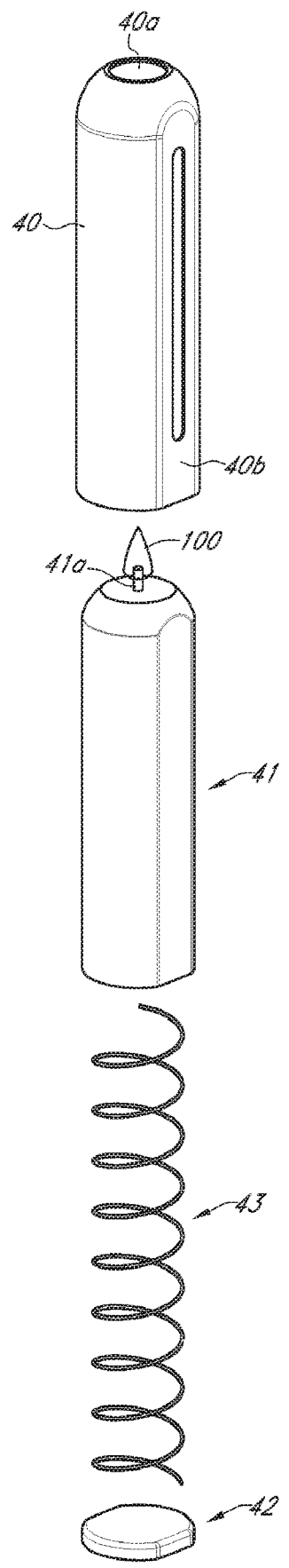
FIG. 2B is another exploded view of the Smart Candle Platform of FIG. 2 providing further construction and assembly details for the feeder tube, candle, spring and spring lock.
Figures 1, 2B:
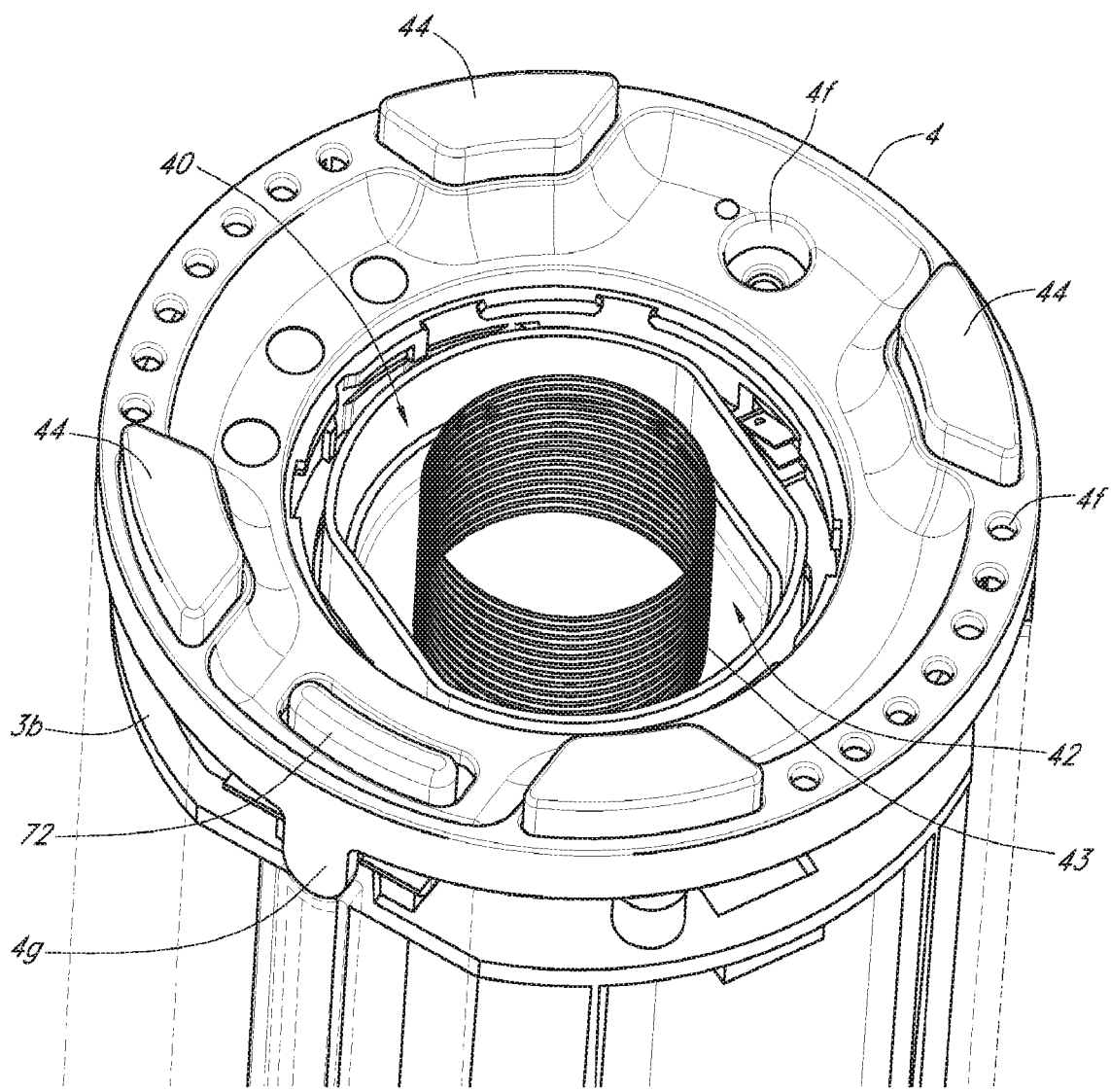

Exploded view FIG. 2B of the Smart Candle Platform illustrates one embodiment of a fuel (wax) and fuel feed system 28 shown as a candle assembly 5. As shown in this embodiment, the candle assembly 5 is a feeder tube 40 configured to be positioned in the aperture of the inner cover sleeve 31a, a wax candle 41 with wick 41a, spring 43 and candle pusher 42. One embodiment of the Smart Candle Platform 10 disclosed herein may be configured based on FIGS. 2A and 2B wherein outer shell 2, top cover 32 and inner cover 31 (also referred to as "inner sleeve 31") having main aperture 31a therein, with candle assembly 5 positioned internally therein, upon engagement between base 4 and inner cover 31 forms a simple embodiment of a working live flame Smart Candle Platform 10. FIG. 2B-1 is a bottom view of the base 4 with the base cap 4a removed to illustrate the candle assembly 5 (feeder tube 40, candle 41, candle pusher 42 and spring 43) positioned therein with mid-frame 3. As shown, base 4 may be configured with a plurality of base feet 44. As shown, base 4 may also have base tabs 4g positioned around the perimeter of the base 4 for coupled engagement with recesses 31e positioned around the perimeter of inner cover 31 or for coupled engagement with recesses positioned in the lower portion of the mid-frame 3. One of ordinary skill will appreciate that other configurations for locked engagement may be used without departure from the spirit and intent of the disclosure.

Figure 2C:
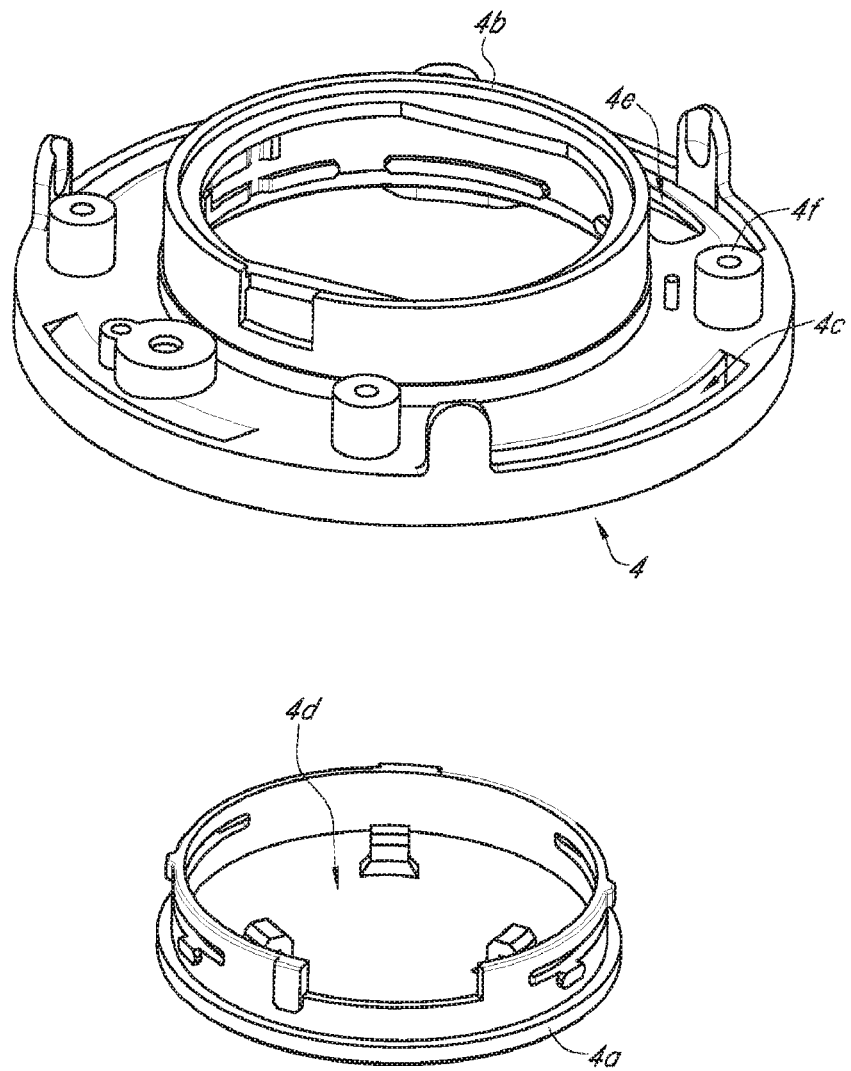
FIG. 2C is an exploded view of the Smart Candle Platform of FIG. 2 and particularly the base and base cap.

Further, as configured, the wax candle 41 is meant to advance automatically or semi-automatically via candle pusher 42 positioned against the bottom of wax candle 41 and is in communication with spring 43 which is positioned interior of base cap 4a of base 4 as shown in further detail in FIG. 2C. As shown, base 4 and base cap 4a work together with the lower end of inner cover 31 to operate as a wax lock during operation of the Smart Candle Platform 10. Although not shown, one of ordinary skill will appreciate that the base 4 and base cap 4a may work together with the lower end of inner cover 31 to contain a fuel refill and/or cartridge in other embodiments configured for a fuel cartridge 6 which could be configured for use of liquid fuel—such as soy oil. One of ordinary skill will appreciate that the upper end portion of the spring 43 make work directly against wax candle 41 without spring lock (pusher) 42 without departure from the spirit and intent of the present disclosure. Although not shown, one of ordinary skill will appreciate that a canister having a size and shape similar to the feeder tube configured with a wick 41a distending from an aperture positioned in the upper portion of the canister, wherein in the upper portion is a removable lid, could be one embodiment of fuel cartridge 6 useful for liquid fuel.

Figure 2D:
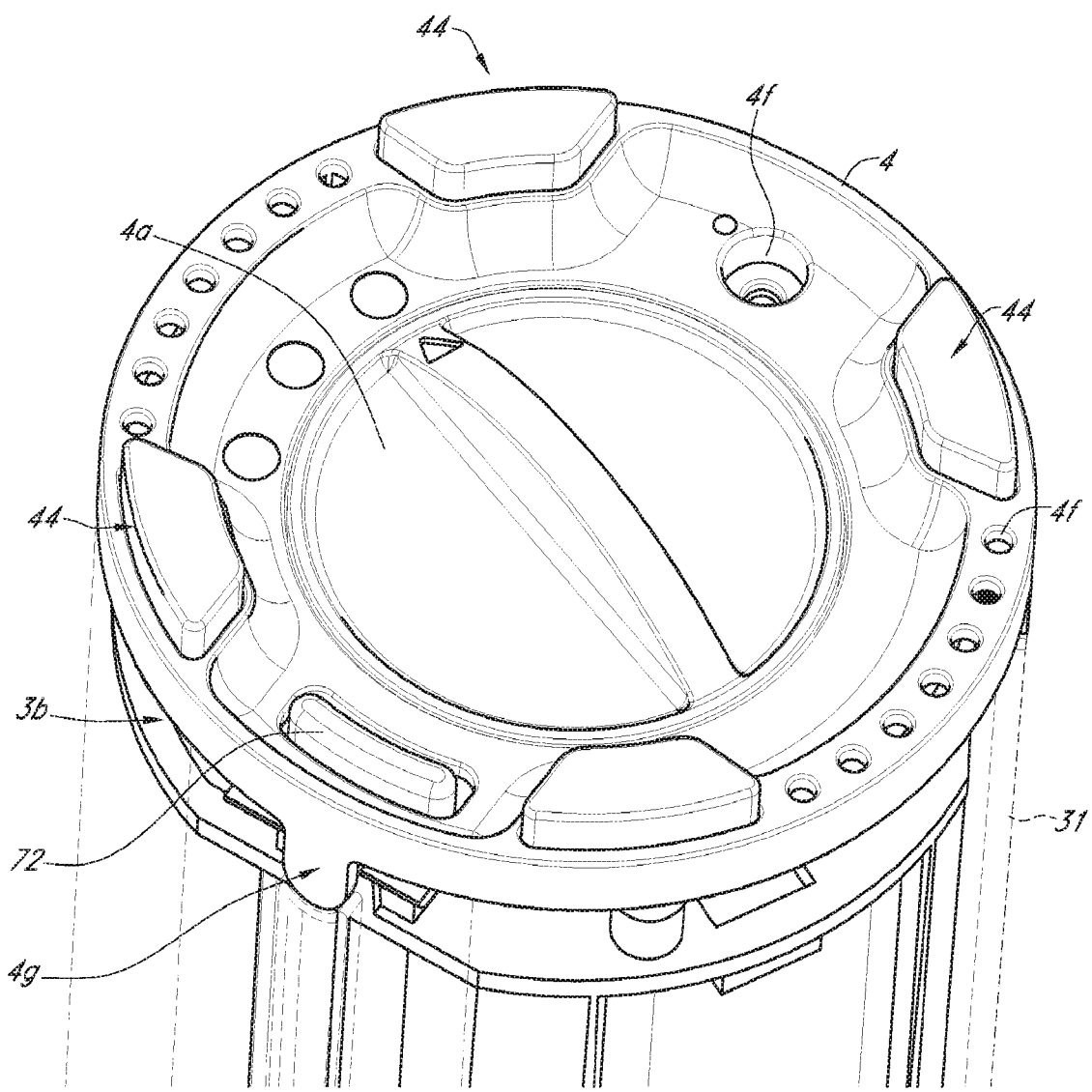
FIG. 2D is an assembled view of the Smart Candle Platform of FIG. 2 providing further construction and assembly details for the affixation of the lower portion of the inner cover to the base, base feet and base cap.
Figures 1, 2D:
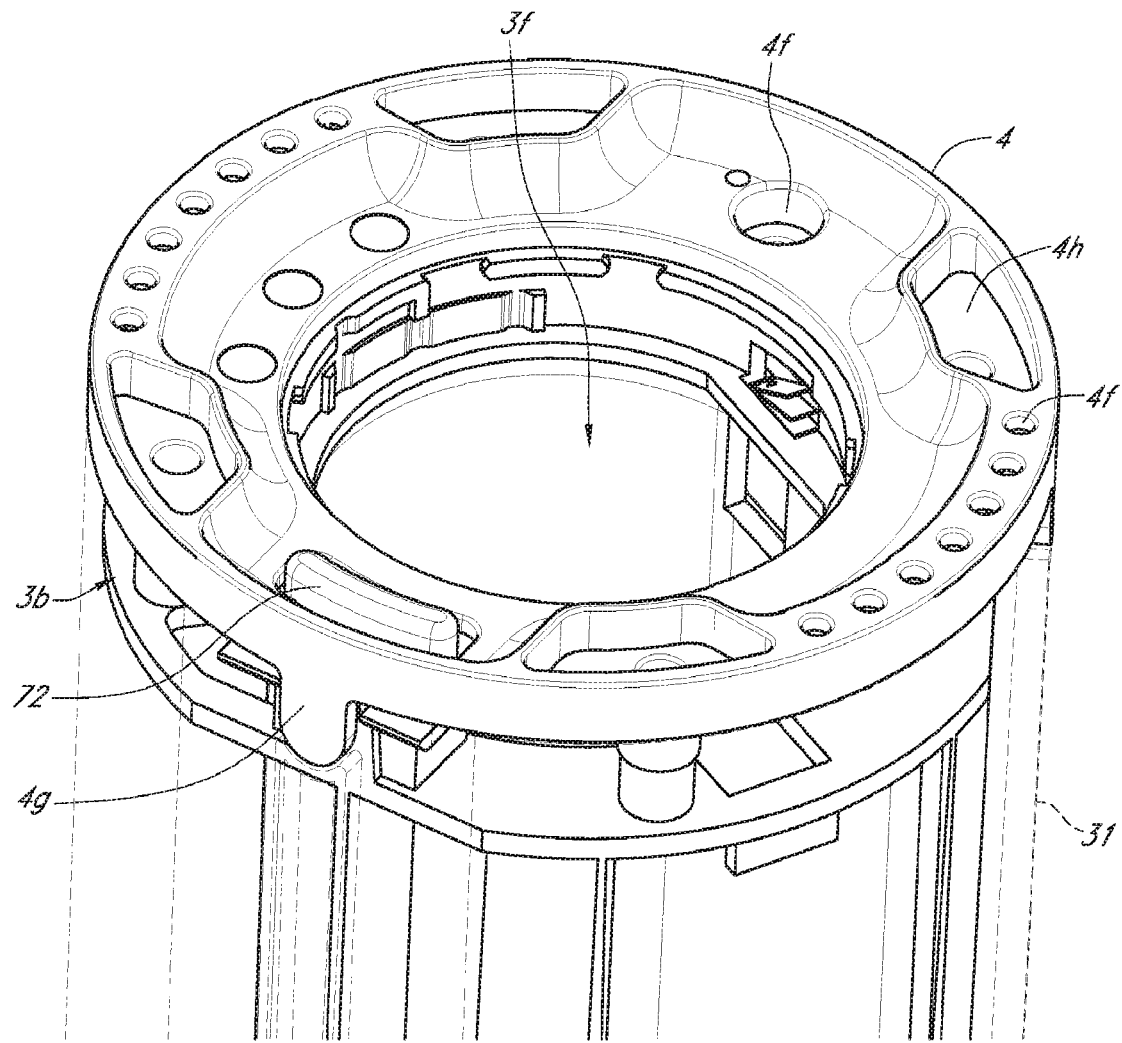
Figure 2E:
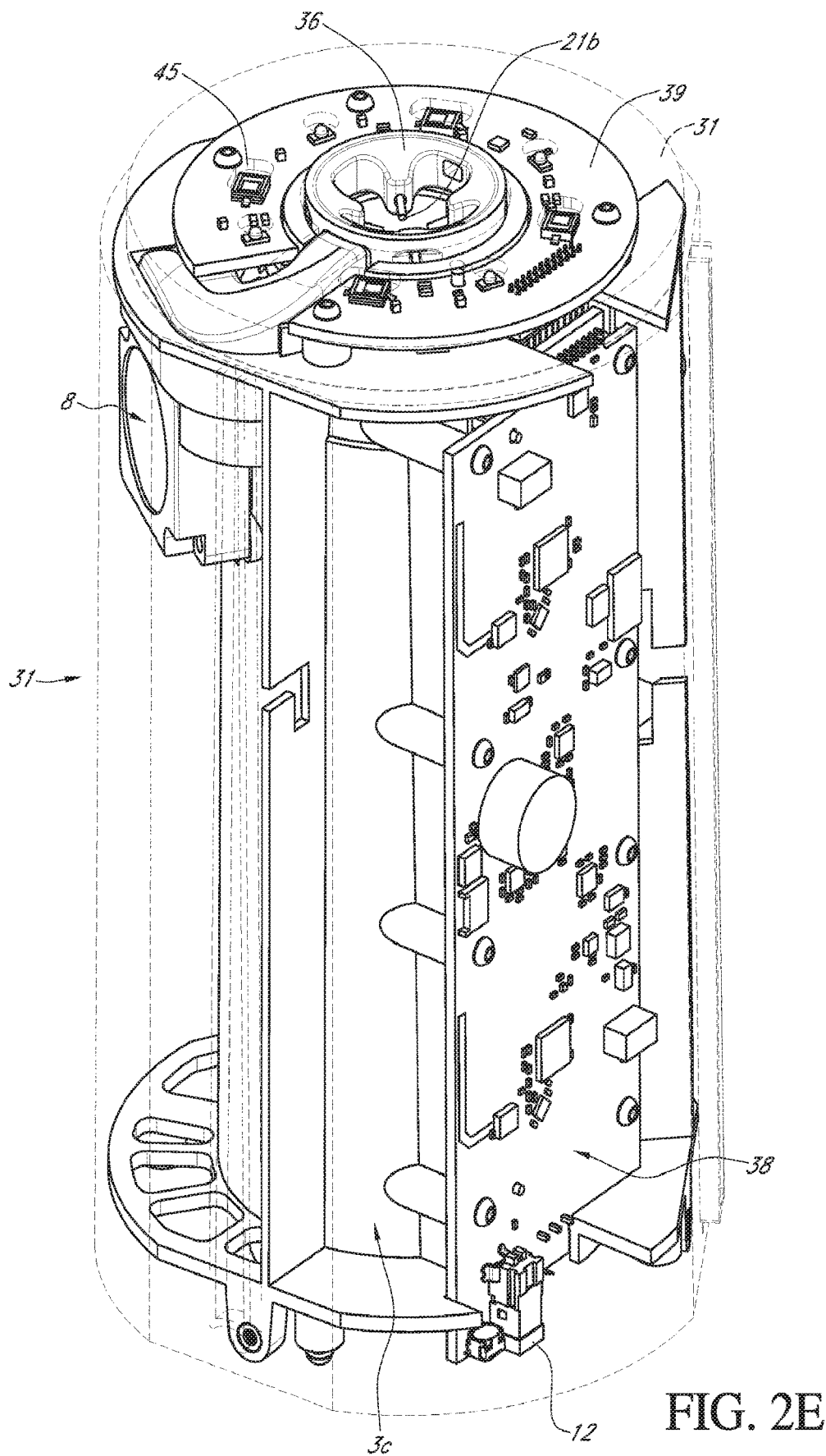
FIG. 2E is an assembled view of the Smart Candle Platform of FIG. 2 providing construction and assembly details with the inner cover enclosing the mid-frame with various electronic and operation components affixed therein to the mid-frame.

FIG. 2D is an assembled view of the Smart Candle Platform 10 of FIG. 2 providing further construction and assembly details for the slidable affixation of the lower portion of the inner cover to the base 4, base feet 44 and base cap 4a. As shown in FIG. 2C, base 4 is configured with annular base ridge 4b, base shelf 4c and base void 4e for slotted contact and engagement with the lower end of inner cover 31 shown in FIG. 2D. Inclusion of base tab 4g allows for fixed uni-directional engagement and assembly. Base 4 may be attached to the inner cover 31 via base fastener assemblies 4f which are apertures in which any fastener (glue, screws, bolts, expansion pegs and/or combinations thereof) (not shown) may be positioned to fix the end of inner cover 31 to base 4. FIG. 2D-1 is an assembled bottom view of the base 4 and inner cover 31 with the base cap 4a as well as several base foot 44 removed to better show base pads 4h. FIG. 2E is an assembled view of the Smart Candle Platform 10 disclosed herein as embodied in either FIG. 1, 2, or 3 configured with an inner cover 31 enclosing a mid-frame structure 3 with various electronic and operation components affixed therein. As shown, the mid-frame 3 is configured to engage with and be surrounded by an inner cover 31 having a generally round shape. As shown, the mid-frame 3 includes an upper annular shelf 3a as well as a lower annular shelf 3b which are generally round in shape. One of ordinary skill will appreciate the present disclosure (FIGS. 1-3) is not limited to one particular shape but that the combination of outer shell 2, opening 2a, inner cover 31 and mid-frame 3 can be configured to any shape desired with this concentric interconnection design between the preceding elements. As shown in FIG. 2E, upper annular shelf 3a and lower annular shelf 3b allow for the creation of a mid-frame axial compartment 3c into which a main PCB (printed circuit board) 38 may be affixed allowing for a control system 20 as discussed further herein. As disclosed herein, the main PCB 38 may have the following systems, system controls or connections, via either analog or digital systems, installed therein including a sensor system 11, a continuity sensor 12, an accelerometer 13, a gyroscope 14, a magnetic field based proximity sensor 15, a visual based proximity sensor 16, a fuel level sensor 17, a flame sensor 18, a control system 20, an ignition control system 21, an extinguisher system 22, an infrared (IR) remote control 23, a timer 24, a fuel control system 25, a power source (e.g., a battery) 26, a thermo-electric charging (Peltier) 27, a fuel feed system 28 (including controls), a communications system 30, including either or both a Wi-Fi or Bluetooth transmitter(s) and receiver(s), and combinations thereof collectively working separately or together supporting operation of a Smart Candle Platform 10 or Smart Candle Platforms 10 including a mesh network of Smart Candle Platforms 10. As shown, the recesses created by the upper and lower annular shelves (3a, 3b) provide adequate space to position the various components and systems disclosed through-out to allow for a compact, safe, aesthetically pleasing operational Smart Candle Platform 10 including for example fan 8 (shown in FIG. 2E), battery 26, ignition control system 21, ignition control system—electrical leads 21a and ignitor trough 34. As shown through-out FIGS. 2A-3D, the electrical connections between the various systems requiring electrical power may be positioned adjacent to and in either the ignitor trough 34 and/or mid-frame axial compartment 3c or other recesses located in the mid-frame 3 or combinations therein. One of ordinary skill will appreciate that a restricted access panel or cover 70 (not shown) having tab 72 positioned in base 4 may be required to ensure user access to the electronic components is limited as required by regulatory bodies and/or as recommended consumer product safety practices. (See FIGS. 2B-1 and 2D)

Figure 2F:
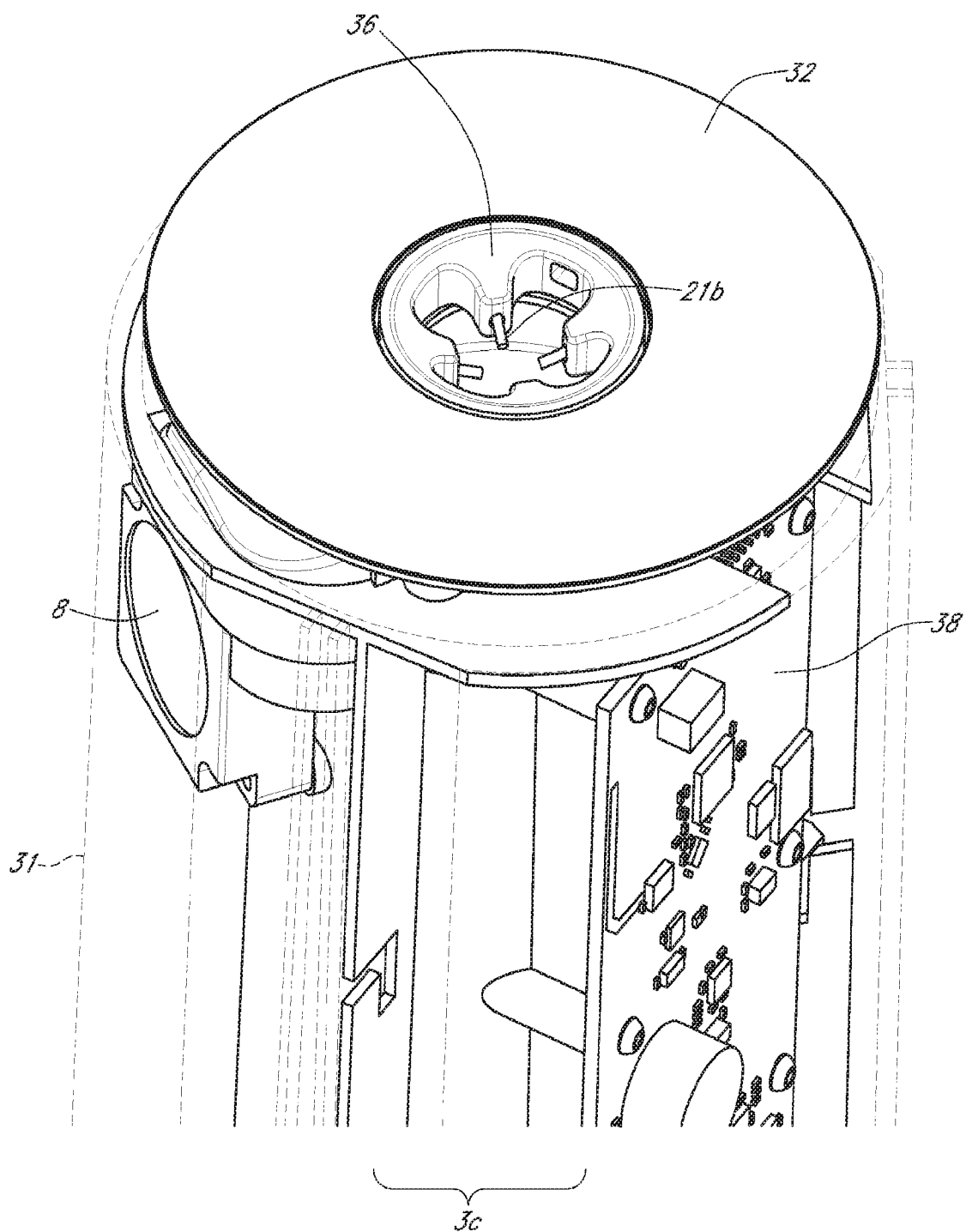
FIG. 2F is an assembled top view of the Smart Candle Platform of FIG. 2 providing construction and assembly details with the inner cover enclosing the mid-frame with various electronic and operation components affixed therein to the mid-frame and the top cover positioned therein.

FIG. 2F is an assembled top view of the Smart Candle Platform of FIG. 2 providing construction and assembly details with the inner cover 31 enclosing the mid-frame 3 with various electronic and operation components affixed therein to the mid-frame 3 and the top cover 32 positioned therein.

Figure 3A:
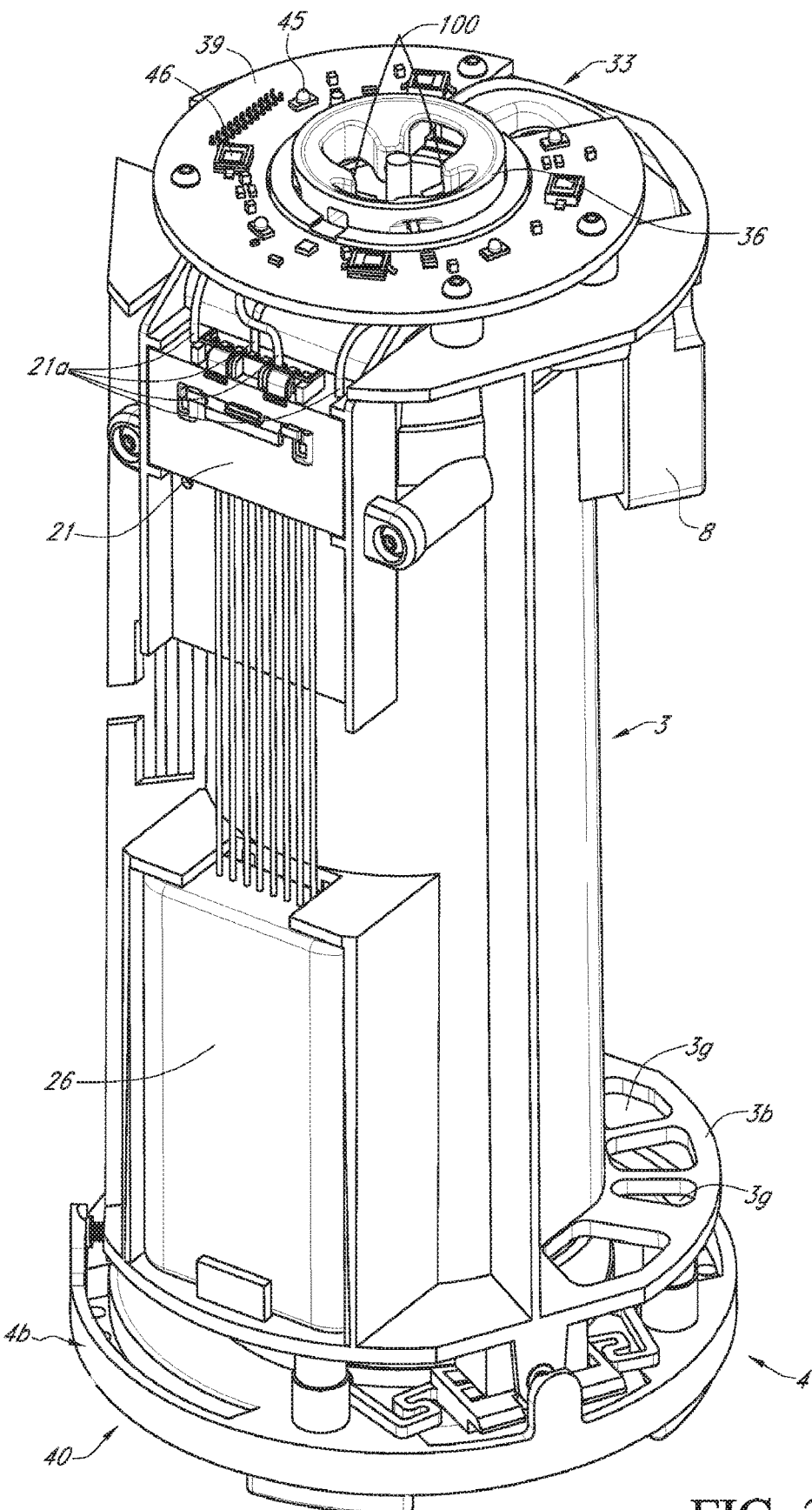
FIG. 3A is a perspective view of an embodiment of the Smart Candle Platform disclosed herein during operation with the outer shell, top cover and inner cover removed to better disclose the inner working portion of the Smart Candle Platform including the mid-frame resting on the base and various interworking components affixed therein.

FIG. 3A provides another perspective view of the Smart Candle Platform 10 disclosed herein during operation with the outer shell 2, top cover 32 and inner cover 31 removed to better disclose the inner working components of the Smart Candle Platform 10 including sensor PCB 39 with the mid-frame 3 resting on the base 4. As shown in FIGS. 2E, 3A, 3B and 3D, ignitor ring 36 is positioned on the upper portion of the mid-frame 3 extending out from the inner cover 31. As also shown in FIGS. 2E, 3A, 3B and 3D, sensor PCB 39 is positioned on the upper portion of the mid-frame 3 just under the inner sleeve 31. As disclosed herein, the sensor PCB 38 may have the following systems, system controls, or connections to it, installed therein including the sensor system 11, continuity sensor 12, accelerometer 13, gyroscope 14, magnetic field based proximity sensor 15, visual based proximity sensor 16, fuel level sensor 17, flame sensor 18, control system 20, ignition control system 21, extinguisher system 22, infrared (IR) remote control 23, timer 24, fuel control system 25, power source-battery 26, thermo-electric charging (Peltier) 27, fuel feed system 28 (controls), communications system 30, including either or both a Wi-Fi or Bluetooth transmitter(s) and receiver(s) and combinations thereof collectively working separately or together supporting operation of the Smart Candle Platform 10. One of ordinary skill will appreciate that multiple pairs of receivers and transmitters working together could allow formation of a mesh network comprised of a plurality of Smart Candle Platform(s) 10.

Figure 3B:
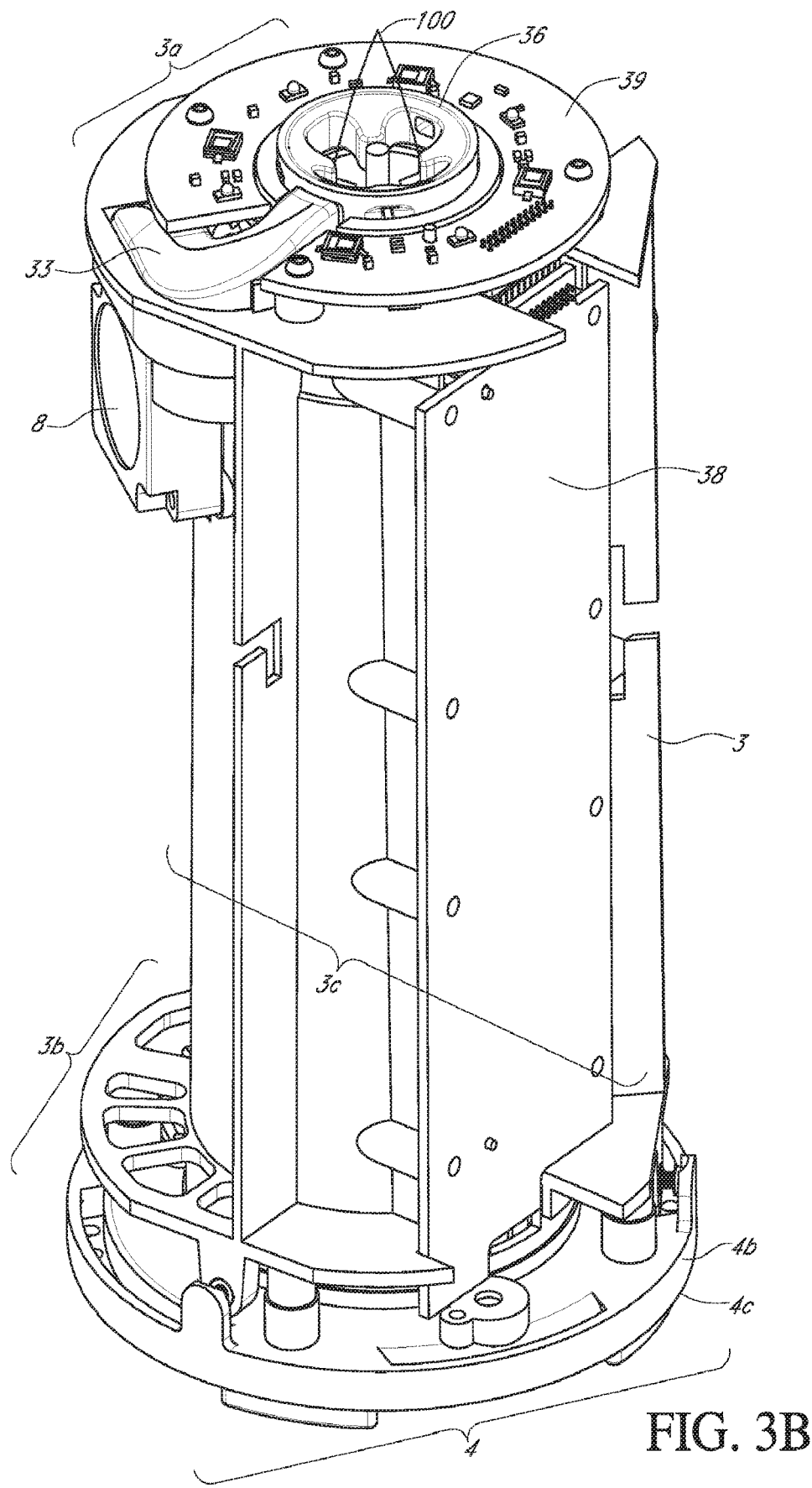
FIG. 3B is a perspective view of the other side of the mid-frame and various interworking components affixed therein resting upon the base as disclosed in FIG. 3 and throughout.
Figures 1, 3B:
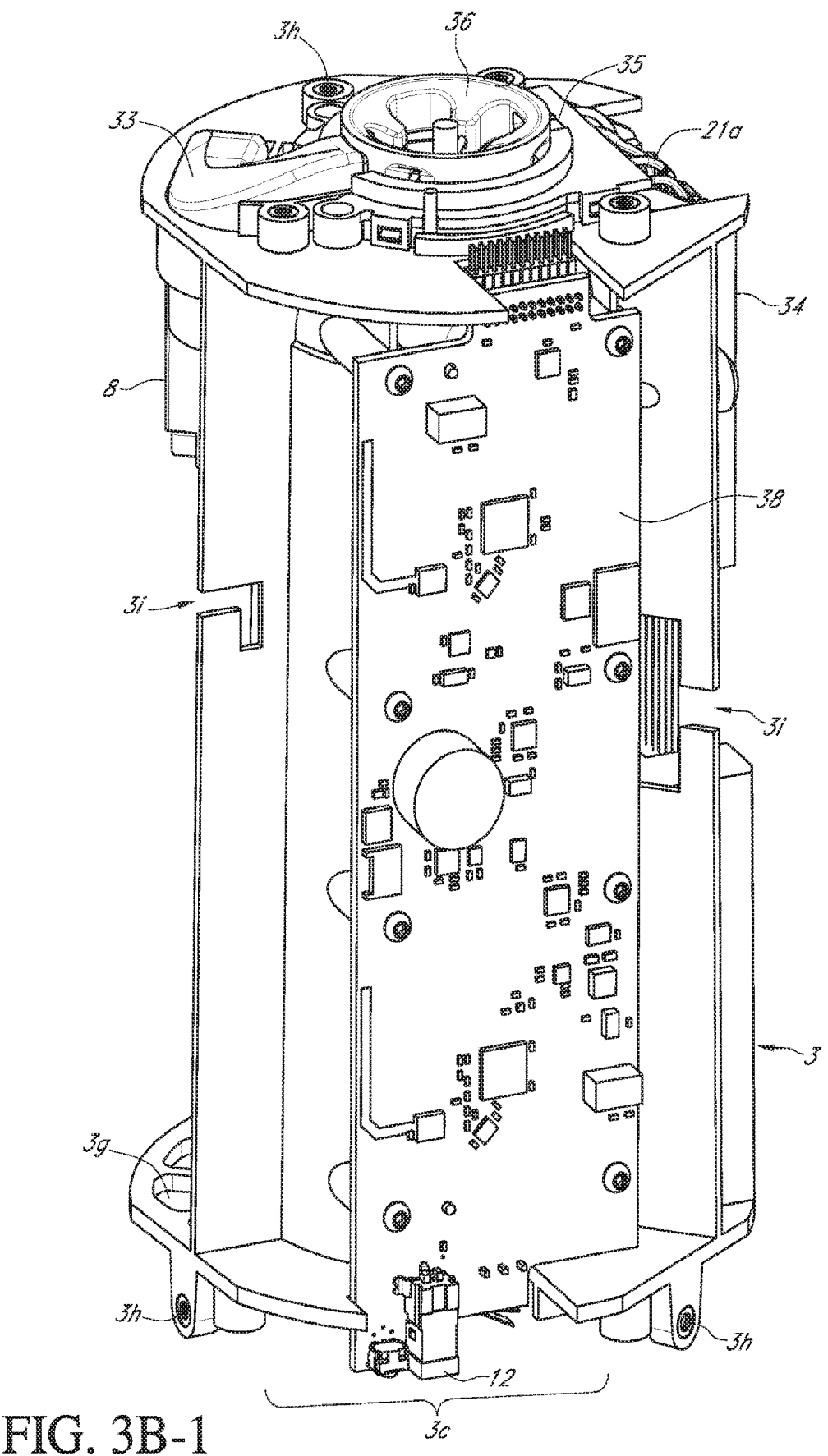

FIG. 3B is a perspective view of the other side of the mid-frame 3 including mid-frame lower tab 3d, mid-frame exhaust passage 3e and mid-frame aperture 3f having a main PCB 38 affixed in the mid-frame axial compartment 3c located between the mid-frame upper and lower annular shelves (3a, 3b) resting upon the base 4 and positioned for engagement with the base fastener assemblies 4f proximate the base ridge 4b and base shelf 4c. As shown, fan 8 is positioned in a recess located just under the upper mid-frame shelf 3a. Further, exhaust duct 33 is positioned in mid-frame exhaust passage 3e on the upper face of the mid-frame 3 in fluid communication with ignitor ring assembly 35 and ignitor ring 36.

FIG. 3B-1 is a detailed view of FIG. 3B with the base 4 removed to better illustrate the PCB 38 affixed to the mid-frame 3 in the mid-frame axial frame compartment and the position of the continuity sensor 12 between the lower portion of the mid-frame 3 and the base 4.

Figure 3C:
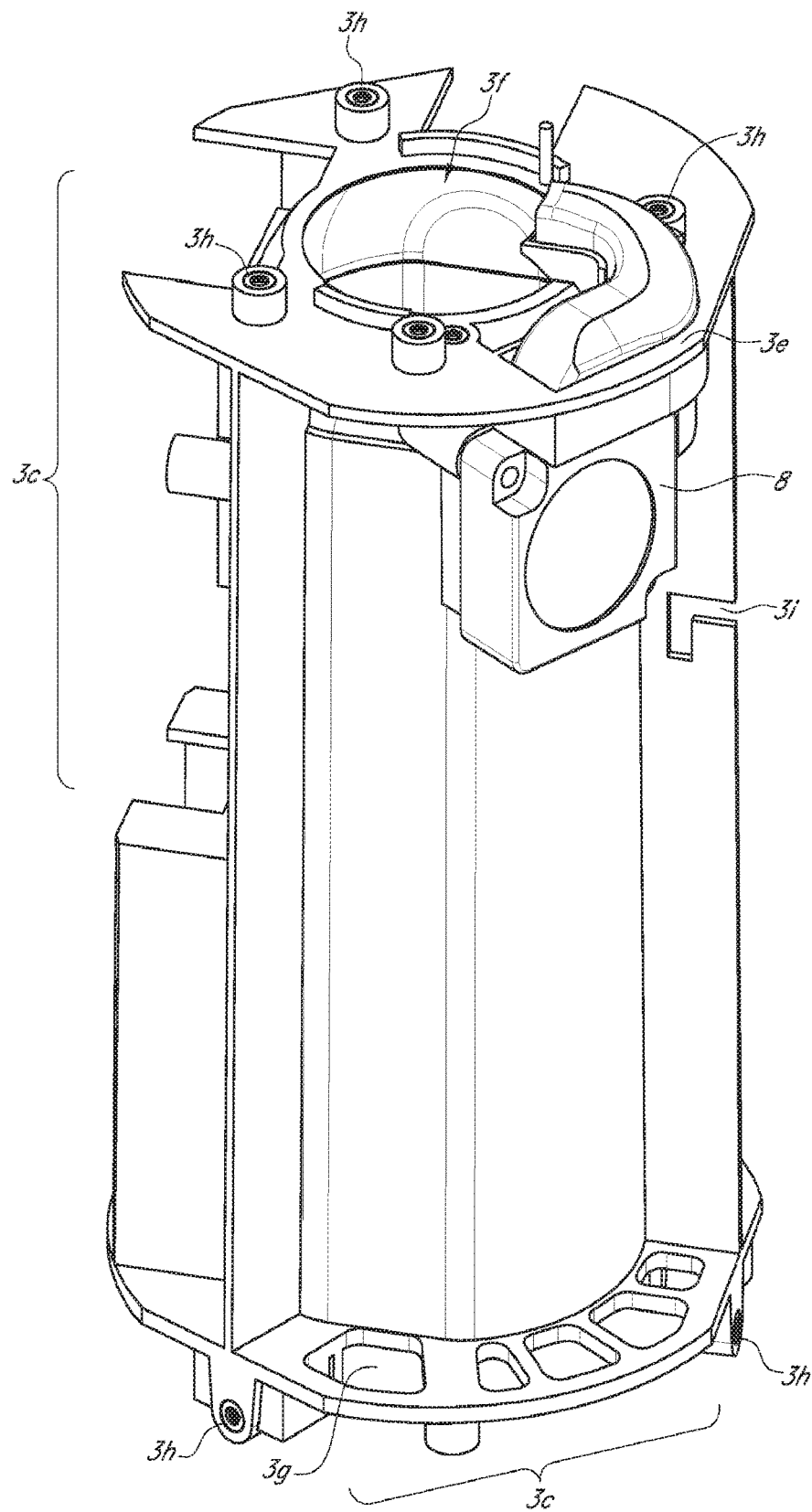
FIG. 3C is a perspective view of the opposite side of the mid-frame with only the fan affixed therein.
Figures 1, 3C:
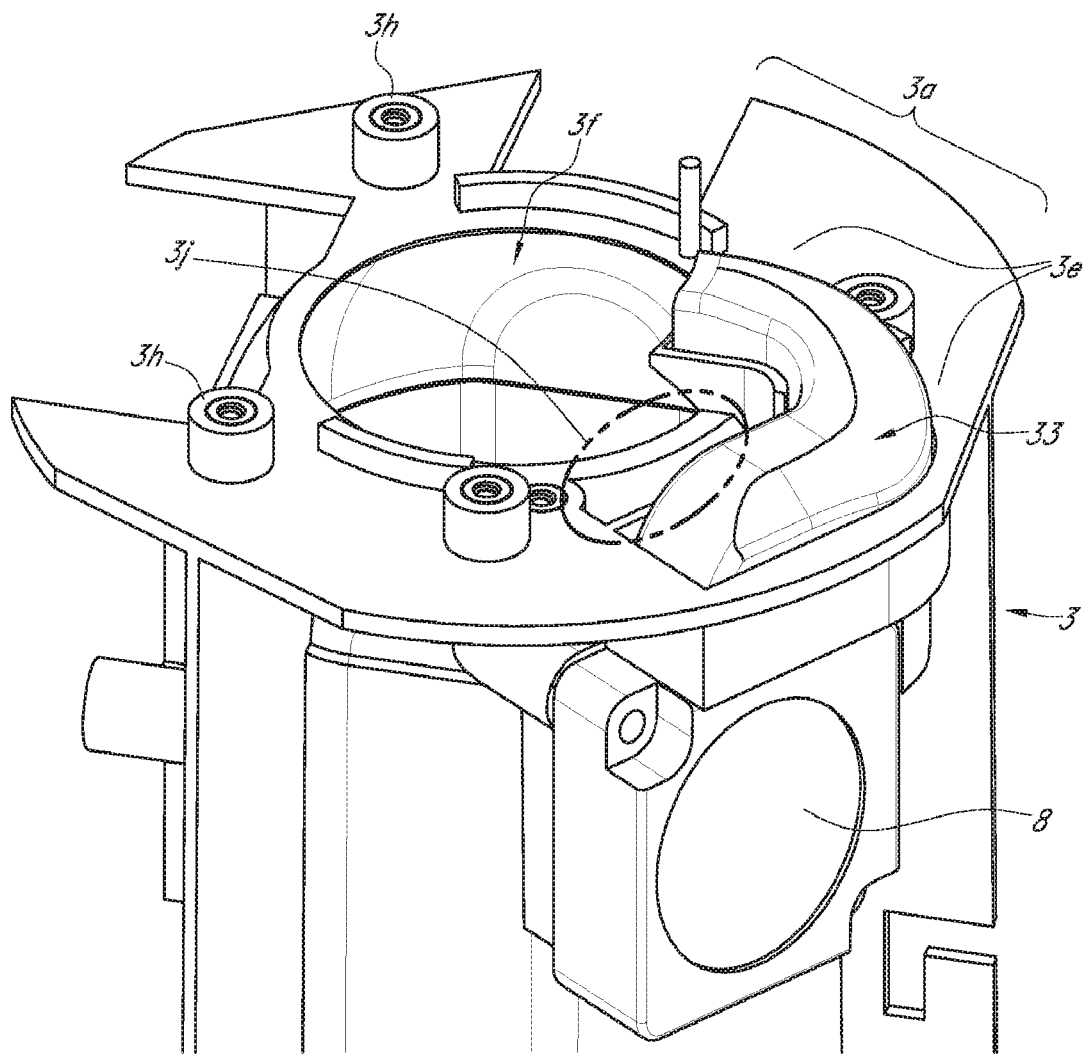

FIG. 3C is perspective view of the mid-frame 3 with only the fan 8 affixed to best illustrate the various components of the mid-frame 3 to illustrate the other side of the mid-frame 3. FIG. 3C-1 is a perspective view of the upper portion of the mid-frame 3 with only the fan 8 and exhaust duct 33 affixed therein. The upper portion of mid-frame is configured with a wax overflow collection trough proximate the mid-frame aperture 3f and mid-frame exhaust passage 3e for engagement with exhaust duct 33. As disclosed, fan 8 connected to exhaust duct 33 may be used as part of the extinguishment system 22 i.e. when a sensor 11a from a sensor system 11 is connected to the extinguishment system 22 provides a signal that there exists an unsafe condition, fan 8 may be operated to send a gust of air to the flame 100 to extinguish the flame 100. In other embodiments, fan 8 can be operated so as to remove or pull excessive smoke away from the flame 100 during operation and or in extinguishment mode, can be operated so as to rapidly remove the air around the flame 100 allowing for extinguishment and avoidance of unsafe operation.

Figure 3D:
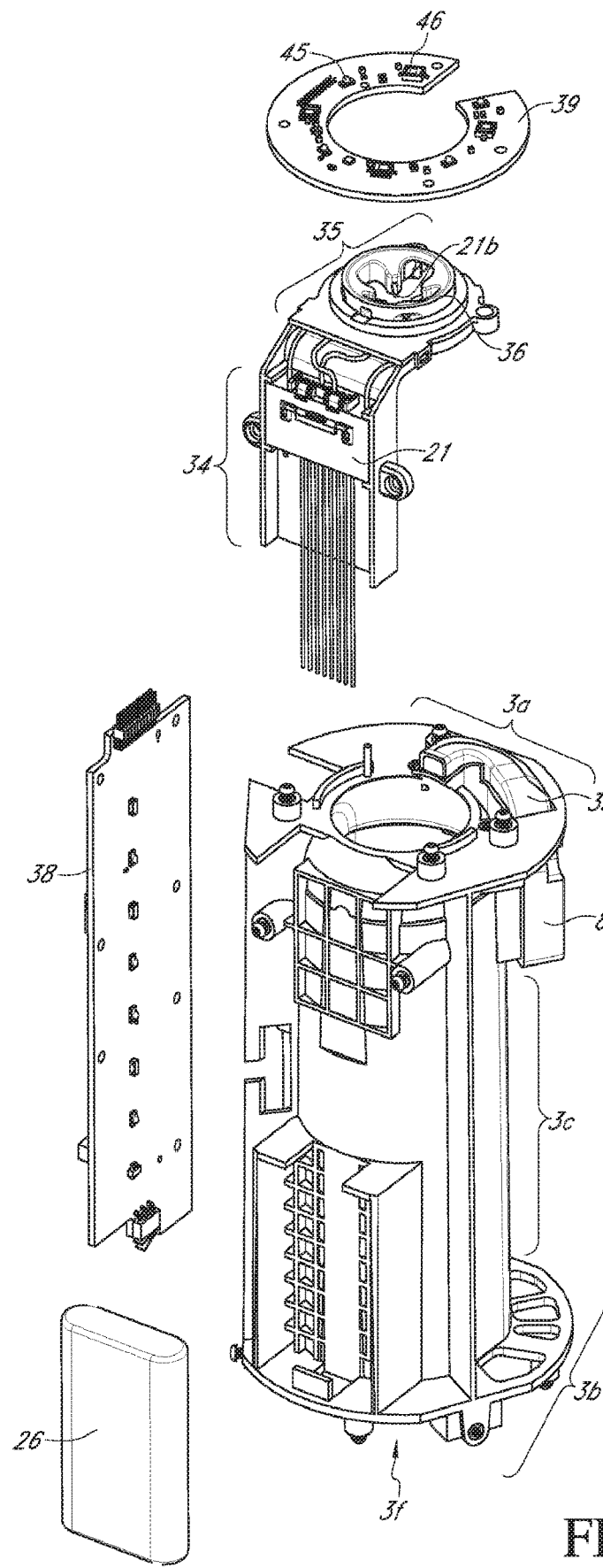
FIG. 3D is an exploded view of the embodiment of the Smart Candle Platform disclosed at FIGS. 2 and 3 illustrating the shape, position and relationship between the interior of the Smart Candle Platform as related to the mid-frame, the fan, the exhaust duct, gasket, ignitor, ignitor assembly, main PCB, battery, sensor PCB and electrical leads connecting the various powered components.

FIG. 3D is an exploded view of Smart Candle Platform 10 providing additional illustration of one embodiment therein particularly as related to the shape, position and relationship between the interior of the Smart Candle Platform 10 as related to the mid-frame 3, the fan 8, exhaust duct 33, ignitor 21b, ignitor assembly 35 positioned under ignitor ring 36 and base 4, main PCB 38, battery 26, sensor PCB 39 and electrical leads (ignition control system 21a and battery leads) connecting the various powered components of Smart Candle Platform 10. As disclosed herein, the sensor PCB 39 is illustrated having infrared (IR) sensors 45 and thermopiles 46 arrayed and arranged around the circumference of the sensor PCB 39. Applicant has found that at least one and preferably multiple IR sensors 45 and thermopiles working together improve monitoring and control of the wick 41a of candle 41 and particularly flame 100. Ignitor ring 36, having the clover-leaf shape as shown through-out, which surrounds the wick 41a and flame 100, has been found to be one configuration allowing multiple ignitors 21b for improved control of wick 41a and flame 100 solving the problem(s) of wick and flame migration.

Figure 3E:
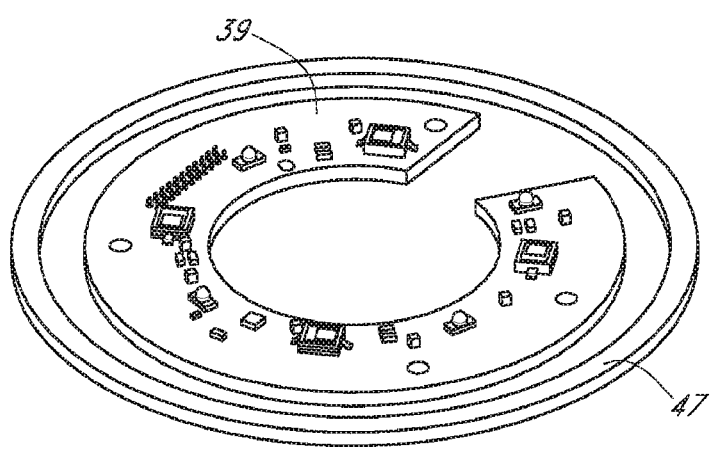
FIG. 3E is simplified view of a possible scent ring useful with the present disclosure positioned adjacent to a sensor PCB.
Figure 4:
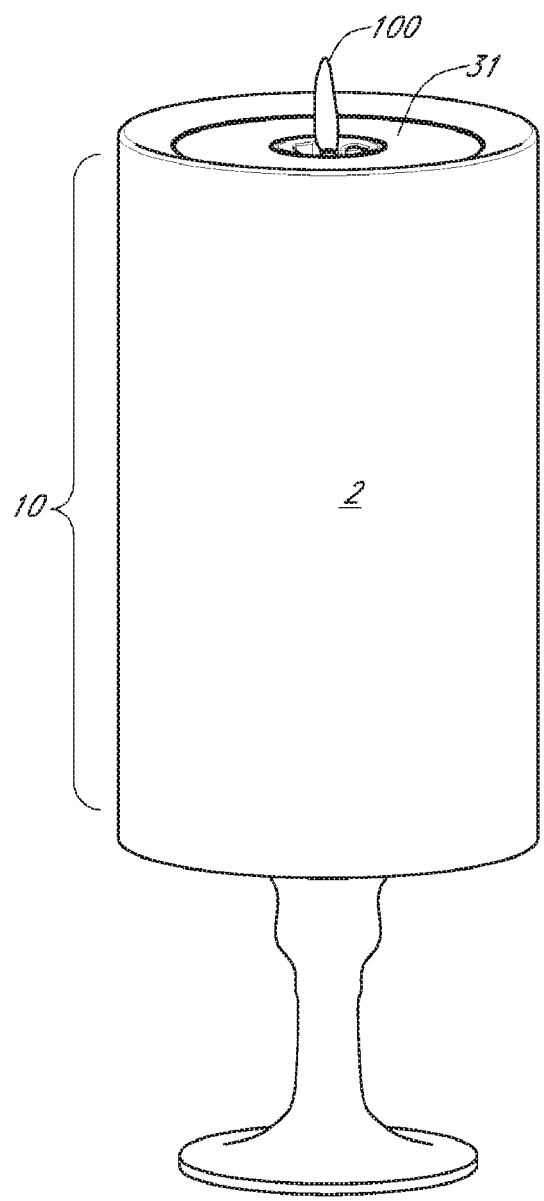
FIG. 4 is a first view of a Smart Candle Platform in operation which embodies at some of the various features disclosed herein.
Figure 5:
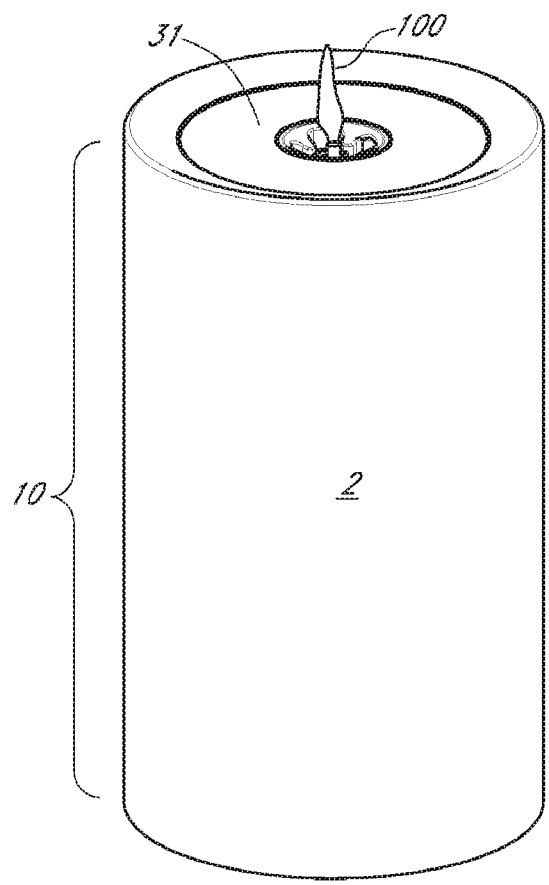
FIG. 5 another view of a Smart Candle Platform in operation which embodies at some of the various features disclosed herein.

FIG. 3E illustrates one embodiment of a scent ring 47 useful with the present disclosure positioned adjacent to a sensor PCB 39 and ignitor ring 36. One of ordinary skill will appreciate that the scent ring 47 may have any shape that works with a particular configuration of the Smart Candle Platform 1 disclosed herein. Further, the scent ring 47 may be used with a sensor PCB 39 and ignitor ring 36 as illustrated or may be used in a Smart Candle Platform 10 configured for use without a mid-frame 3 or ignitor ring 36 with the scent ring 47 positioned proximate live flame 100 to provide heat which may be useful in warming-up the scent ring 47 to activate the scent therein for distribution. The scent ring 47 may be positioned inside the sensor PCB 39 or external to the sensor PCB 39 as shown, without limitation or restriction, as required for a particular application or configuration.

In another embodiment of the Smart Candle Platform and System 10 as disclosed and shown throughout FIGS. 6-29, FIG. 6 is a perspective view of a Smart Candle Platform and System 10 in operation which embodies at least some of the various features disclosed herein. FIG. 6A is a side perspective view of a Smart Candle Platform and System 10 as illustrated and disclosed in FIG. 6 herein. For the embodiments of the Smart Candle Platform and System 10 shown in FIGS. 6-29, element descriptions and names have been assigned numbers 110-179 as found in the Table of Elements herein. As shown, the Smart Candle Platform and System 10 is comprised of a top cover 110, an outer shell 151, an inner cover 152, a fuel source (cartridge system) 130 and a base 4. The top cover 110 has an opening 116 and is positioned at an upper end of the Smart Candle Platform and System 10. The outer shell 151 has an upper end and a lower end wherein the upper end and the lower end form a hollow interior and an opening for inserting and securing the inner cover 152. The inner cover 152 is comprised of a support frame 152a, a protective cover 152b and a shell support 152c. The shell support 152c has an upper opening that connects to a lower opening to form a hollow interior. The shell support 152c is positioned between the protective cover 152b and the outer shell 151. The protective cover 152b has an upper opening that connects to a lower opening to form a hollow interior for inserting the support frame 152a. The protective cover 152b may be configured to engage with and surround the support frame 152a. The support frame 152a has an upper opening that connects to a lower opening to form a hollow interior. The support frame 152a forms a housing for the insertion of the fuel source 130 which is disclosed as a removable and or re-usable cartridge but as one of ordinary will appreciate may also be configured as a fixed reservoir or tank (not shown) which is refillable and non-removable, without additional limitations or restrictions. The fuel source 130 may be configured as a cartridge and may be positioned within the support frame 152a of the inner cover 152. The base is configured to cooperative engage with the lower end of the outer shell 151 and the lower end of the inner cover 152. In one embodiment, the cartridge 130 may rest upon the base. The base is configured to support the outer shell 151 and the inner cover 152 and to enclose the cartridge 130.

As shown in FIG. 6A, the outer shell 151 may be configured of wax, but is not so limited and may be constructed from any material which is suitable for a particular application including without limitation therein paper (i.e. cardboard), metals (i.e. steel or aluminum) as well as plastic, and combinations thereof, without any limitation and/or restriction unless otherwise indicated in the following claims. One of ordinary skill will appreciate that the outer shell 151 that in addition to providing ornamentation and enhancing the attractiveness of the Smart Candle and Platform 10, may be designed for the purpose of protecting and reducing damage to the interior components of Smart Candle Platform and System 10 in the event of an accident such as falling on the ground from a higher surface. (Not shown) In addition, the outer shell 151 may be designed or customized with different images, color, size and shape to serve the purpose of decoration without any limitation and/or restriction unless otherwise indicated in the following claims. A decorative embodiment of the outer shell 151 may enhance the attraction of the Smart Candle Platform and System 10 to the end user further improving its desirability.

Figure 6:
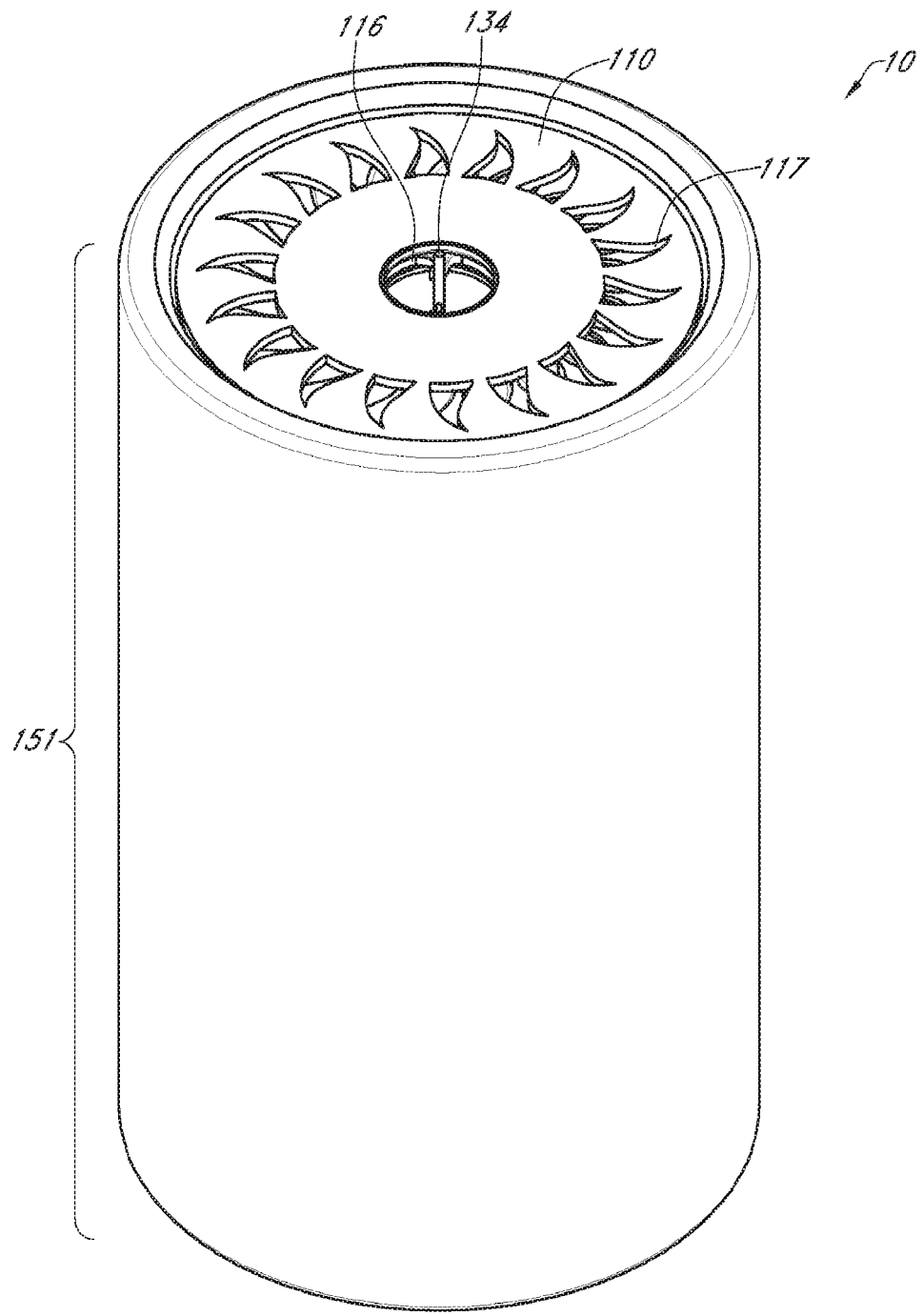
FIG. 6 is a perspective view of another embodiment of a Smart Candle Platform and System in operation which embodies at least some of the various features disclosed herein.
Figure 6A:
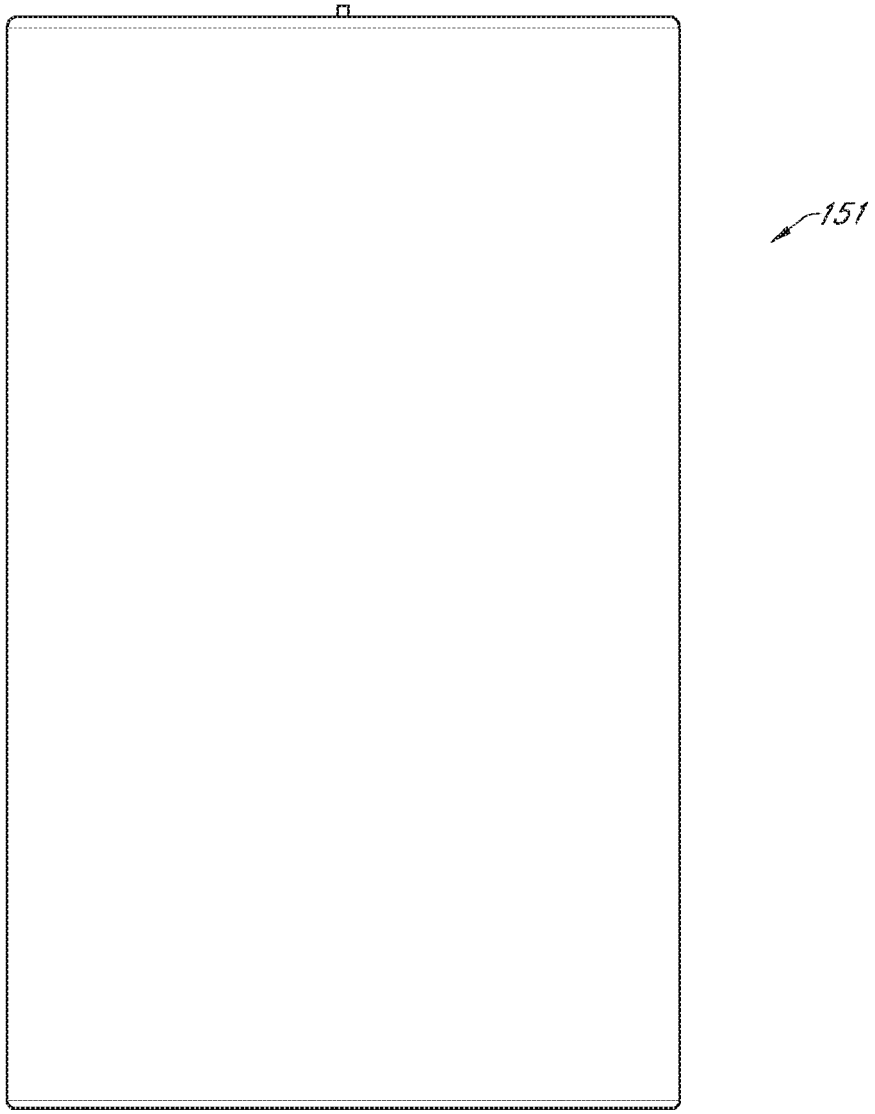
FIG. 6A is a side perspective view of a Smart Candle Platform and System as illustrated and disclosed in FIG. 6 herein.
Figure 6B:
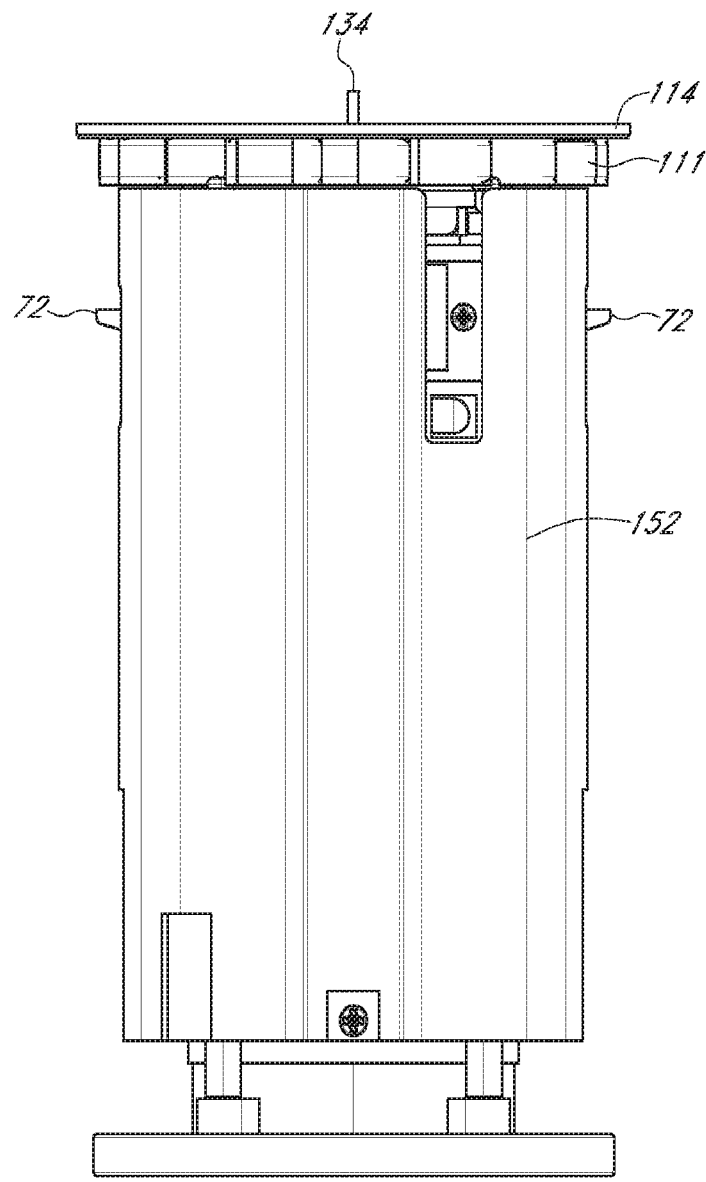
FIG. 6B is an assembled view of a Smart Candle Platform and System with an outer shell cover removed providing a protective device cover and an injection molded support frame positioned interiorly as disclosed herein.

FIG. 6B is an assembled view of a Smart Candle Platform and System 10 with an outer shell 151 cover removed. As shown, the inner cover 152 is comprising a shell cover 152c, a protective device cover 152b and an injection molded support frame 152a positioned interiorly of the protective device cover 152b as shown. In one embodiment, the inner cover 152 may be removed from the outer shell 151 upon application of a downward force on the top cover 110 or the upper portion of the inner cover 152. In another embodiment, the inner cover 152 may be removed from the outer shell 151 by unlocking or depressing a locking tab 72 positioned interior of the inner cover 152. A scent pan 111 is positioned at the upper portion of the inner cover 152. The scent pan 111 (also see FIGS. 8-11) is decorative with different colors, images and shapes for the purpose of increasing attractiveness of a Smart Candle Platform and System 10 without any limitation and/or restriction unless otherwise indicated in the following claims. As shown, the injection molded support frame 152a is positioned at the base 4 and is configured to engage with the base 4 and the fuel source 130 configured as a cartridge.

Figure 6C:
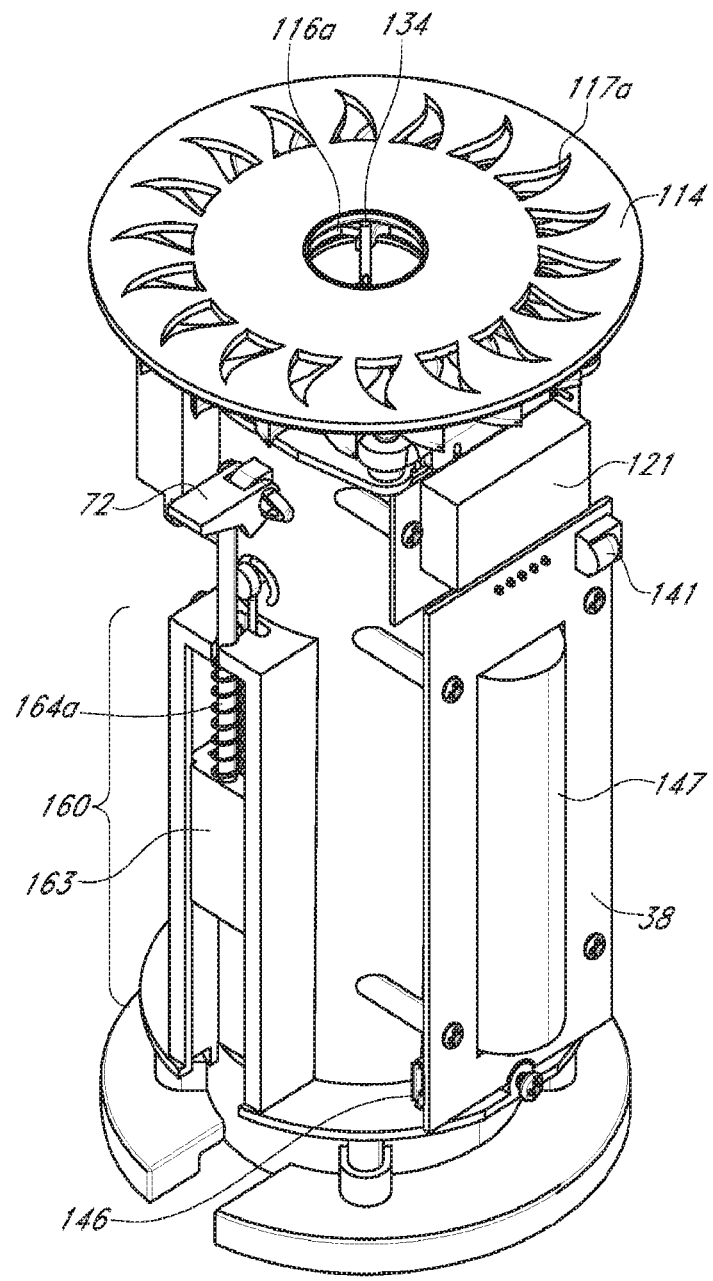
FIG. 6C is a detailed view of a Smart Candle Platform and System with the protective cover and the support frame removed providing an ignition PCB, IR remote sensor and USB charge port as disclosed herein.

FIG. 6C is a detailed view of a Smart Candle Platform and System 10 with the protective cover 152b and the support frame 152a removed illustrating an ignition PCB 121, IR remote sensor 141 and USB charge port 146 as disclosed herein. The main PCB 38 for the ignition control system 174 may be configured to control the tip alert feature and the refill level detection system which may be powered by a lithium ion on-board battery 148, without restriction or limitation. The USB charge port 146 is configured for providing power for the Smart Candle Platform and System 10 either via USB charging (computer or charger) or via battery 148. In addition, the control system 140 may be included as an on/off switch 173, an ignition control system 174, an extinguisher system 175, an infrared (IR) remote control system 171, a timer 178, a password 179, a fuel control system 172, a fuel storage system 176, a fuel system 177 and and/or a combination of the preceding, subject to a particular application, without any limitation and/or restriction.

Figure 6D:
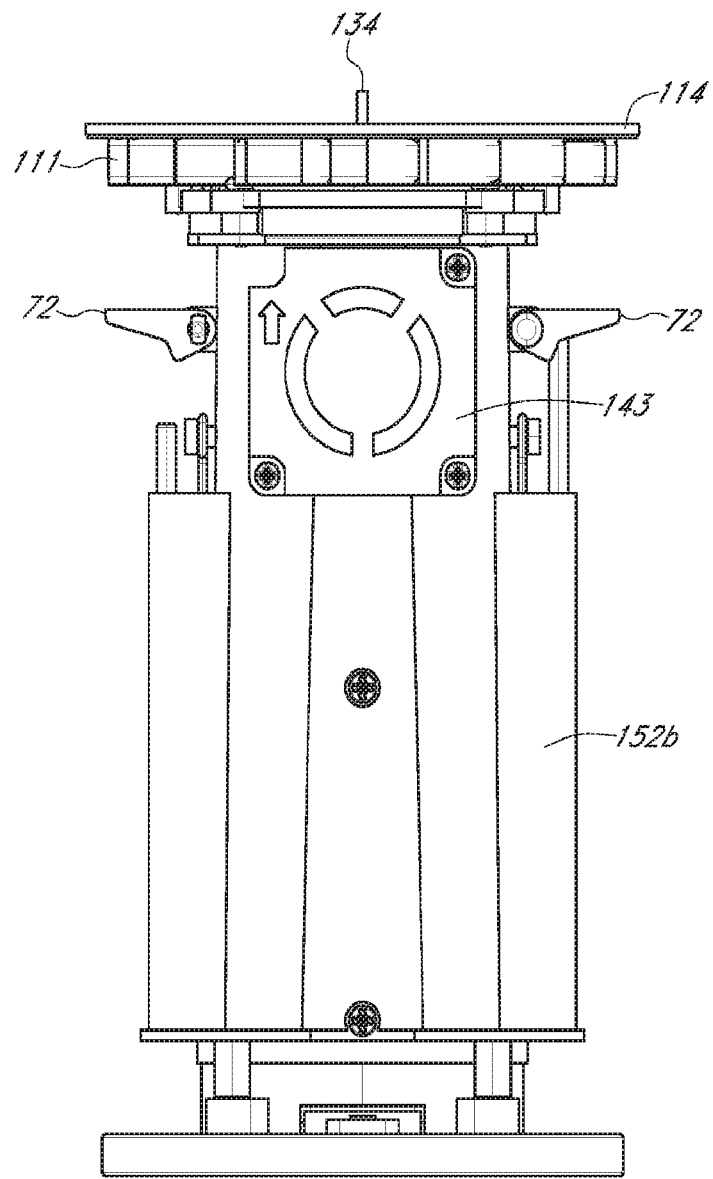
FIG. 6D is a side view of a Smart Candle Platform and System with a pair of locking tab supporting a push/push cam mechanism for retaining device as disclosed herein.

Another feature disclosed is the push/push cam mechanism 160. As shown in FIG. 6D which is a side view of an embodiment of a Smart Candle Platform and System 10 with a pair of locking tabs 72 supporting a push/push cam mechanism 160 for retaining the present embodiment of the outer shell 151 with the inner cover 152 as disclosed herein, when the Smart Candle Platform and System 10 is configured with a removable outer shell 151. The locking tab 72 is positioned interior of the inner cover 152 and extends to the interior of the outer shell 151 to allow disengagement of the outer shell 151 from the inner cover 152. The locking tab 72 is activated by a push/push cam mechanism 160 for retaining the outer shell 151 with the inner cover 152 while in use. When the user depresses the top cover 110 downward, the inner cover 152 disengages the locking tab 72 and releases the outer shell 151 from the inner cover 152. To assemble the outer shell 151 and the inner cover 152, the user may slidably insert the inner cover 152 into the hollow interior of the outer shell 151. The locking tab 72 may be extended to engage the outer shell 151 with the inner cover 152 upon application of a downward force on the upper portion of the inner cover 152.

Also, shown are other features of the embodiment configured with a self-extinguishing fan 143 and integrated on-board electronics assembly. As shown in FIG. 6D, the self-extinguishing fan 143 is positioned at the upper portion of the support frame 152a for auto off functions and safety tip sensor 142. The integrated on-board electronics assembly may also be configured with a push button ignition, a push button or auto extinguish options 149, an automatic tip detection 145, a timer 178 and/or password 179 options and combinations therein. The push button 156 is mounted on the exterior of the inner cover 152 and is configured for simple but secure user engagement. After removing the inner cover 152 from the outer shell 151, the user may press on the push button 156 to release the fuel source 130 cartridge from the inner cover 152 for replacement or refilling. The user then inserts a new or refilled cartridge 130 into the hollow interior of the support frame 152a of the inner cover 152.

Figure 6E:
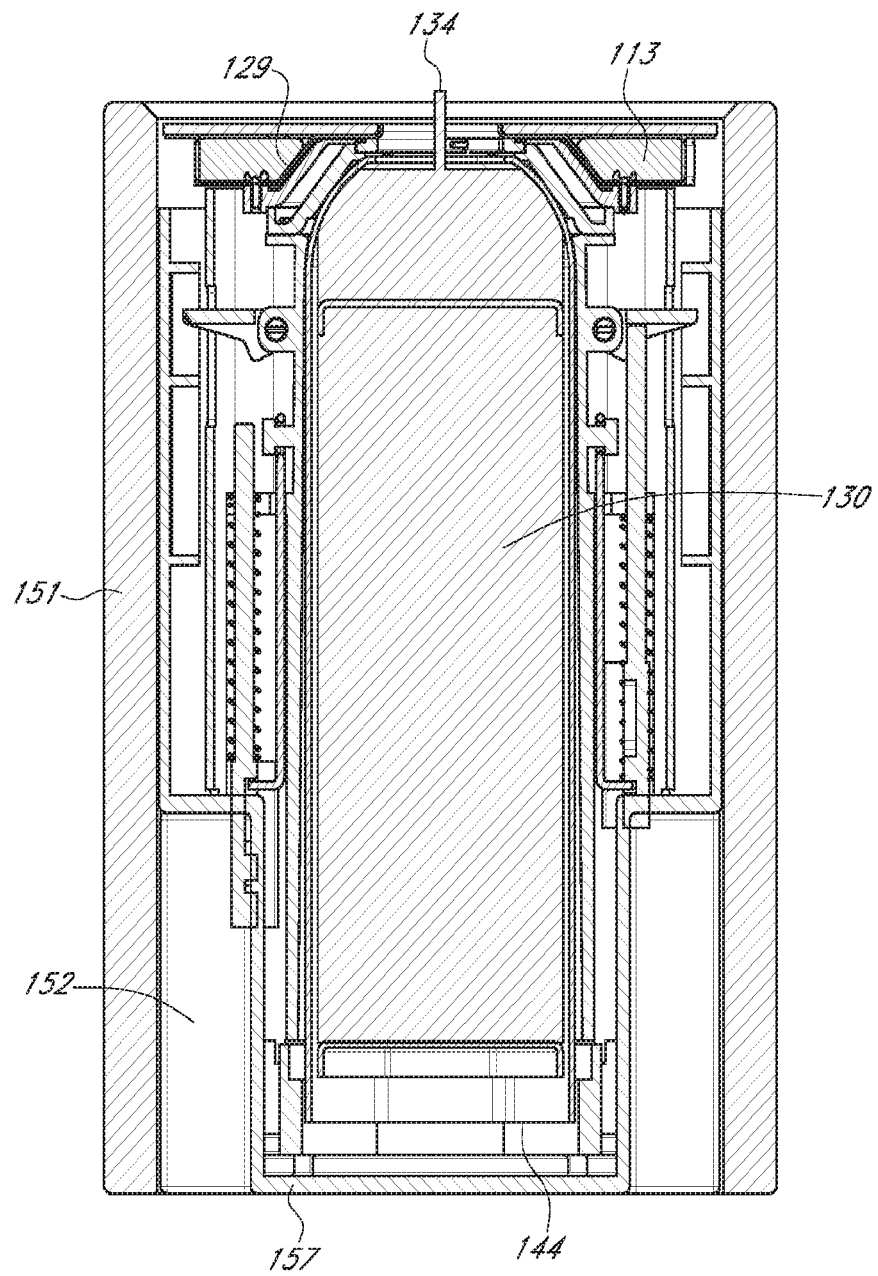
FIG. 6E is a cross-sectional view of a Smart Candle Platform and System in assemble which embodies at some of the various features disclosed herein.

FIG. 6E is a cross-sectional view of a Smart Candle Platform and System 10 in assembly which embodies at some of the various features shown, the Smart Candle Platform and System 10 is designed with numerous features. For instance, the push/push cam mechanism 160 allows this embodiment to be accessed with ease. The internal ignition wire routing 123 is configured for streamline design. The inner support shell 152c is designed for various decorative materials. In one embodiment, the outer shell 151 may be decorative and interchangeable while in another embodiment, the outer shell 151 may be decorative and fixed. The recessed storage pocket 158 is configured for storage of a decorative slip on type cover. The cartridge 130 may be interchangeable using the quick release retaining clips 132. The sensor for fuel cartridge 177 may send signal to the PCB for automatic re-order notification when a low fuel level is measured.

Figure 6F:
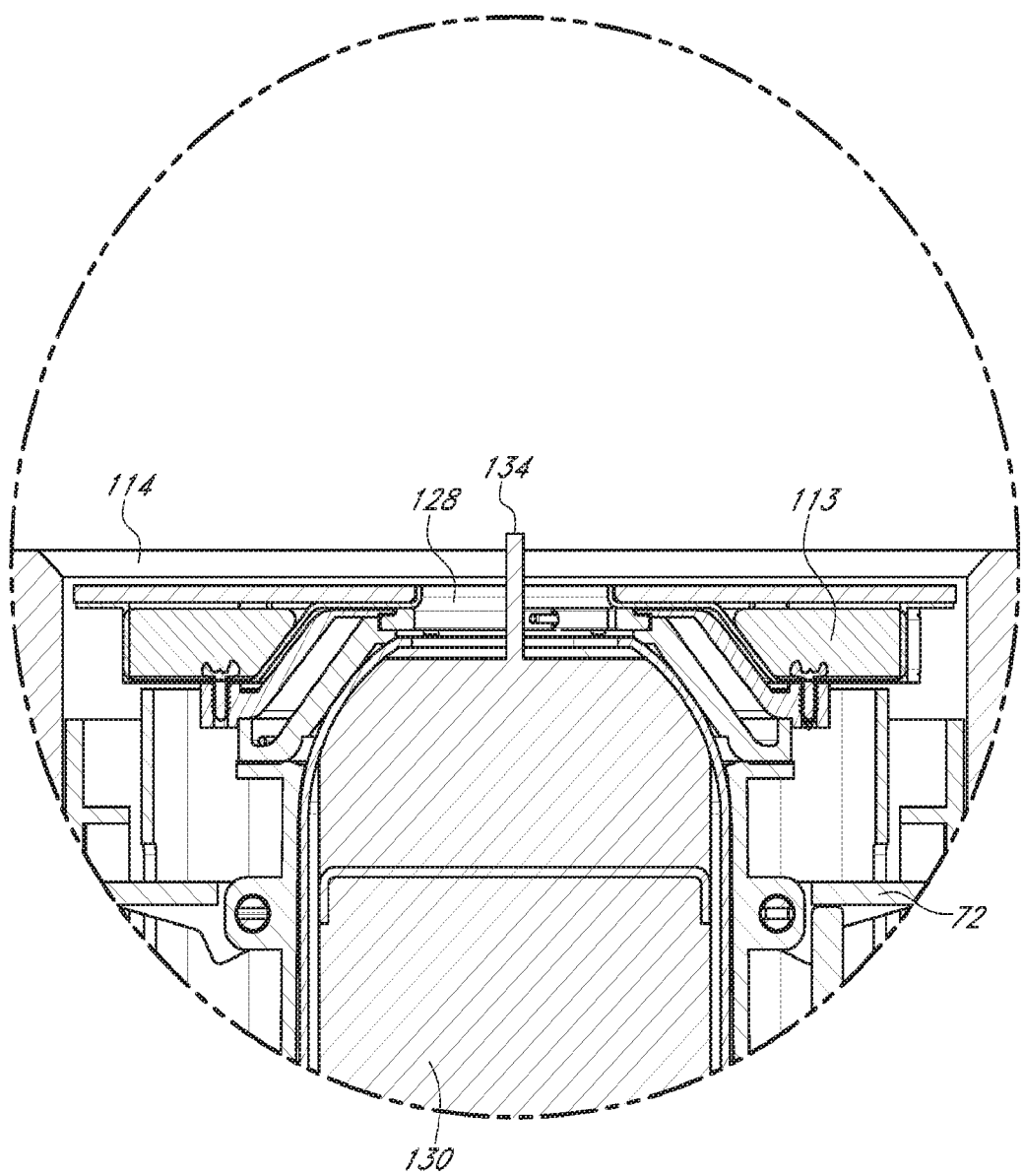
FIG. 6F is another cross-sectional view of a portion of a Smart Candle Platform and System illustrating the upper end of the Smart Candle Platform having a fuel cartridge positioned within the embodiment as disclosed herein.

FIG. 6F is another cross-sectional view of a portion of a Smart Candle Platform and System 10 illustrating the upper end of the Smart Candle Platform having a fuel cartridge 130 positioned within the embodiment as disclosed herein configured with a top cover 110 and an ignition system 120. In one embodiment, the opening 116 of the top cover 110 may be constructed or designed in a way to allow refueling or replacement of the fuel source (cartridge) 130. Depending on the particular application, the top cover 110 may be constructed together with the outer shell 151 or constructed separately and conventionally attached to the inner cover 152. In one embodiment, the top cover 110 may be inserted into the Smart Candle Platform and System 10 by turning or twisting the top cover 110 in the clockwise direction. In this configuration, the top cover 110 may be removed from the Smart Candle Platform and System 10 by turning or twisting the top cover 110 in the counter clockwise direction. In addition, as shown in FIG. 6F, an ignition system 120 may be positioned at the upper end of the support frame 152a and underneath a scent pan 111 and the top cover 110. The ignitor system 120 may be electrically connected to a battery 148 positioned proximate the support frame 152a. In one embodiment, there is a ceramic igniter prong 124 positioned at an opening of the scent pan 111.

Figure 6G:
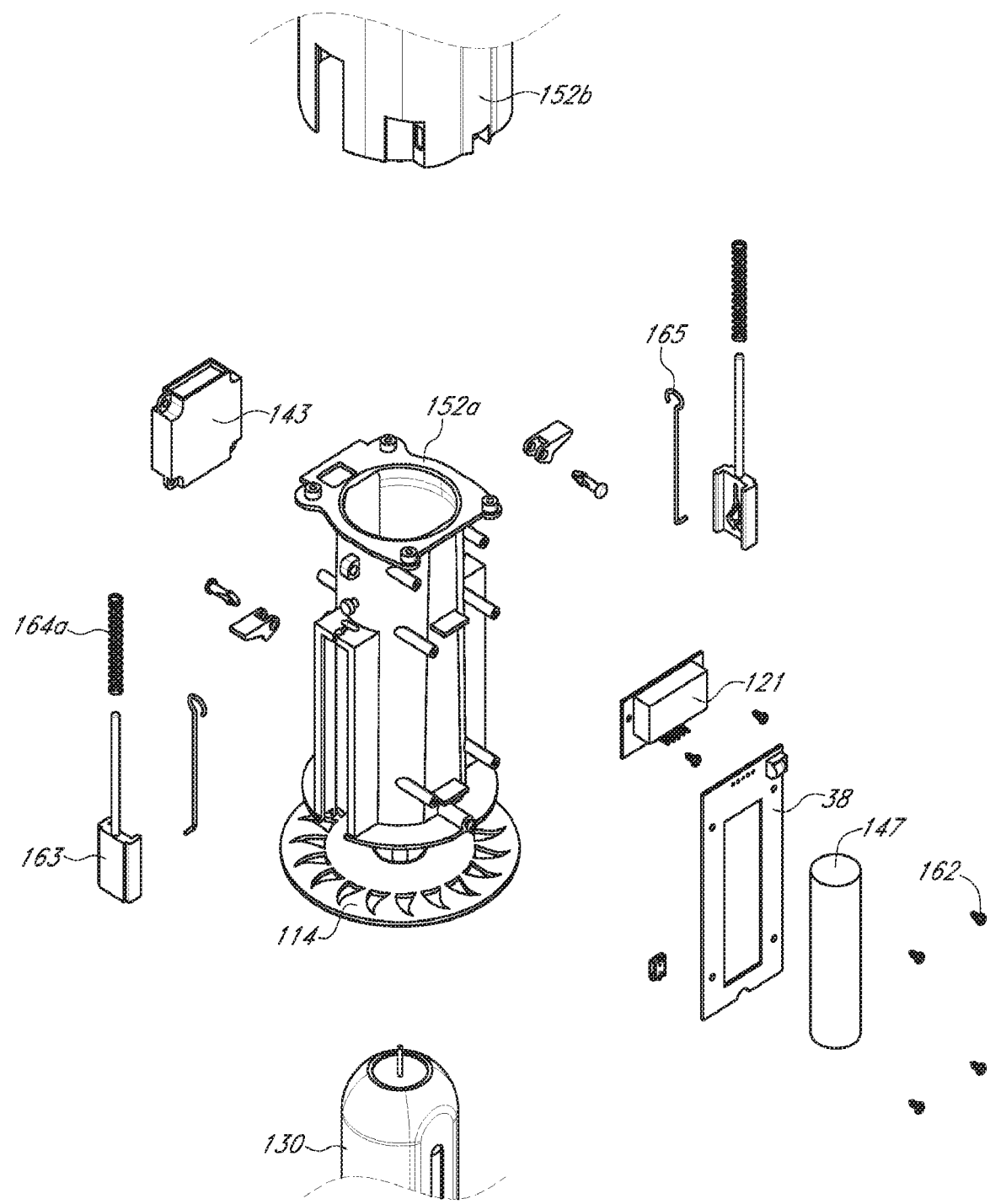
FIG. 6G is an exploded view of a Smart Candle Platform and Systems with various electronic and operation components as shown in FIGS. 6-6F.
Figure 6H:
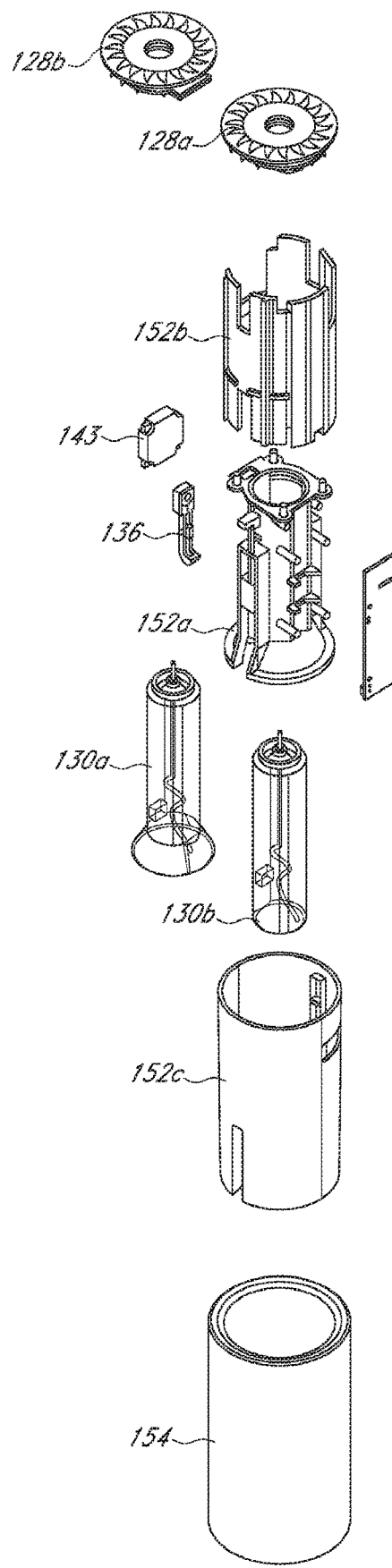
FIG. 6H is another exploded view of an embodiment of a Smart Candle Platform and System as disclosed in FIGS. 6-6F along with detailed call-out elements for enablement of the present disclosure.

FIG. 6G is an exploded view of a Smart Candle Platform and System 10 with the various electronic and operational components illustrated for application with the various embodiments disclosed throughout and particularly FIGS. 6-6F. FIG. 6H is another exploded view of an embodiment of a Smart Candle Platform and System 10 as disclosed in FIGS. 6-6F along with detailed call-out elements for enablement of the present disclosure. As shown, the top cover 110 may be configured with either igniter 128 assembly with retractable igniter wires 129 or a standard igniter 128 assembly with optional scent pan 111. The single piece support frame 152a is configured to engage with the extinguisher fan 143, the quick release refill retention 136, the cartridge 130 and the protective cover 152b. The cartridge 130 may be configured as a standard burn time interchangeable refill cartridge or as an extended burn time interchangeable refill cartridge. (See FIG. 20 and supporting disclosure therein) The shell support 152c for decorative outer shell 151 is positioned between the protective cover 152b and the outer shell 151. The outer shell 151 may be decorative, fixed or interchangeable and may be made from various materials, without any limitation and/or restriction unless otherwise indicated in the following claims.

Figure 7A:
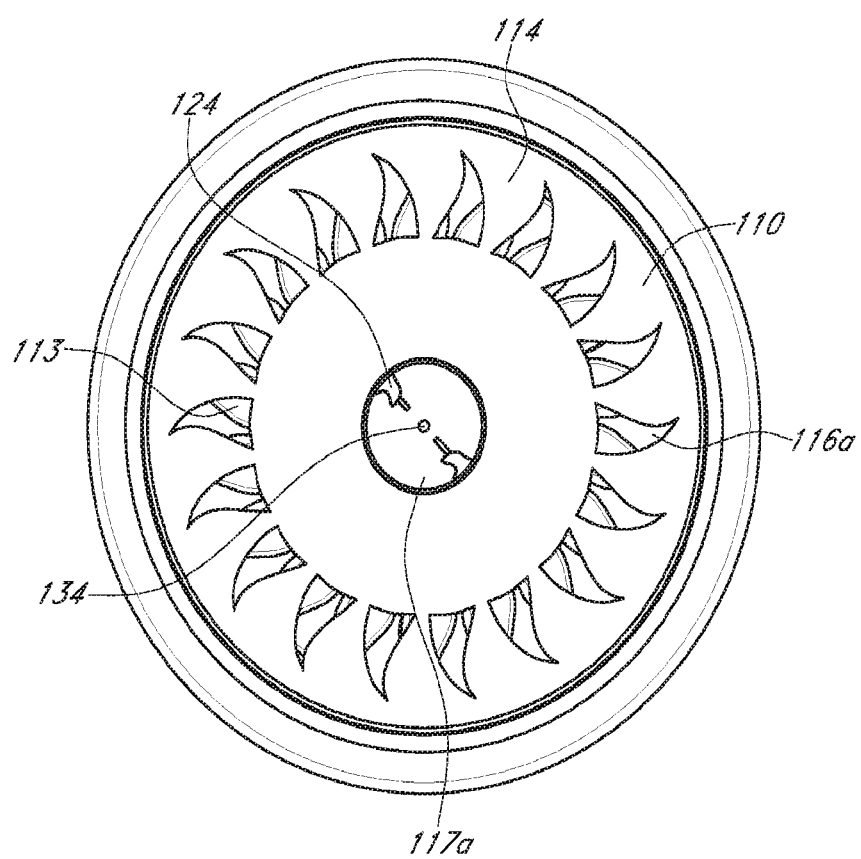
Figure 7B:
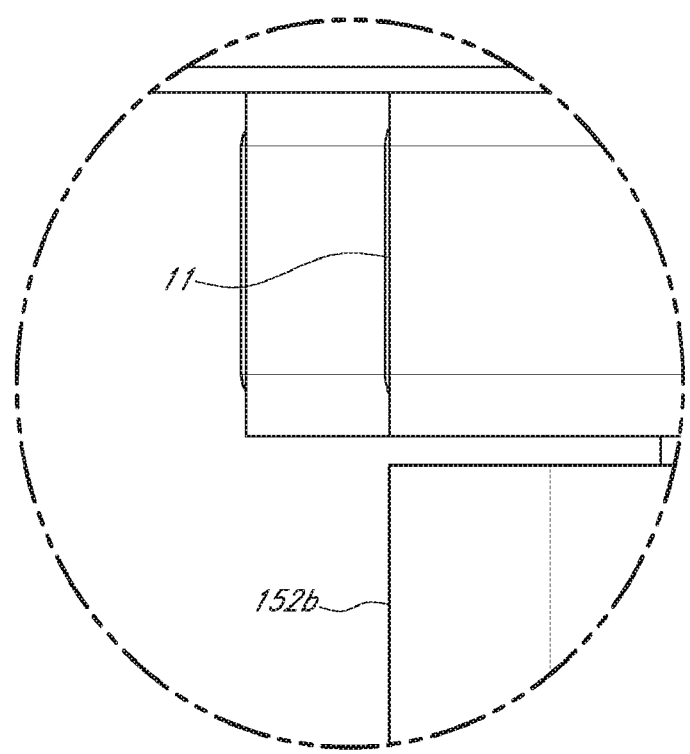
FIG. 7B is a side view of the scent pan as disclosed in FIG. 7A.

FIG. 7A is a top perspective view of the decorative scent pan cover 114 with scent twist adjustment as disclosed while FIG. 7B is a side view of the scent pan 111 as disclosed in FIG. 7A. As shown, the scent pan system may be configured with a scent pan cover 114 with scent level twist adjustment, the scent pan 111 and the scent ring 113. The scent pan 111 is positions at the upper portion of the protective cover 152b of the inner cover 152 and proximate the top cover aperture 117. Dependent on the particular purpose and/or season (holiday), the scent pan cover 114 may be customized and decorative with different images, colors, designs, sizes and shapes without any limitation and/or restriction. The scent ring 113 is positioned in the scent pan 111 and underneath the scent pan cover 114. The dual prong ignition system 120 may be positioned proximate to a wick 134 to generate the flame when activated. The heat of the living flame 100 activates the distribution of the fragrance or the scent of the scent ring 113. As shown, the scent ring 113 is shown in semi-closed position which facilitates the distribution of fragrance or scent (also see FIGS. 8-8F and supporting discussion herein).

Figure 7C:
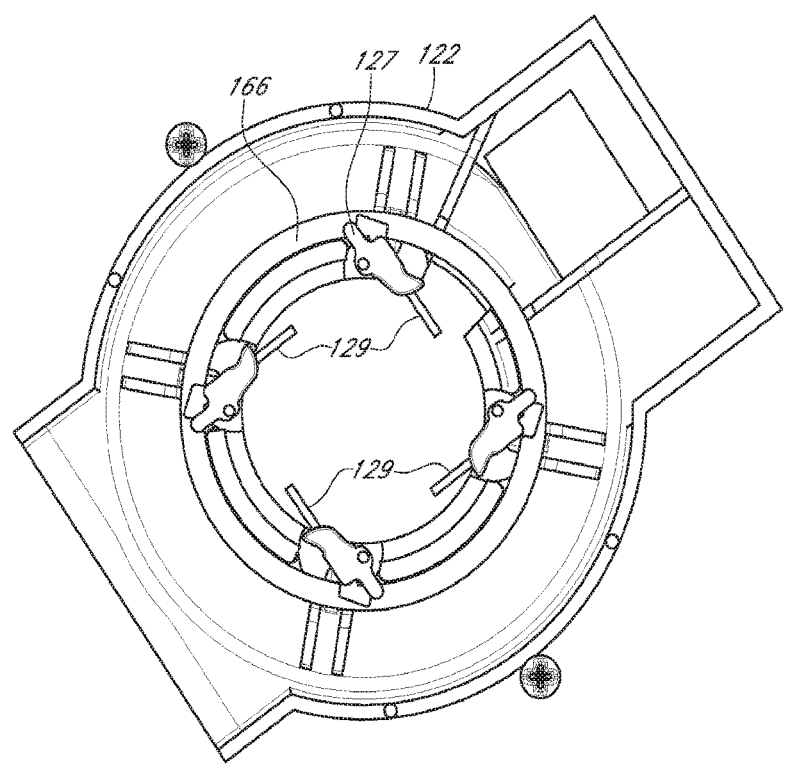
FIG. 7C is a top perspective view of an igniter of a Smart Candle Platform and System with the scent pan cover removed wherein the igniter positions on top of the cartridge and underneath the scent pan as shown and disclosed herein.

FIG. 7C is a top perspective view of an igniter of a Smart Candle Platform and System 10 with the scent pan cover 114 removed wherein the ignitor 128 is positioned on top of the cartridge 130 and underneath the scent pan 111 as shown and disclosed herein. The ignition system 120 is configured with an ignitor 128, an igniter support frame 122, an igniter finger(s) 127, a pivoting cam for indexing of igniters 128 and an igniter wire 129. The ignition system 120 is electronically controlled. In another embodiment, the ignition system 120 is electronically connected to a battery 148 positioned proximate the support frame 152a. The ignitor 128 is positioned proximate the wick 134 and is coupled to the ignition system 120.

Figure 8A:
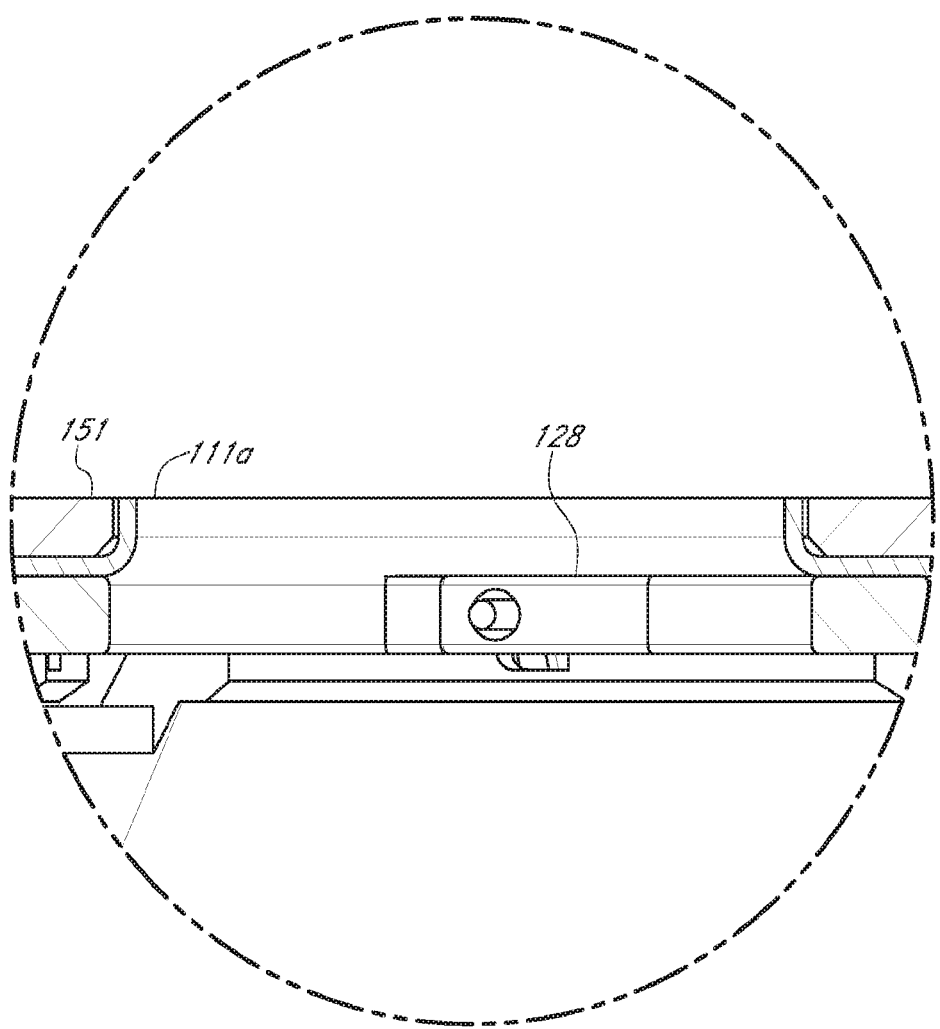
FIGS. 8A and 8D are cross-sectional views of the decorative scent pan having the protective cover on the top of the embodiment.
Figure 8B:
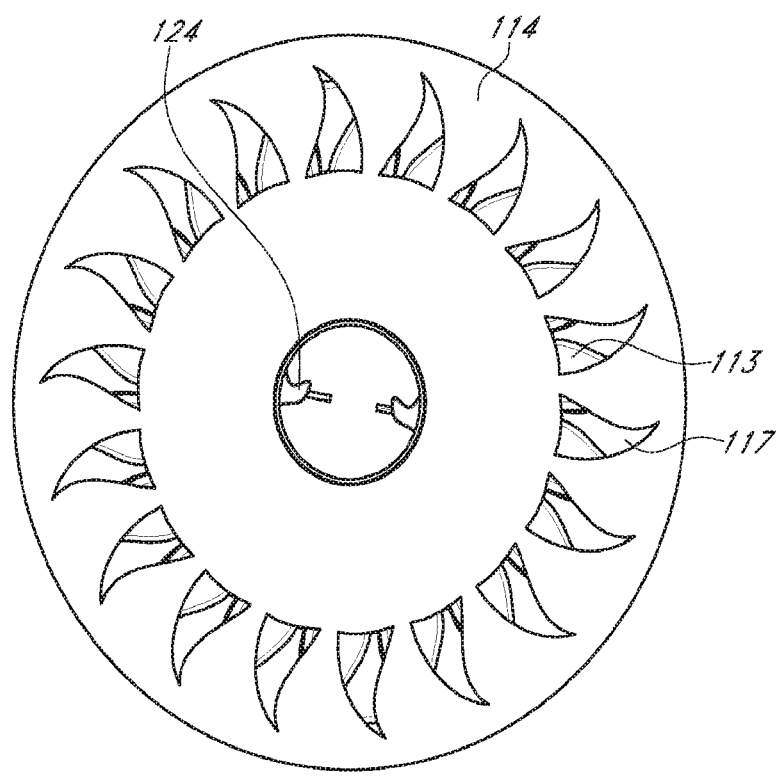
Figure 8C:
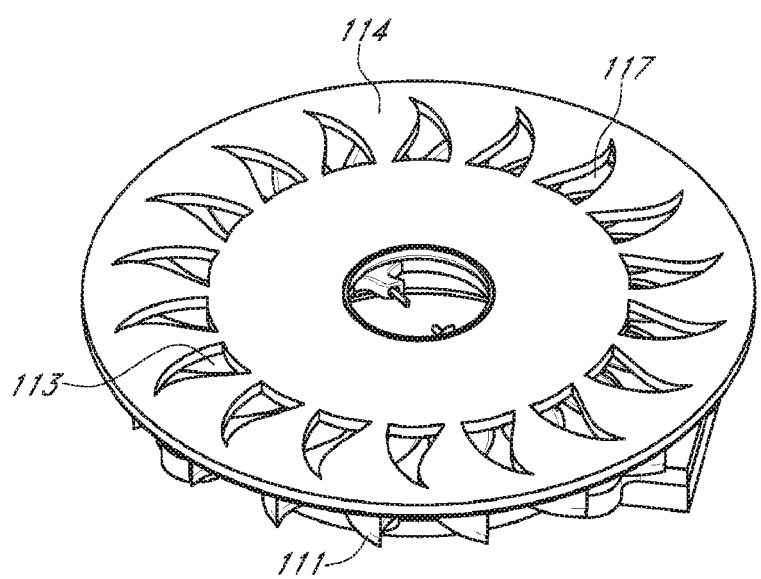
FIG. 8C is a top perspective view of a scent pan of a Smart Candle Platform and System.
Figure 8D:
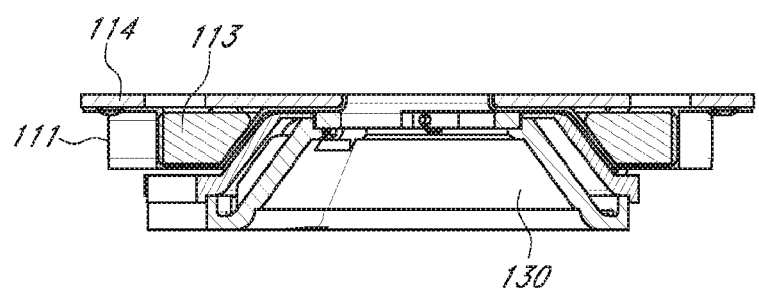
Figure 8E:
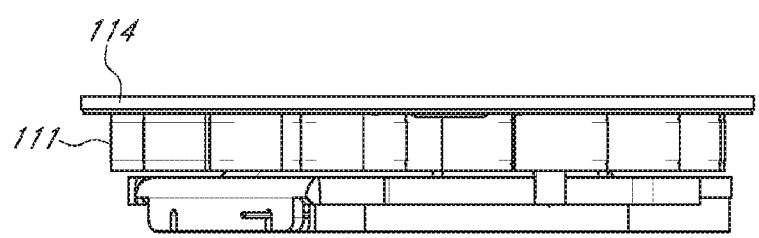
FIG. 8E is a side perspective view of a scent pan as disclosed herein.
Figure 8F:
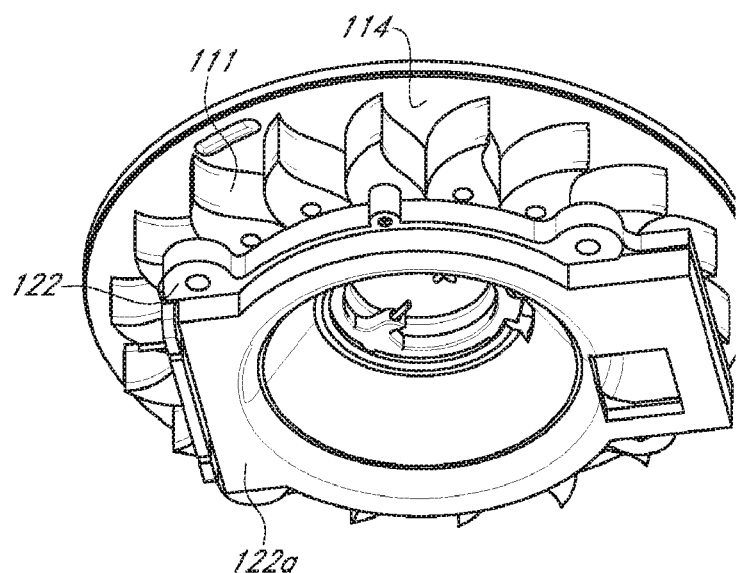

FIG. 8 is a perspective view of a Smart Candle Platform and System 10 having a scent pan 111 as disclosed wherein FIGS. 8A and 8D are cross-sectional views of the decorative scent pan 111 having the scent pan cover 114 on the top of the ignitor frame 122. FIG. 8B is a front view of a 10 of a decorative scent pan 111 while FIG. 8C is a top perspective view of a scent pan 111 of a Smart Candle Platform and System. FIG. 8F is a bottom perspective view of a scent pan 111 of a Smart Candle Platform and System 10 while FIG. 8E is a side perspective view of a scent pan 111 as disclosed herein. The scent pan system is configured with a scent pan cover 114, a scent pan 111 and a scent ring 113 as illustrated in detailed in FIGS. 8-11F.

Figure 9A:
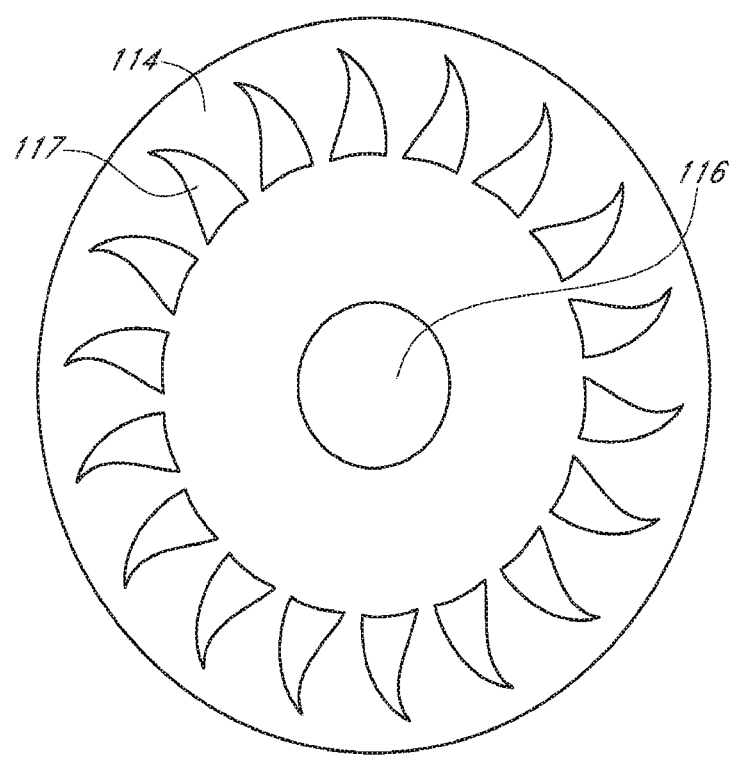
Figure 9B:
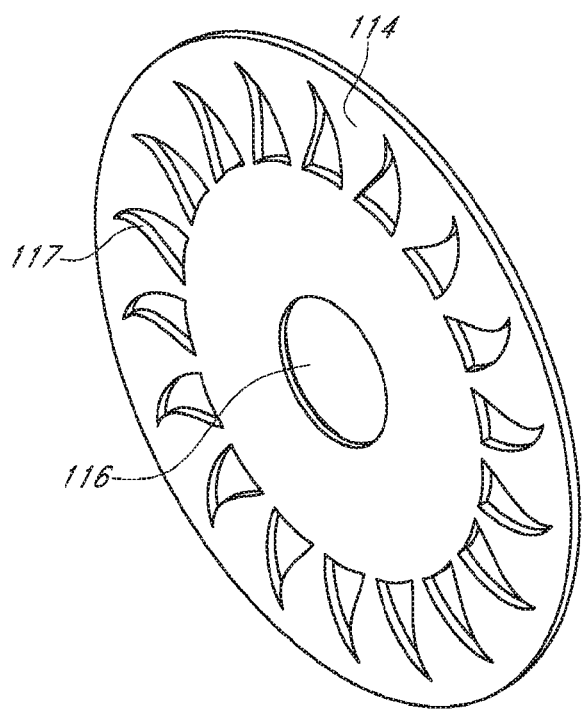
Figure 9C:
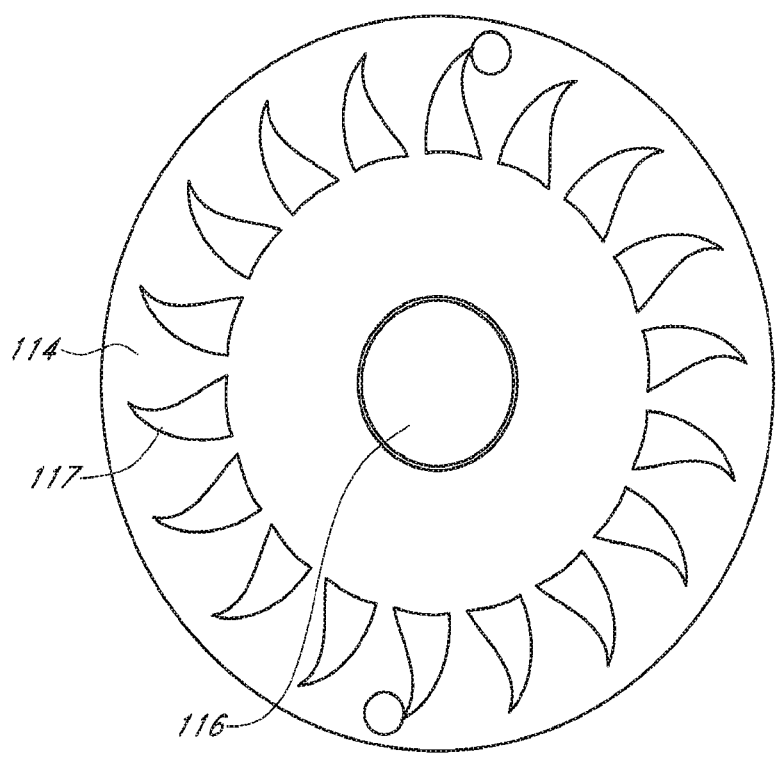
FIG. 9C is a back view of a decorative pan cover of a Smart Candle Platform.
Figure 9D:
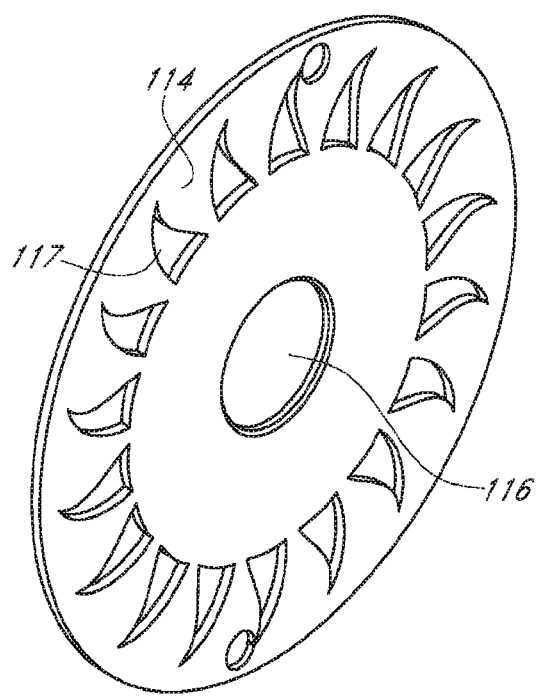
FIG. 9D is a bottom perspective view of a decorative pan cover of a Smart Candle Platform and System as disclosed herein.

FIG. 9A is a front view of a decorative pan cover 114 of a Smart Candle Platform and System 10 while FIG. 9C is a back view of a decorative pan cover 114 of a Smart Candle Platform. FIG. 9B is a top perspective view of a decorative pan cover 114 of a Smart Candle Platform and System 10 while FIG. 9D is a bottom perspective view of a decorative pan cover 114 of a Smart Candle Platform and System 10 as disclosed herein. As shown, the scent pan cover 114 may be configured with multiple apertures 117a which serve the purpose of decoration and distribution of the scent. One of ordinary skill will appreciate the design of the scent pan cover 114 and the arrangement of the apertures 117a as disclosed is not limited to a particular design as shown and may be configured to maximize the effectiveness scent delivered and the amount of scent distributed.

Figure 10A:
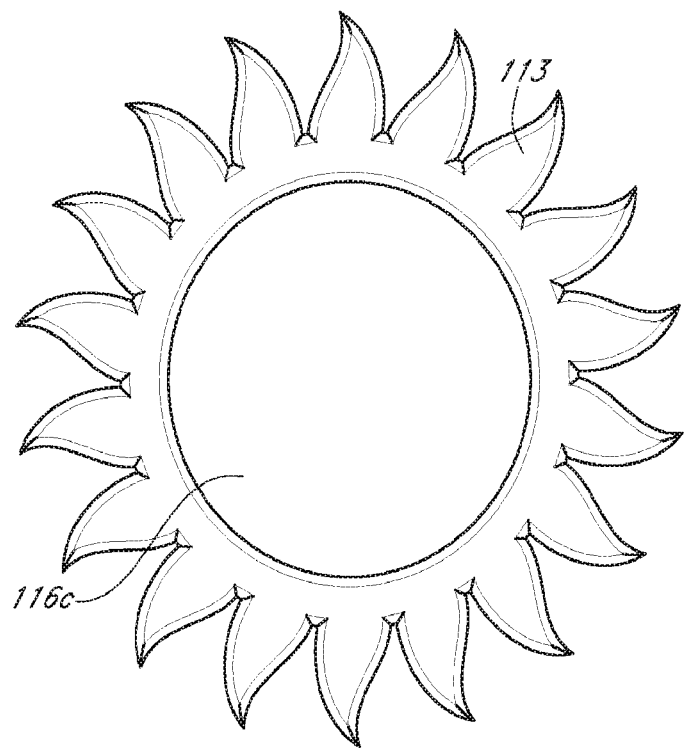
Figure 10B:
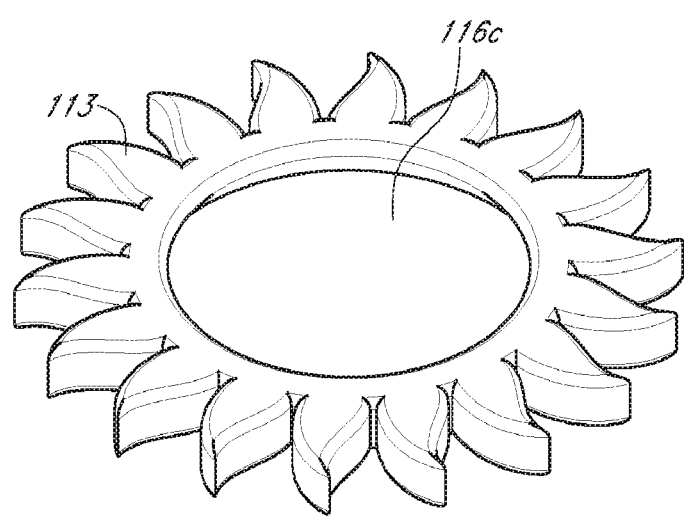
Figure 10C:
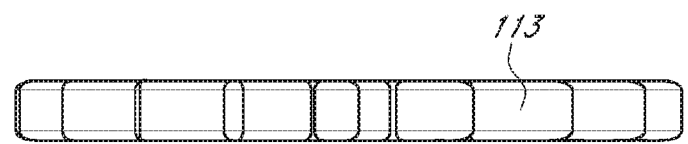
FIG. 10C is a side view of a molded scent ring of a Smart Candle Platform as disclosed herein.
Figure 10D:
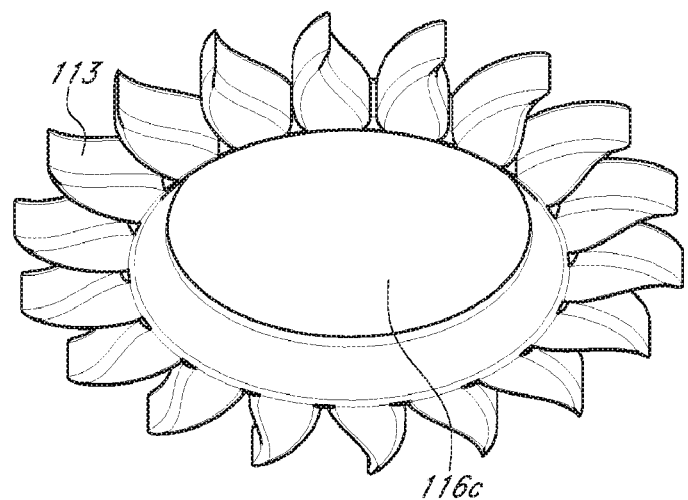
FIG. 10D is a side bottom perspective of a molded scent ring of a Smart Candle Platform as disclosed herein.

FIG. 10A is a front view of a molded scent ring 113 of a Smart Candle Platform and System 10 while FIG. 10C is a side view of a molded scent ring 113 of a Smart Candle Platform and System 10 as disclosed herein. FIG. 10B is a top perspective view of a molded scent ring 113 of a Smart Candle Platform and System 10 while FIG. 10D is a side bottom perspective of a molded scent ring 113 of a Smart Candle Platform as disclosed herein. Each scent ring 113 has different scent or fragrance and may be customized as needed. The scent ring 113 is interchangeable and replaceable with ease. One of ordinary skill will appreciate that the scent ring 113 is not melted at high temperature (flame temperature) which allows the scent ring 113 to be reused multiple times. The scent ring 113 may be customized in size, shape, color and fragrance to match with the scent pan 111 and the scent pan cover 114 without any limitation and/or restriction unless otherwise indicated in the following claims.

Figure 11A:
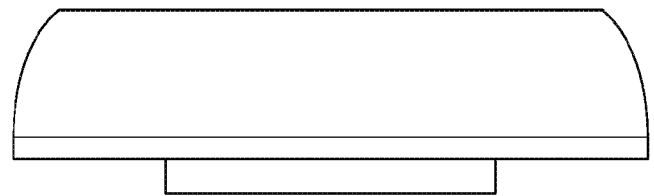
Figure 11B:
FIG. 11B is a cross-sectional view of a Smart Candle Platform and System as disclosed in FIG. 11A.
Figure 11C:
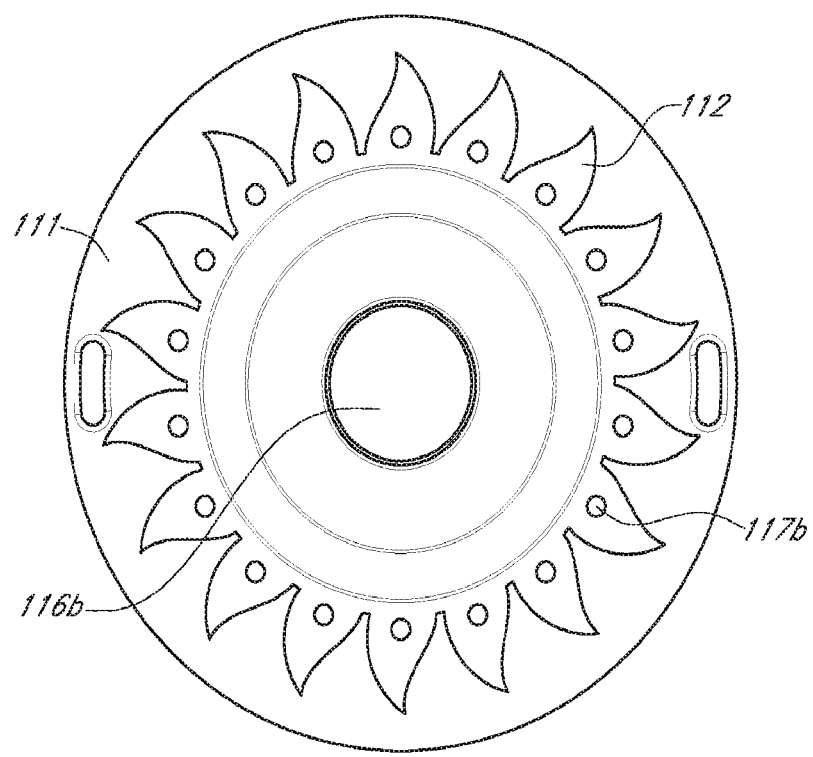
Figure 11D:
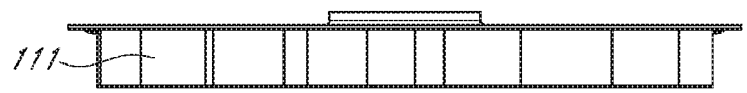
FIG. 11D is a side view of a Smart Candle Platform as disclosed herein.
Figure 11E:
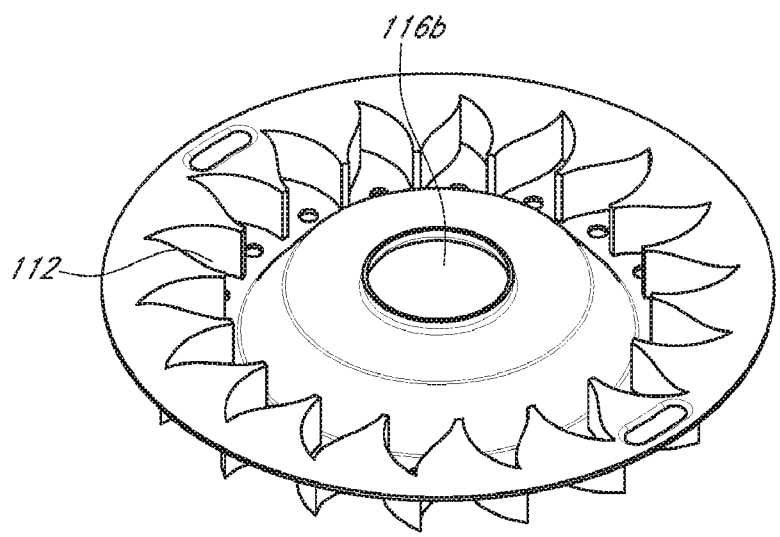
Figure 11F:
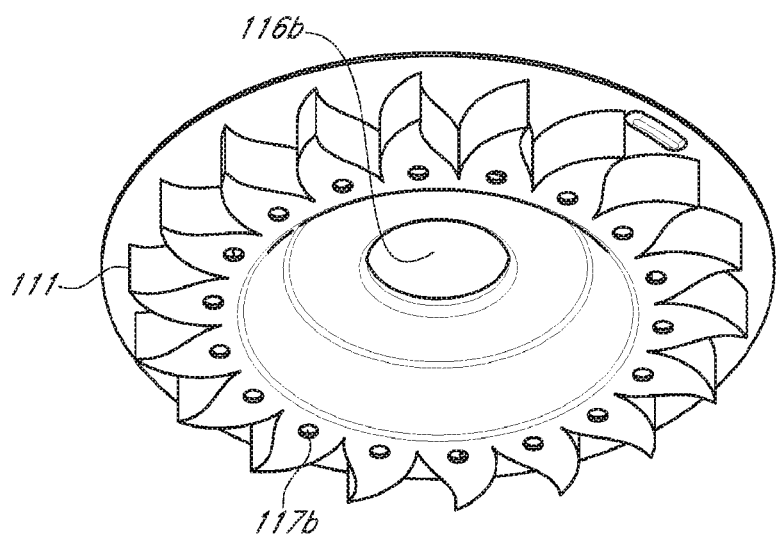
FIG. 11F is a bottom perspective view of a scent pan of a Smart Candle Platform and System in operation which embodies at some of the various features disclosed herein.

FIG. 11A is a side perspective view of a Smart Candle Platform and System 10 while FIG. 11B is a cross-sectional view of a Smart Candle Platform and System 10 as disclosed in FIG. 11A. FIG. 11C is a front view of a decorative scent pan 111 of the Smart Candle Platform and System 10 while FIG. 11D is a side view of the decorative scent pan 111 of the Smart Candle Platform and System 10 disclosed herein. FIG. 11E is a top perspective view of the decorative scent pan 111 of the Smart Candle Platform and System 10 while FIG. 11F is a bottom perspective view of the decorative scent pan 111 of the Smart Candle Platform and System 10 in operation which embodies some of the various features disclosed herein. As shown, the scent pan 111 is configured as a scent ring holder 112 which houses the scent ring 113 when in use. The scent pan 111 has multiple apertures 117b wherein the apertures 117b are configured for housing the scent ring 113. Dependent on the particular application, the scent pan 111 may be customized with different sizes, shapes, colors, etc. without any limitation and/or restriction.

Figure 12A:
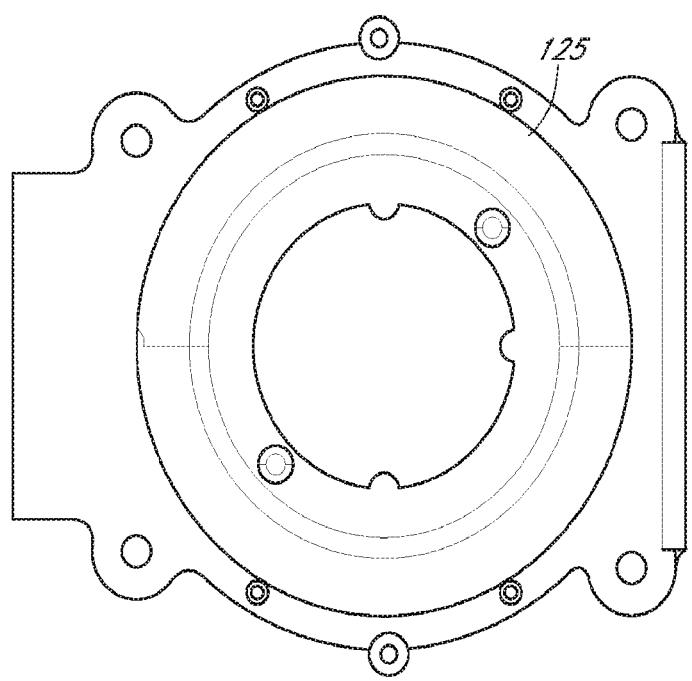
Figure 12B:
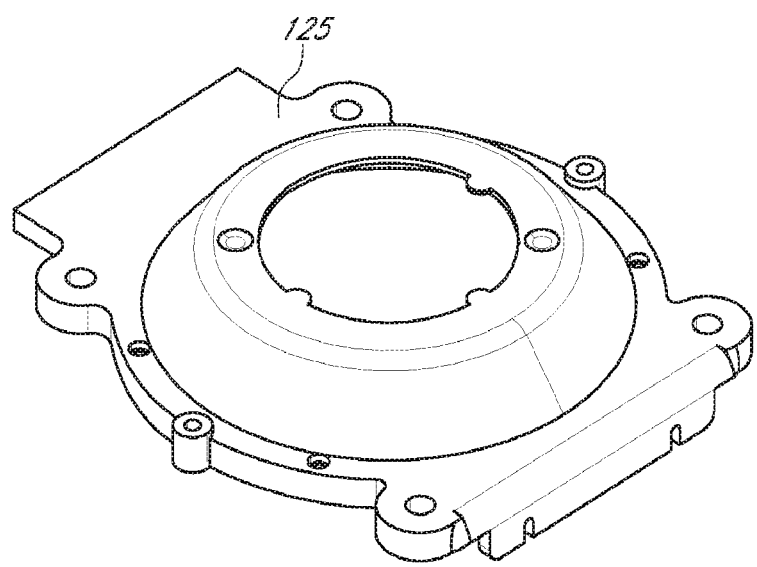
FIG. 12B is a bottom perspective view of an igniter cover of a Smart Candle Platform and System in operation which embodies at some of the various features disclosed herein.
Figure 12C:
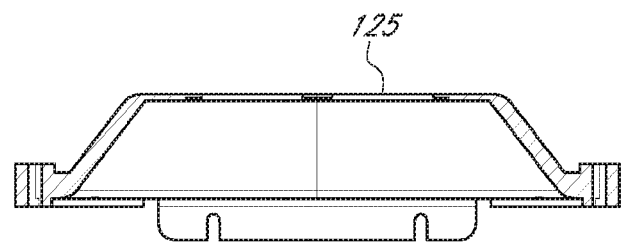
FIG. 12C is a cross-sectional of an igniter cover of a Smart Candle Platform and System as shown and disclosed in FIGS. 12A and 12B.
Figure 12D:
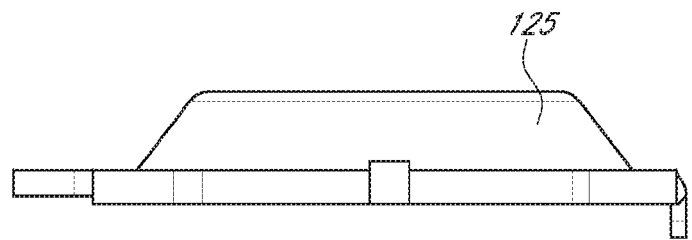
Figure 12E:
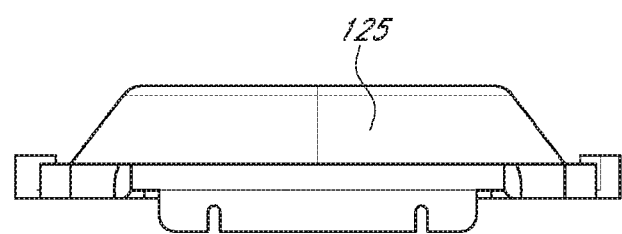
FIG. 12E is a right-side view of an igniter cover of a Smart Candle Platform as disclosed herein.

FIG. 12A is a top perspective view of an igniter cover 125 of a Smart Candle Platform and System 10 while FIG. 12B is a bottom perspective view of an igniter cover 125 of a Smart Candle Platform and System 10 in operation which embodies some of the various features disclosed herein. FIG. 12C is a cross-sectional view of an igniter cover of a Smart Candle Platform and System 10 as shown and disclosed in FIGS. 12A and 12B. FIG. 12D is a left-side perspective view of an igniter cover 125 of a Smart Candle Platform and System 10 while FIG. 12E is a right-side view of an igniter cover 125 of a Smart Candle Platform and System 10 as disclosed herein.

Figure 13A:
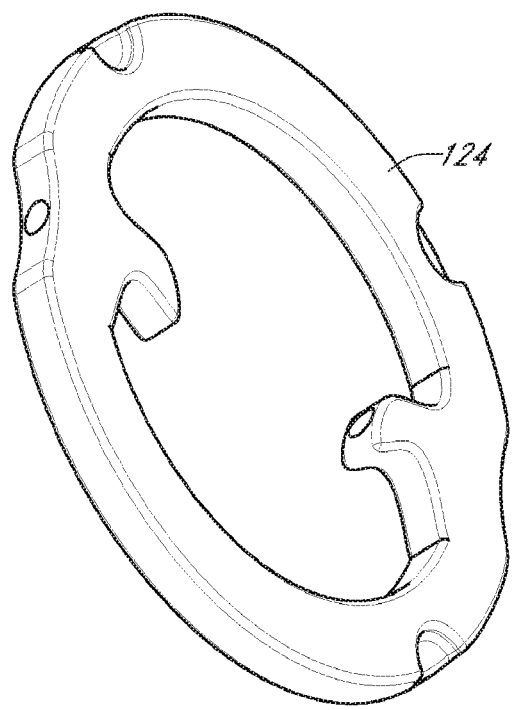
Figure 13B:
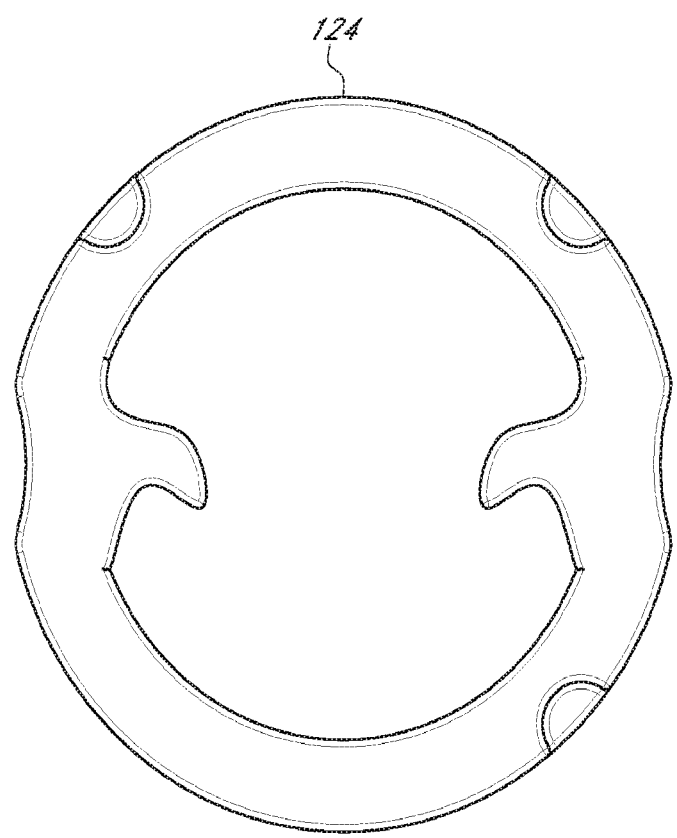
Figure 13C:
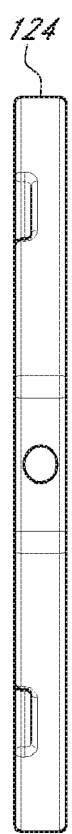
FIG. 13C is a side view of a 2-prong igniter of a Smart Candle Platform and System as disclosed herein.

FIG. 13A is perspective view of a two-prong igniter 124 of a Smart Candle Platform and System 10 while FIG. 13B is a front view of a two-prong igniter 124 of a Smart Candle Platform and System 10 while FIG. 13C is a side view of a two-prong igniter 124 of a Smart Candle Platform and System 10 as disclosed herein. As shown, the two-prong igniter 124 is positioned in the ignitor cover 125 and proximate to the wick 134.

Figure 14A:
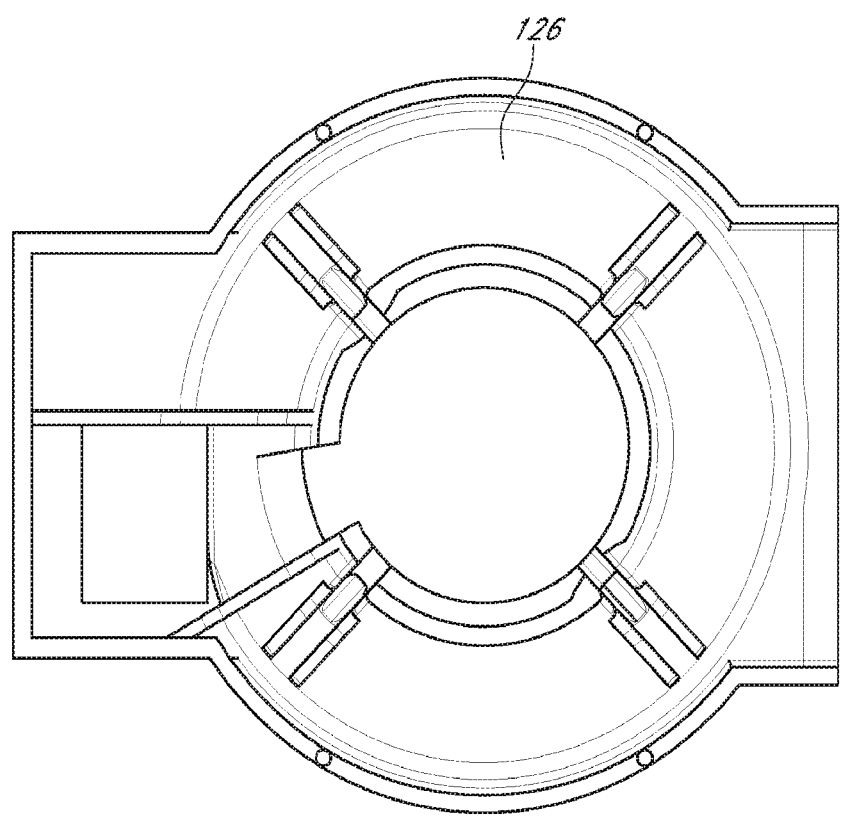
Figure 14B:
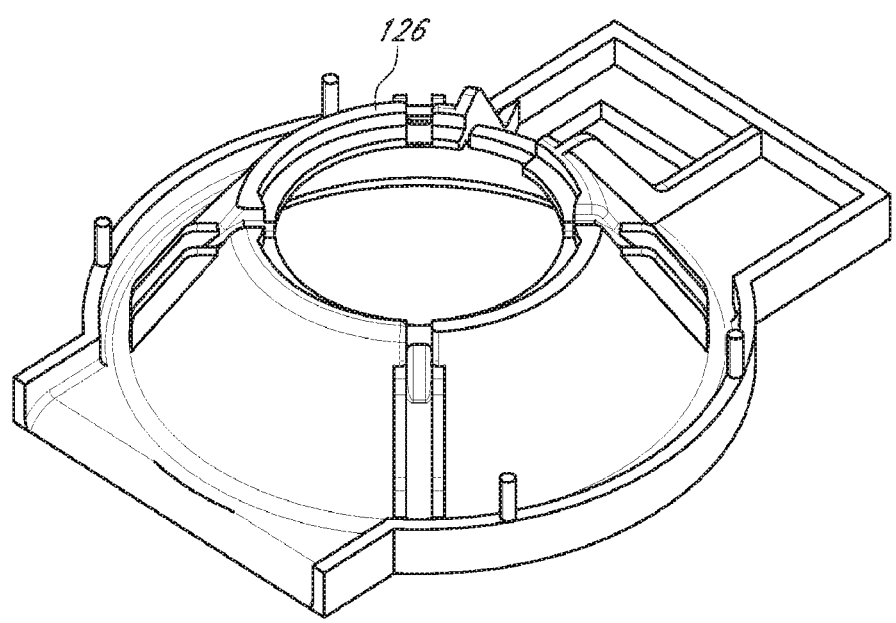
FIG. 14B is a bottom perspective view of an igniter base of a Smart Candle Platform and System in operation which embodies at some of the various features disclosed herein.
Figure 14C:
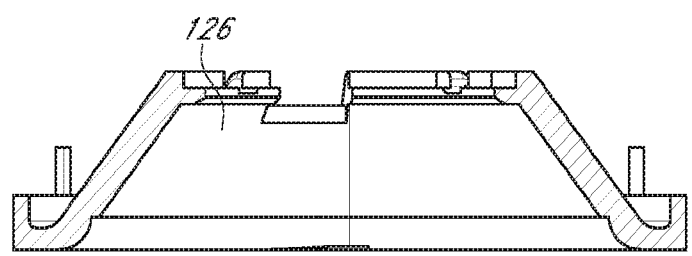
FIG. 14C is a cross-sectional of an igniter base of a Smart Candle Platform and System as shown and disclosed in FIGS. 14A and 14B.
Figure 14D:
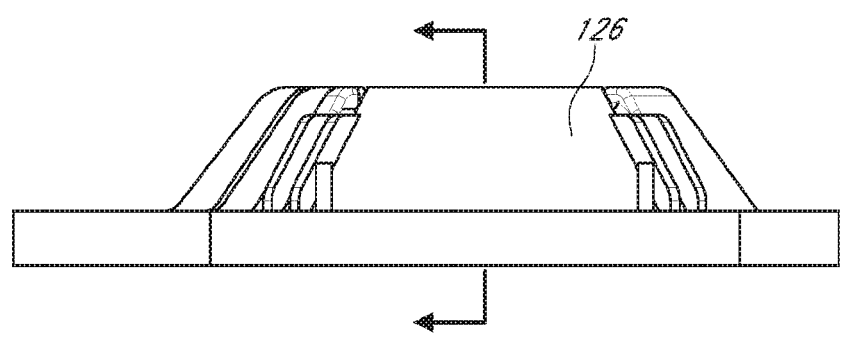
Figure 14E:
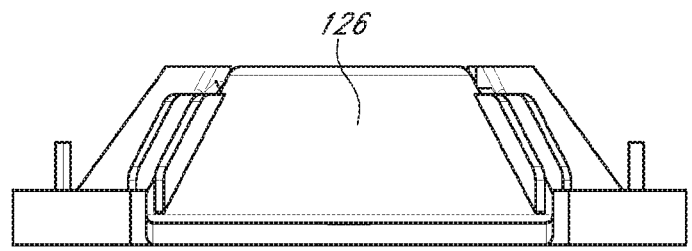
FIG. 14E is a right-side view of an igniter base of a Smart Candle Platform as disclosed herein.

FIG. 14A is a top perspective view of an igniter base 126 of a Smart Candle Platform and System 10 while FIG. 14B is a bottom perspective view of an igniter base 126 of a Smart Candle Platform and System 10 in operation which embodies some of the various features disclosed herein. FIG. 14C is a cross-sectional of an igniter base 126 of a Smart Candle Platform and System 10 as shown and disclosed in FIGS. 14A and 14B. FIG. 14D is a left-side perspective view of an igniter base 126 of a Smart Candle Platform and System 10 while FIG. 14E is a right-side view of an igniter base 126 of a Smart Candle Platform and System as disclosed herein.

Figure 15:
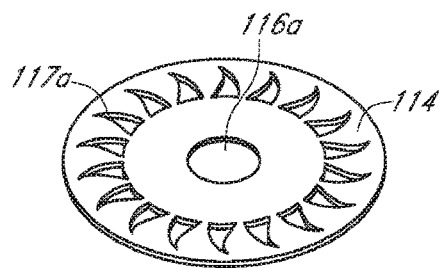
FIG. 15 is an exploded view of an upper end of a Smart Candle Platform and System providing various interworking components as shown and illustrated in FIGS. 9-14.
Figure 15:
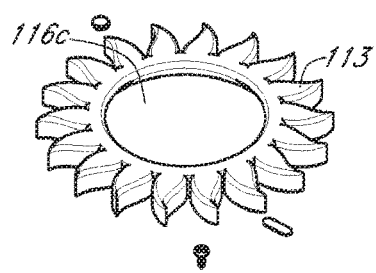
Figure 15:
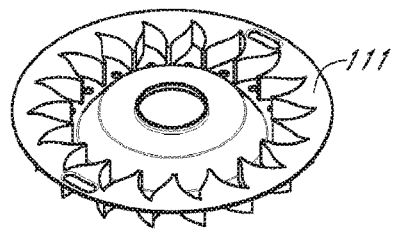
Figure 15:
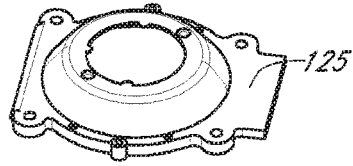
Figure 15:
Figure 15:
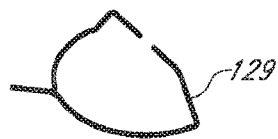
Figure 15:
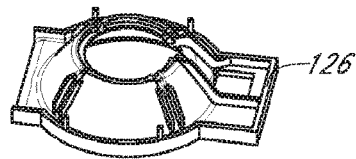
Figure 16:
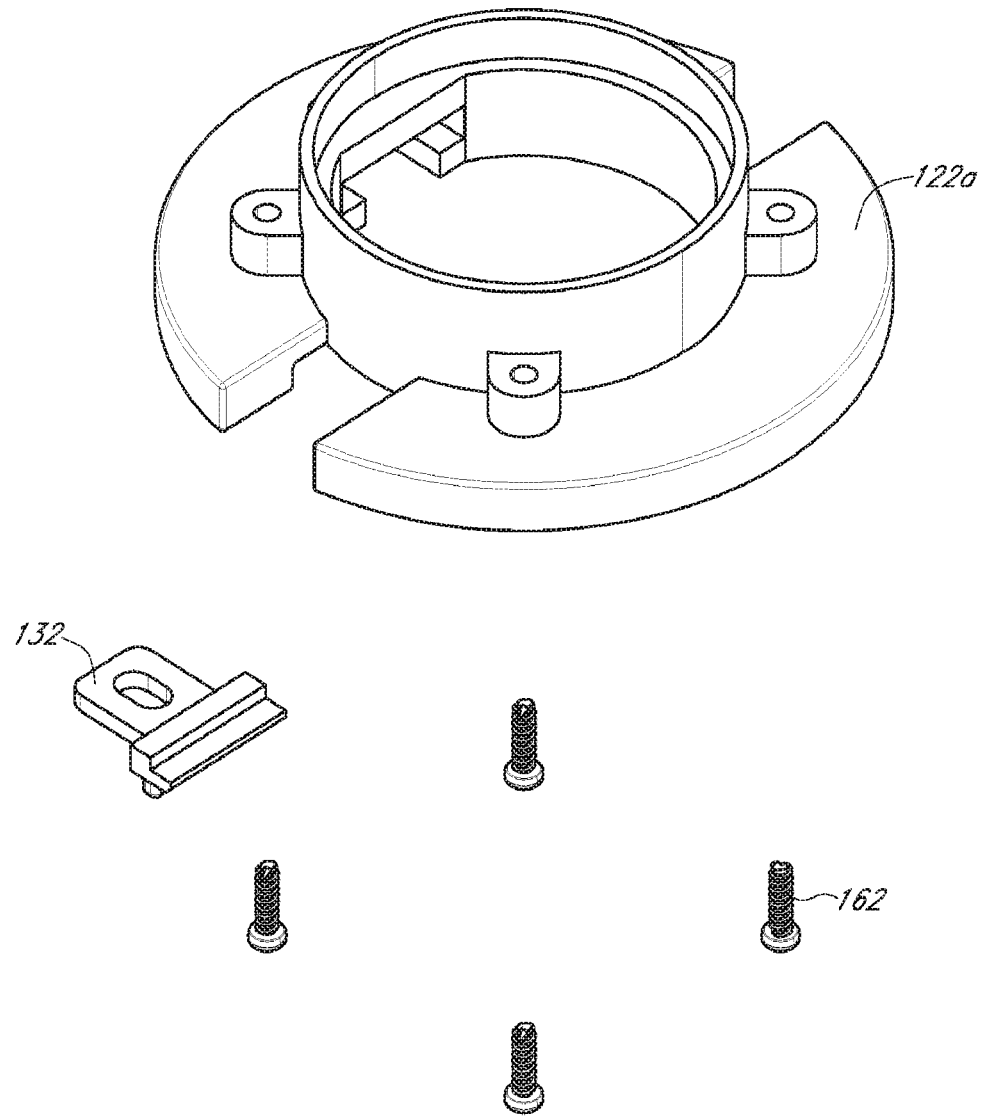
FIG. 16 is a perspective view of a Smart Candle Platform and System providing an ignitor top frame being secured to the embodiment via a refill lock and screw as disclosed herein.

FIG. 15 is an exploded view of an upper end of a Smart Candle Platform and System 10 illustrating the assembly of various components as shown and illustrated in FIGS. 9-14. As shown, in at least one embodiment, the scent pan cover 114 is positioned on top of the scent pan 111 wherein the scent ring 113 is positioned within the scent pan 111. The scent pan 111 as shown is positioned on top of the ignition system 120. The ignition system 120 is configured of an ignitor cover 125, a two-prong igniter 124, an ignitor wire 129 and an ignitor base 126. The two-prong igniter 124 and the ignitor wire 129 may be positioned between the ignitor cover 125 and the ignitor base 126 as shown, without restriction or limitation. FIG. 16 is a perspective view of an ignitor top frame support 122a which may be used with the embodiments disclosed in FIGS. 6-15 and secured to the support frame 152a via a refill lock 132 and screws 162 as disclosed herein.

Figure 17:
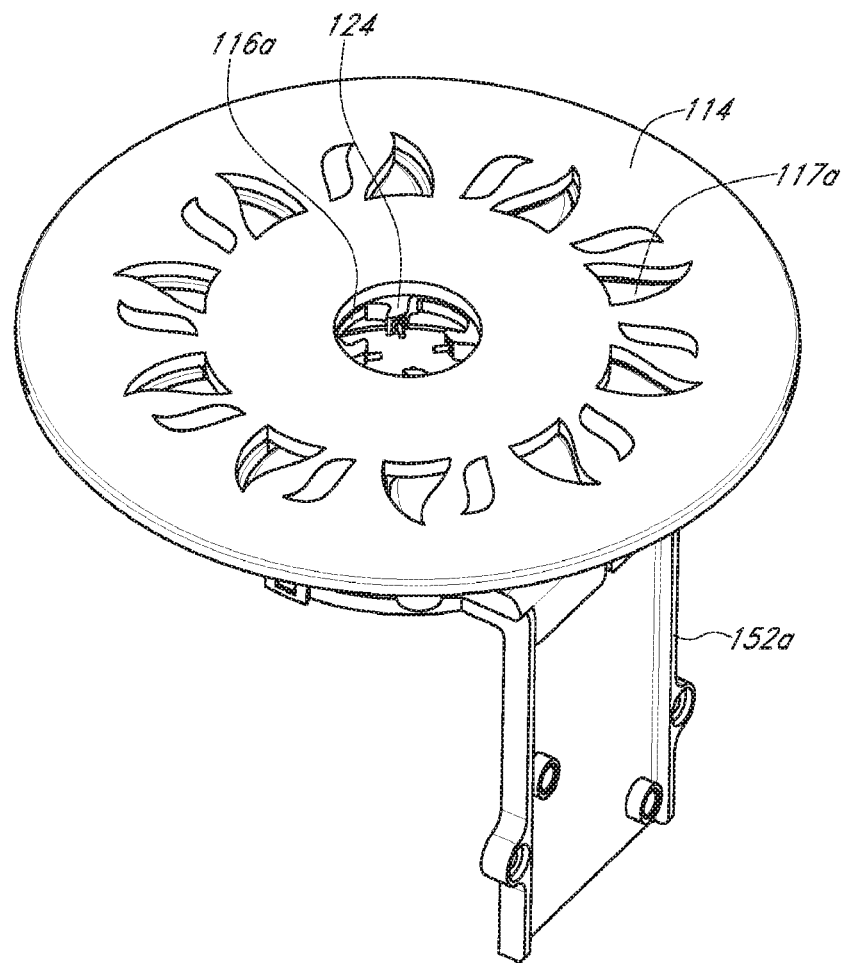
FIG. 17 is a perspective view of another embodiment of a Smart Candle Platform and System providing a scent pan affixed to a frame as disclosed herein.

FIG. 17 is a perspective view of a scent pan cover 114 having apertures 117a around the periphery. FIG. 17 also illustrates the position of the ignitor prongs 124 positioned around the periphery of the opening 116 positioned in the center of the scent pan cover and scent pan (116a, 116b) with the scent pan 111 affixed to the support frame 152a as disclosed herein.

Figure 18:
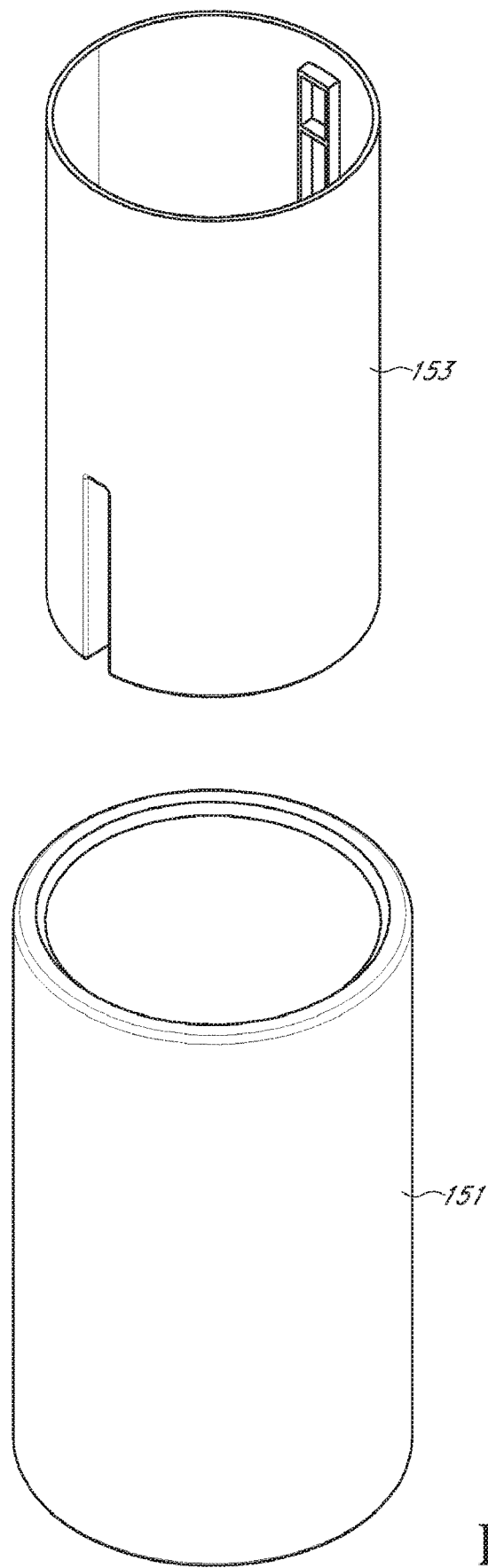
FIG. 18 is an exploded view of a Smart Candle Platform and System illustrating the shell support and the outer shell wherein the shell support positions within the outer shell.
Figure 19:
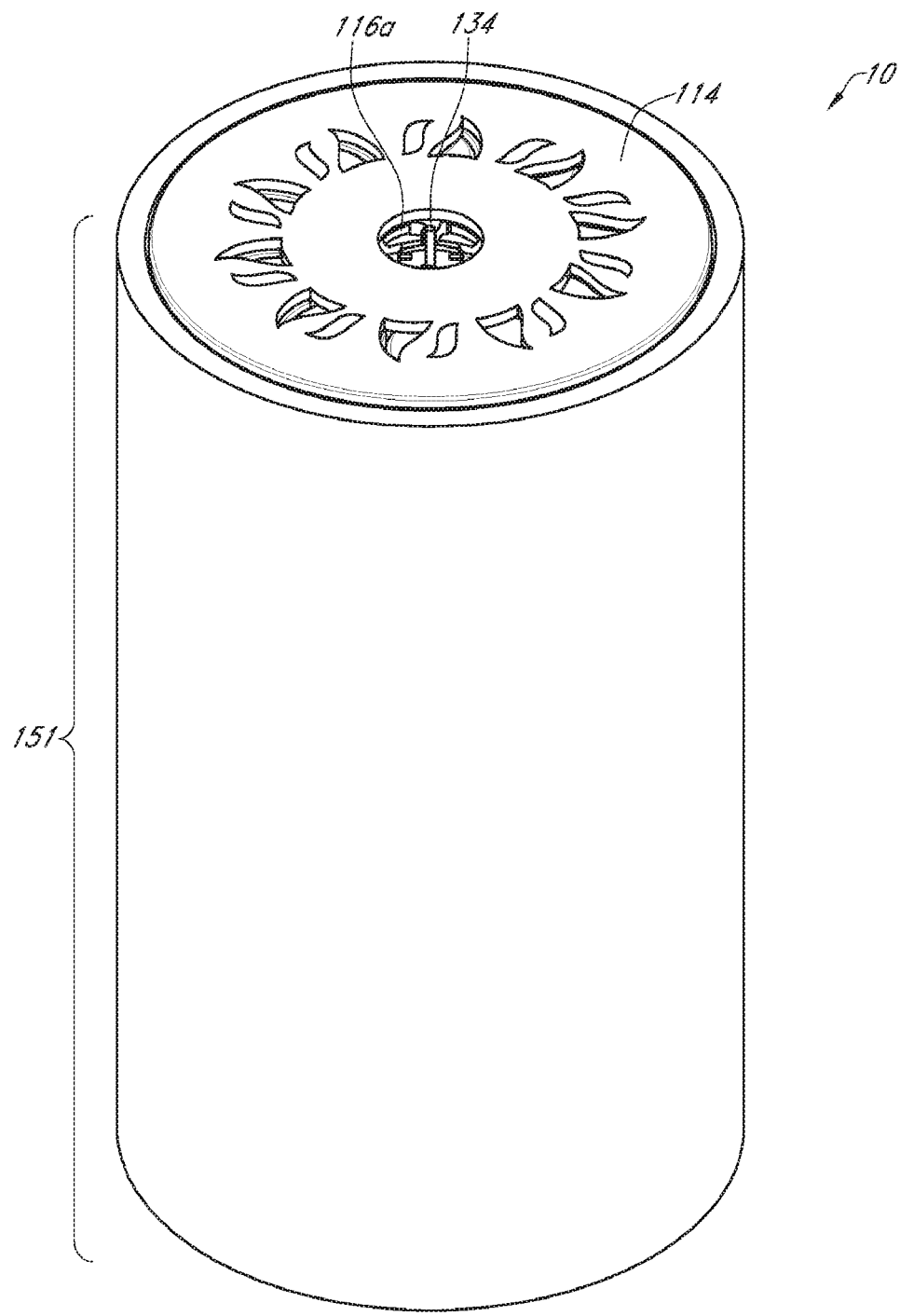
FIG. 19 is a perspective view of a Smart Candle Platform and System providing a wick positioned in the cartridge with an exposed portion extending from an upper end of the cartridge as shown and disclosed herein.

FIG. 18 is an exploded view of a Smart Candle Platform and System 10 illustrating the shell support 152c and the outer shell 151 wherein the shell support 152c is positioned within the outer shell 151. FIG. 19 is a perspective view of a Smart Candle Platform and System 10 providing a wick 134 positioned in the fuel source cartridge 130 with an exposed portion extending from an upper end of the cartridge 130 as shown and disclosed herein.

Figure 20A:
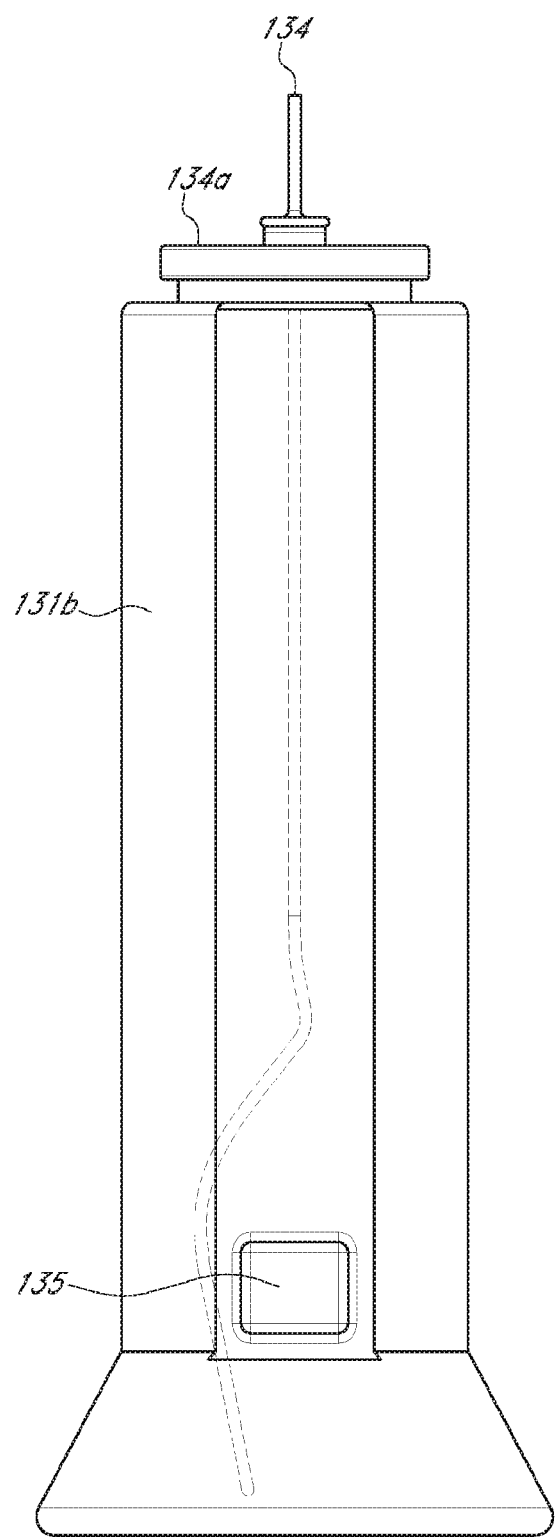
Figure 20B:
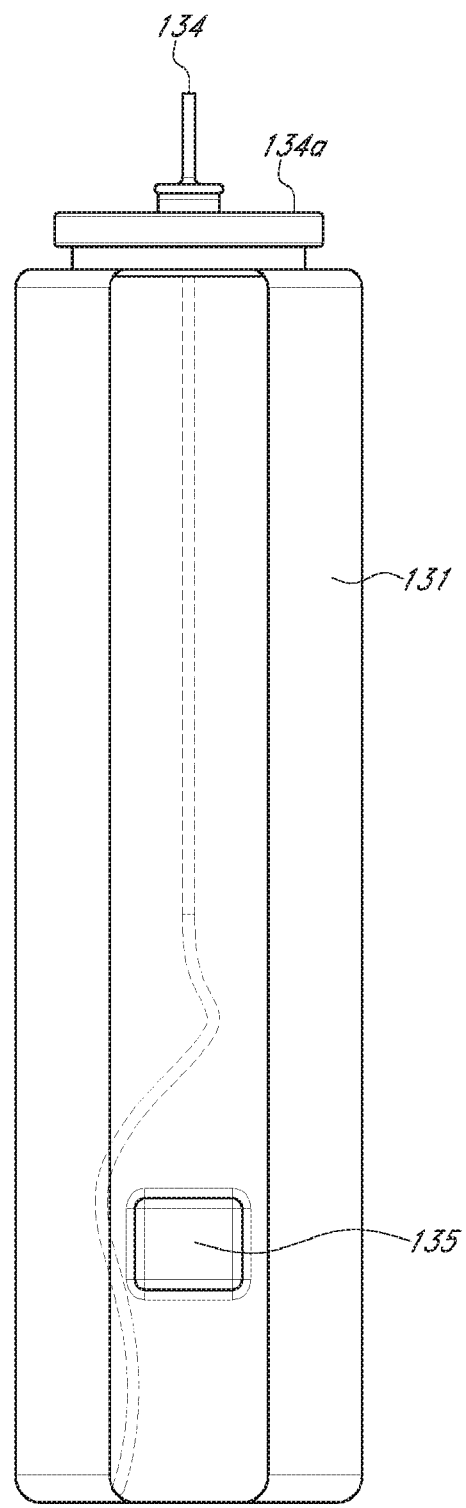
FIG. 20B is a standard burn refill bottle as disclosed herein.

In another aspect of the disclosed embodiment, the cartridge (refill bottle) 130 is illustrated in FIGS. 20A and 20B. As shown, FIG. 20 is a perspective view of a Smart Candle Platform and System 10 providing two different types of cartridges 130 as shown in FIGS. 20A and 20B. FIG. 20A is a perspective of an extended burn refill bottle 131a while FIG. 20B is a standard burn refill bottle 131b as disclosed herein. The cartridge 130 is configured with a retention groove 135 to facilitate removal and replacement from the support frame 152a. When the user presses the push button 156 on the inner cover 152, the push button 156 is extended against the retention groove 135 which releases the cartridge 130 therein. Both extended burn re-fill cartridge 131a and standard burn re-fill cartridge 131b are configured with a wick 134 and a support cap 134a, a custom quick release cartridge retention groove 135 and a base 137. However, the base 137 of extended burn re-fill cartridge 131a is relatively larger than the base 137 of the standard burn re-fill cartridge 131b which allow the bottle or the container 131 to hold more fuel (or oil) 133. Dependent on the particular application, the fuel material 133 may be an essential oil, but not limited to a solid paraffin wax, a liquid paraffin, a soy, a veggie, a fatty acid, and/or combinations thereof without any limitation and/or restriction. In addition, the wick 134 may be positioned in the cartridge 130 with an exposed portion of the wick 134 extending from an upper end of the cartridge 130 which allows the flame 100 to be above the top cover 110 and also allows the cartridge 130 to supply the fuel 133 when in use for supporting living flame 100.

Figure 21:
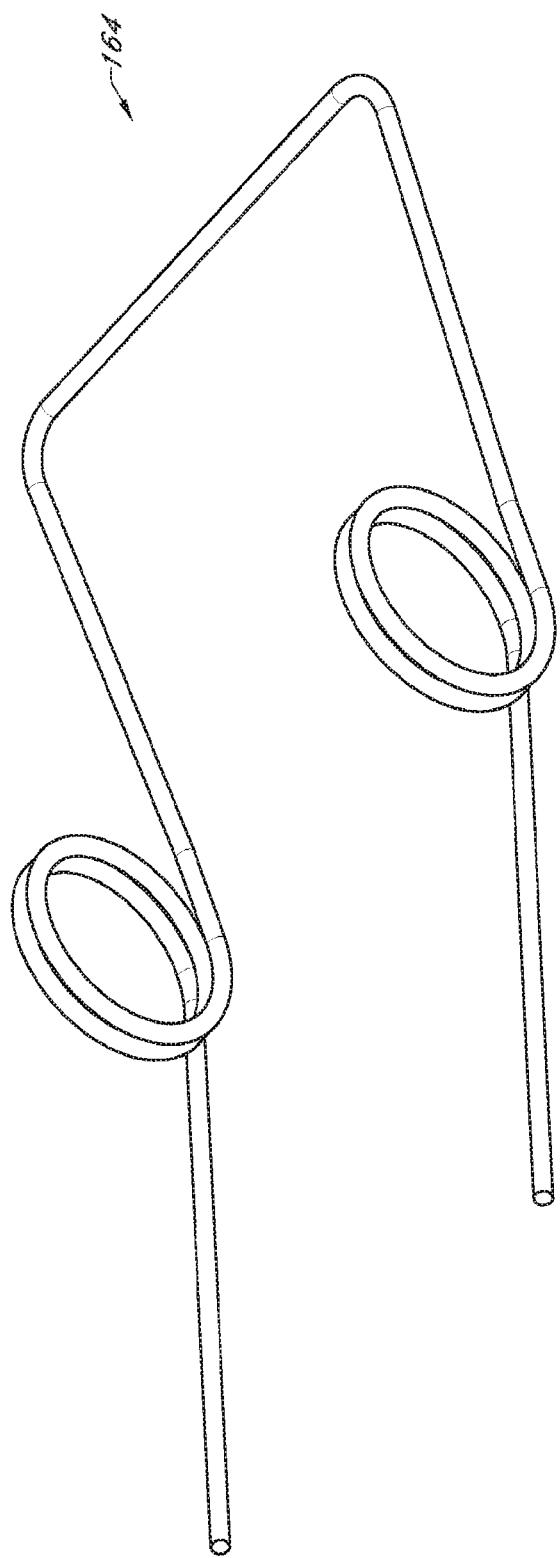
FIG. 21 is a perspective view of a spring of a Smart Candle Platform and System as shown herein.
Figure 21A:
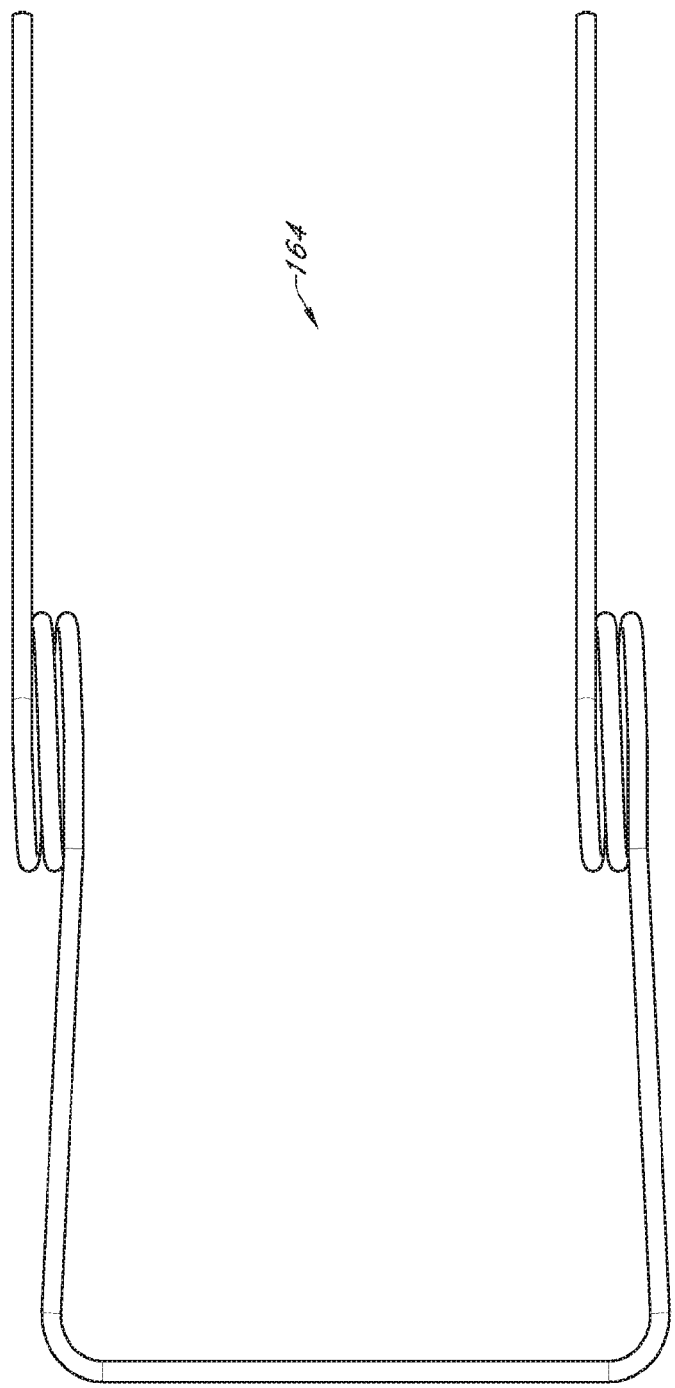
FIG. 21A is another perspective view of a spring of a Smart Candle Platform and System as shown in FIG. 21.

In another aspect of the disclosed embodiment, a spring 164, a retention bracket 161 and the mid-frame 3j are shown and disclosed in FIGS. 21-24. FIG. 21 is a perspective view of a spring 164 of a Smart Candle Platform and System 10 as shown herein. FIG. 21A is another perspective view of the spring 164 of a Smart Candle Platform and System 10 as shown in FIG. 21. As shown, the spring 164 has a first end and a second end wherein both the first and the second end are coiled and foldable. One of ordinary skill will appreciate that dependent on the particular application, the shape and/or size of the spring 164 may be customized or different type of springs 164 may be used and replaced to maximize the effectiveness of a Smart Candle Platform and System 10, without any limitation and/or restriction unless otherwise indicated in the following claims.

Figure 22:
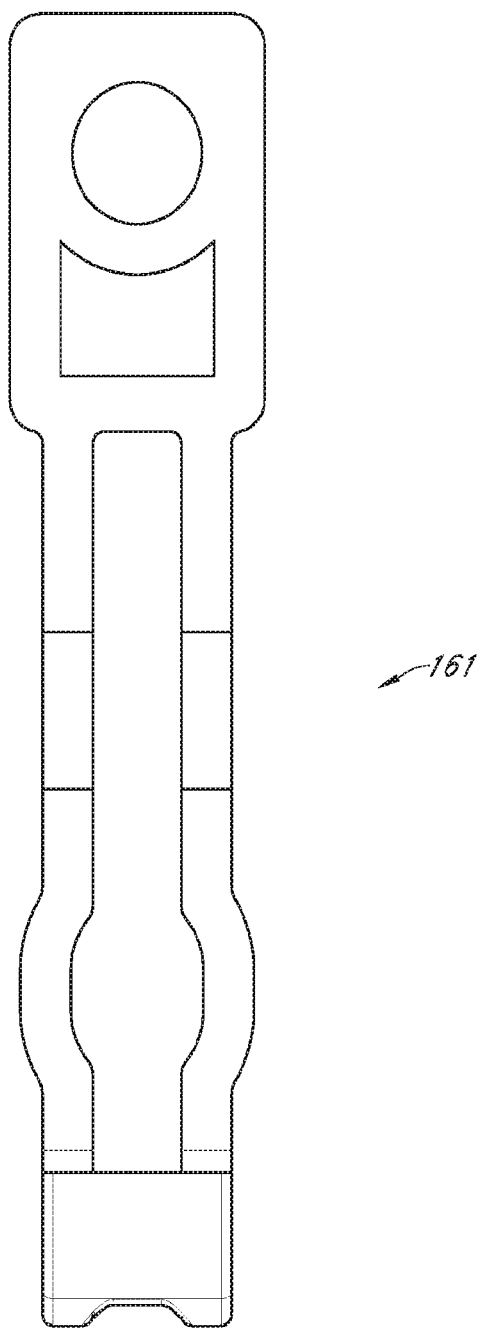
FIG. 22 is a perspective view of a Smart Candle Platform and System providing a retention bracket as shown and disclosed herein.
Figure 22A:
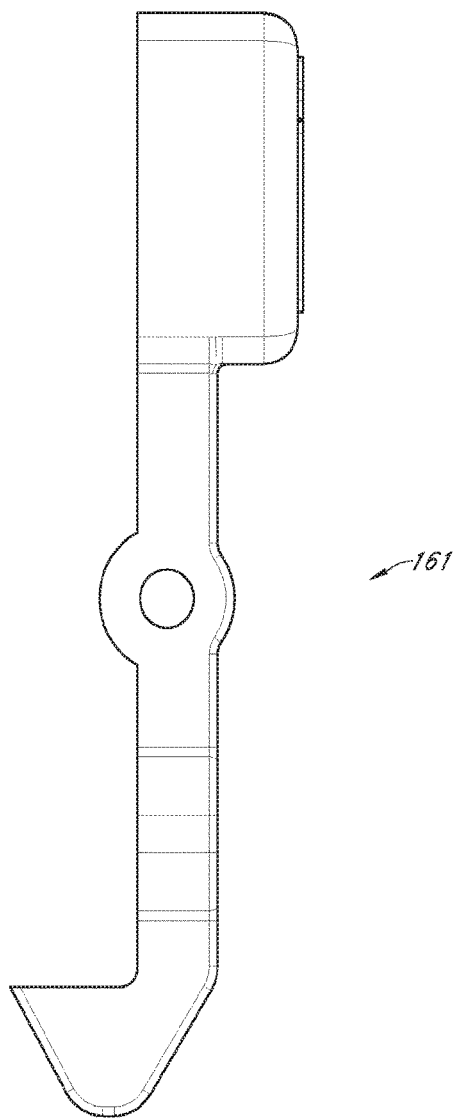
FIG. 22A is a cross-section view of a Smart Candle Platform and System having a retention bracket as shown in FIG. 22.
Figure 23:
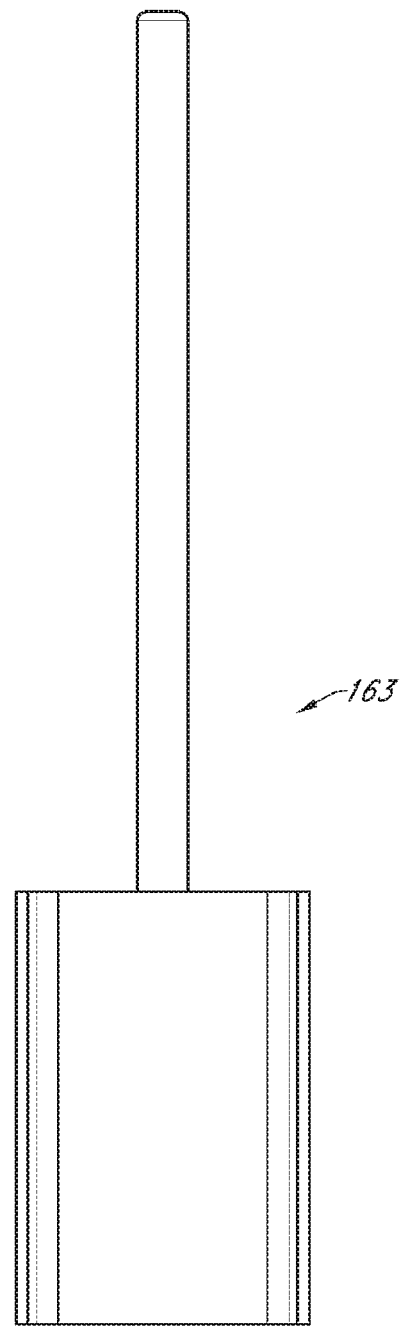
FIG. 23 is a perspective view of a Smart Candle Platform and System providing a push cam as shown and disclosed herein.

FIG. 22 is a perspective view of a Smart Candle Platform and System 10 providing a retention bracket 161 as shown and disclosed herein. FIG. 22A is a cross-section view of a Smart Candle Platform and System 10 having a retention bracket 161 as shown in FIG. 22. FIG. 23 is a perspective view of a Smart Candle Platform and System 10 providing a push cam 163 as shown and disclosed herein.

Figure 24:
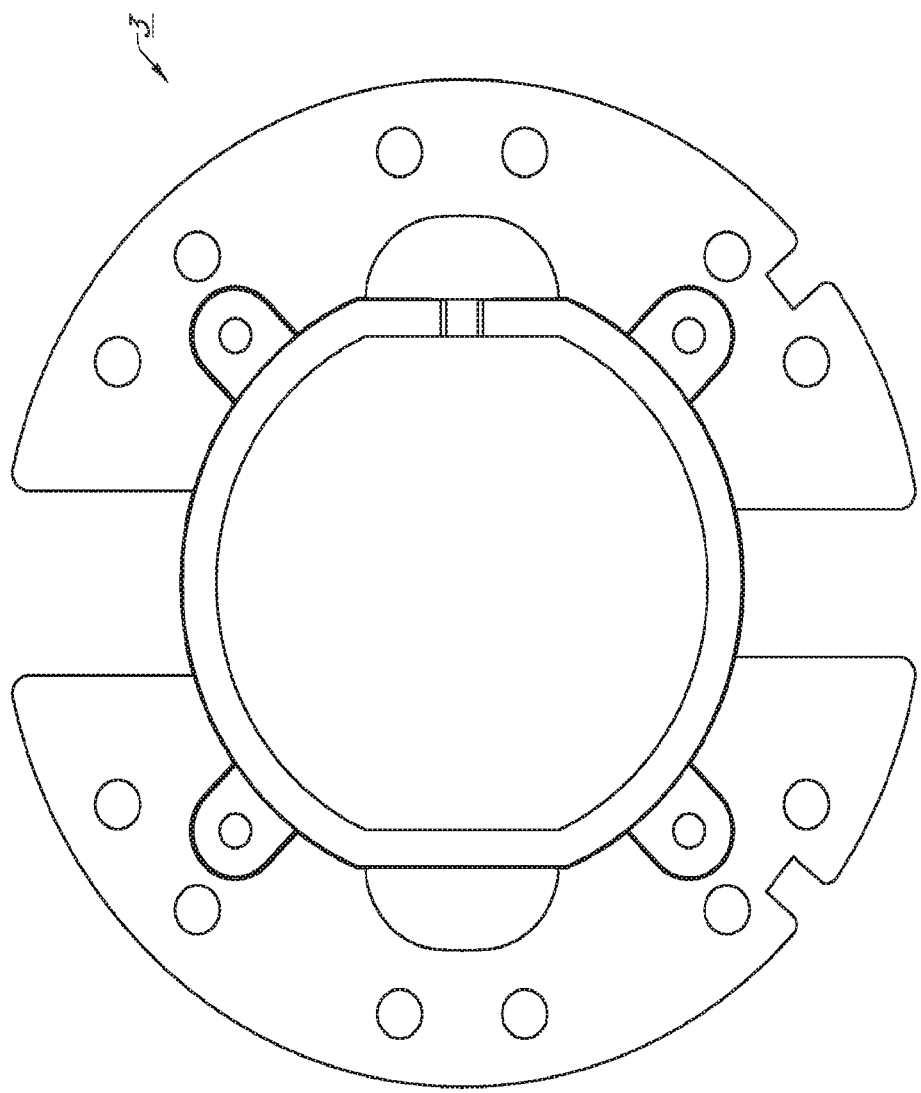
FIG. 24 is a top perspective view of a midframe base of a Smart Candle Platform and System as shown and disclosed herein.
Figure 24A:
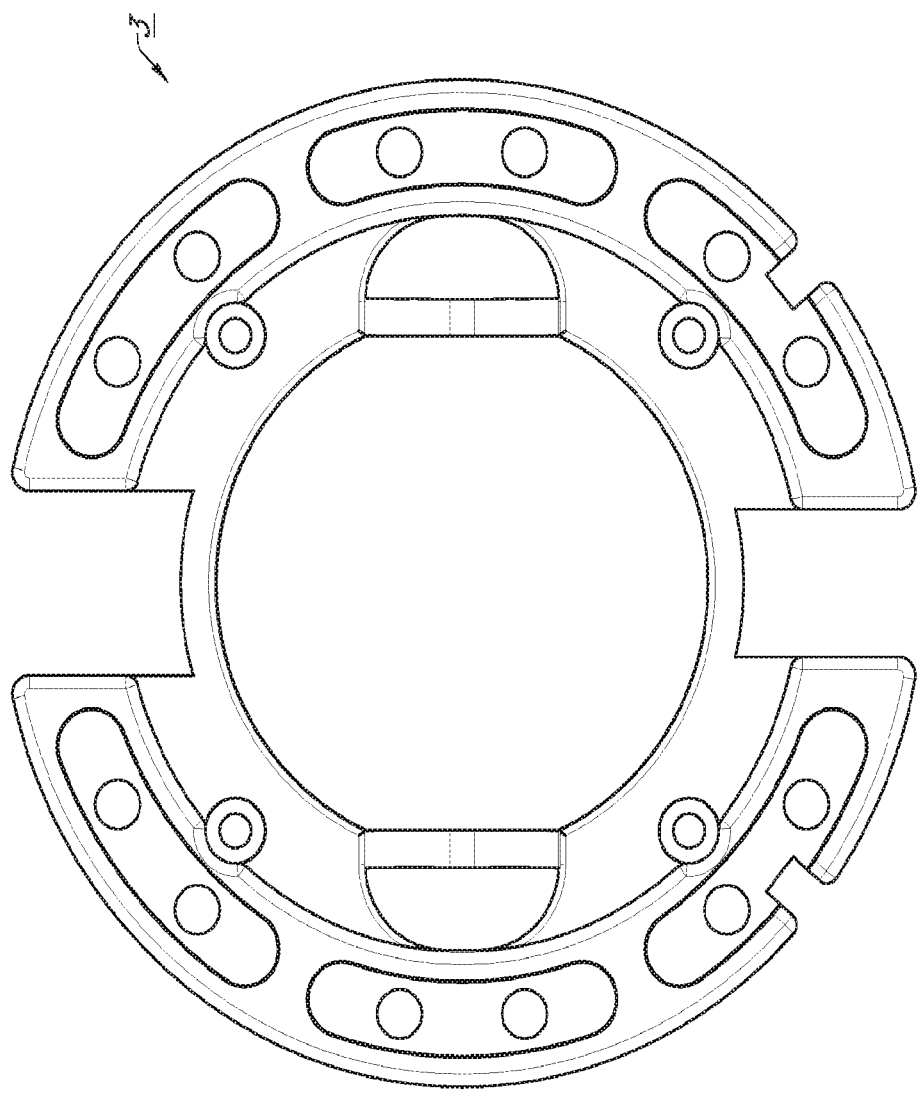
FIG. 24A is bottom perspective view of a midframe base of a Smart Candle Platform and System as shown as in FIG. 24.

In another aspect of the disclosed embodiment, FIG. 24 is a top perspective view of a mid-frame base 3j of a Smart Candle Platform and System 10 as shown and disclosed herein. FIG. 24A is bottom perspective view of a mid-frame base 3j of a Smart Candle Platform and System 10 as shown in FIG. 24.

Figure 25:
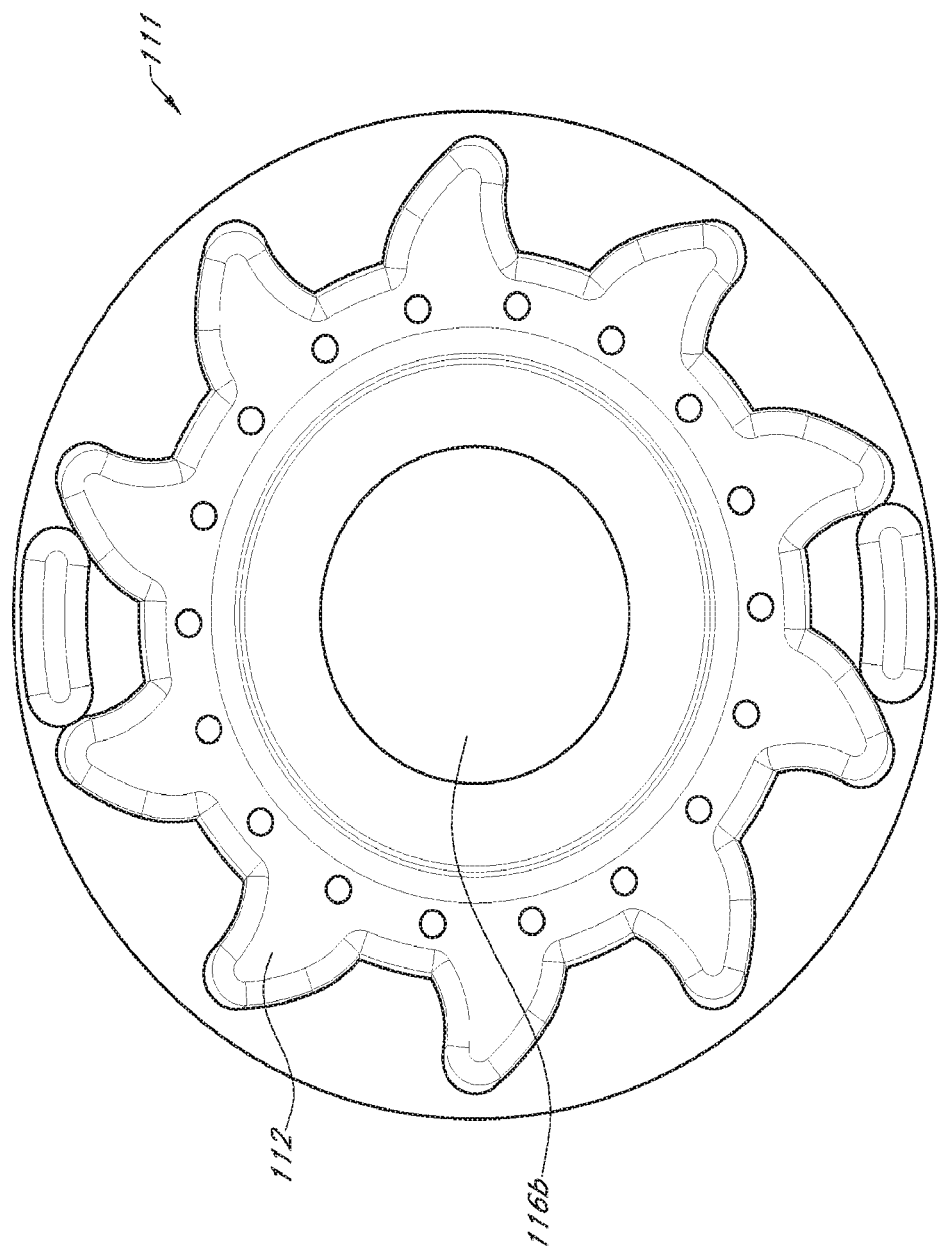
FIG. 25 is a perspective view of a scent ring pan of a Smart Candle Platform and System as shown and disclosed herein.
Figure 26:
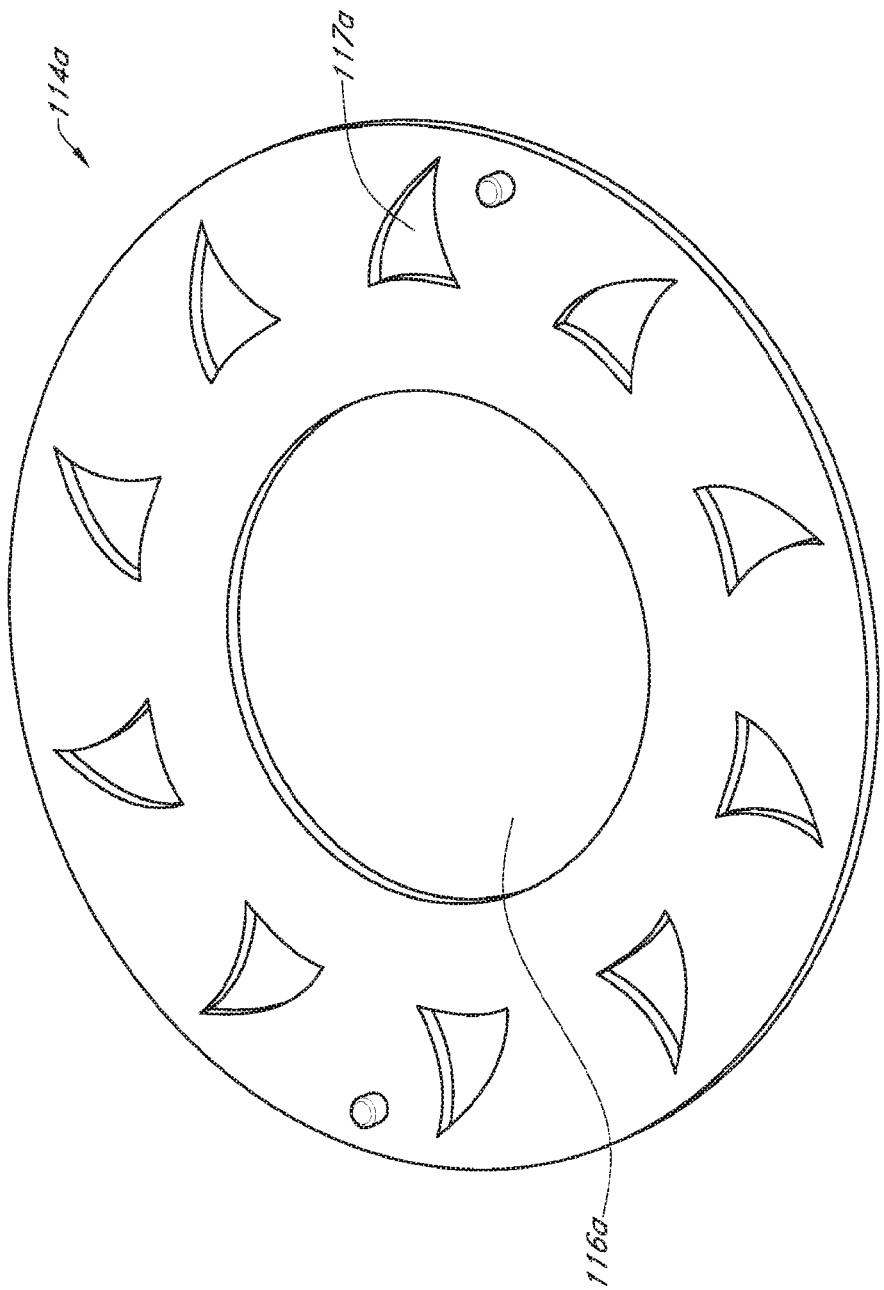
FIG. 26 is a perspective view of a Smart Candle Platform and System providing a scent top cover with hole positioned on top of the scent ring in FIG. 25.
Figure 27:
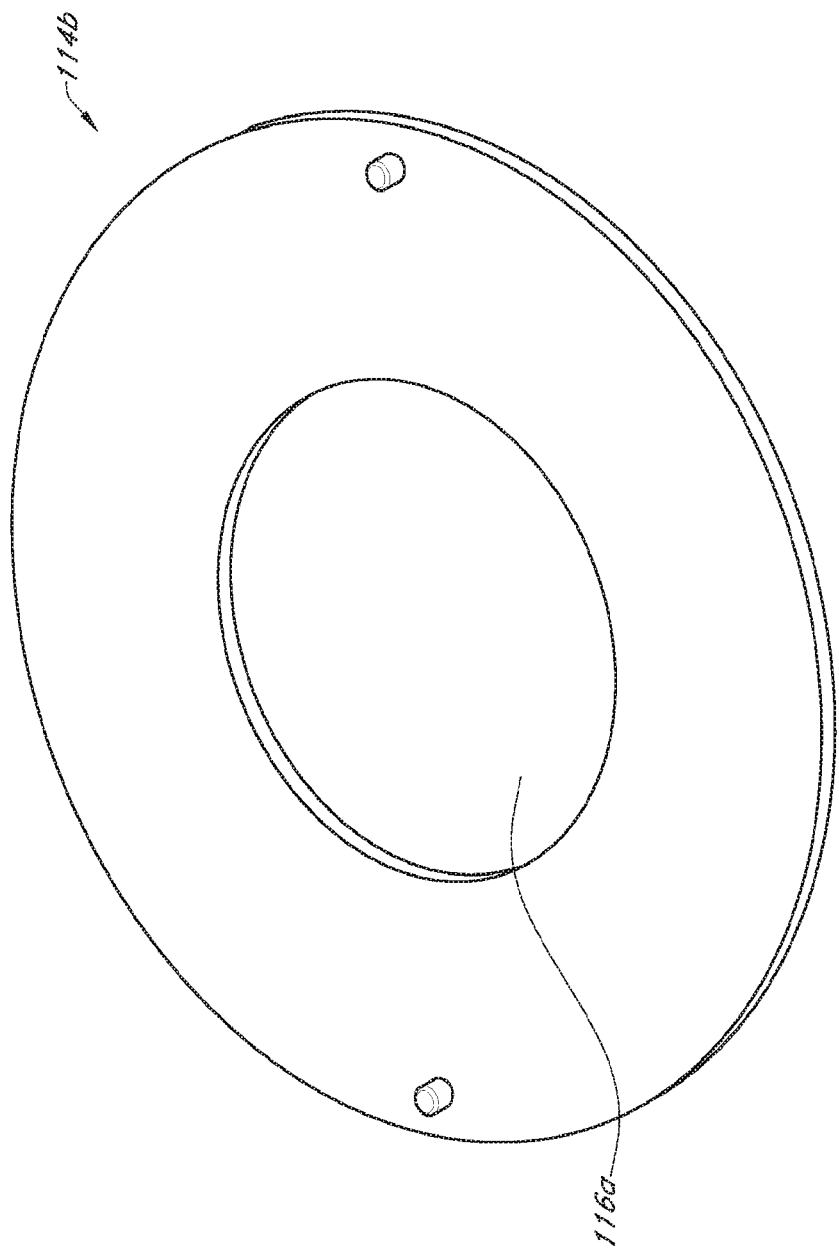
FIG. 27 is a perspective view of a Smart Candle Platform and System providing a scent top cover without hole positioned on top of the scent ring in FIG. 25.

In another aspect of the disclosed embodiment, FIG. 25 is a perspective view of a scent pan 111 of a Smart Candle Platform and System 10 as shown and disclosed herein. FIG. 26 is a perspective view of a Smart Candle Platform and System 10 providing a scent pan cover 114a with a hole (aperture 117a) positioned on top of the scent pan 111 in FIG. 25. FIG. 27 is a perspective view of a Smart Candle Platform and System 10 providing a scent pan cover 114b without a hole (or aperture 117a) positioned on top of the scent pan 111 (as shown in FIG. 25). As illustrated in FIGS. 25-27, the scent pan 111 and the scent pan cover 114 have an opening 116 wherein the size and shape of the opening 116 is large enough for the cartridge 130 to be refilled without disassembling the Smart Candle Platform and System 10. One of ordinary skill will appreciate that the opening of the scent pan 111 and the scent pan cover 114 provides a method for refilling and replacing the cartridge 130 without disassembling the Smart Candle Platform and System 10 in at least one embodiment which may be desirable to some users.

In addition, as shown in FIGS. 26 and 27, the position and the number of the holes 117a may be customized which allows the user to control the flame or the heat of the Smart Candle Platform and System 10. In addition, the position and the number of the holes 117a on the scent pan cover 114 may be customized for the purpose of decoration which may increase the attractiveness of the Smart Candle Platform and System 10 to at least some users, without any limitation and/or restriction.

Figure 28:
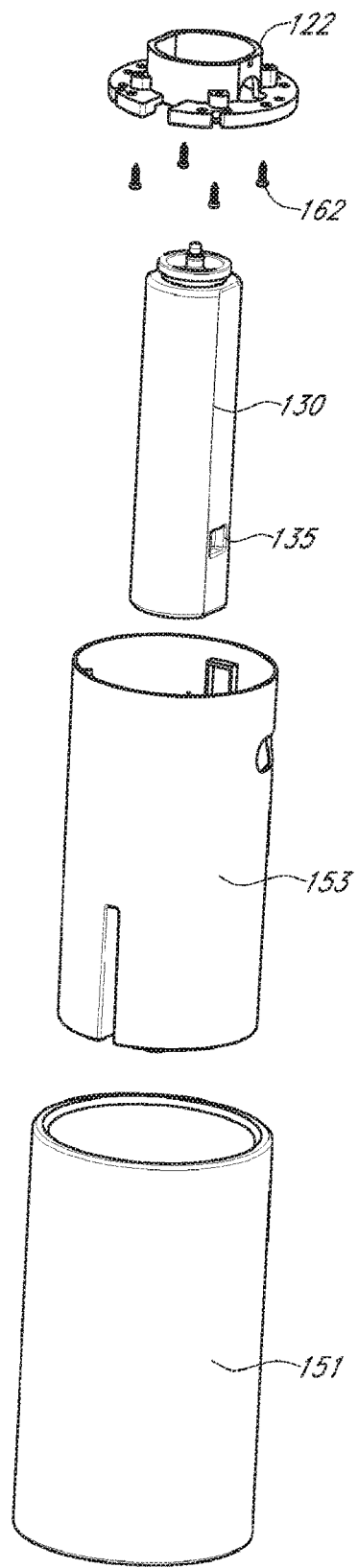
FIG. 28 is an exploded view of a Smart Candle Platform and System illustrating different layers between the interior of the Smart Candle Platform as related to the outer shell, the inner shell and the cartridge as disclosed.
Figure 29:
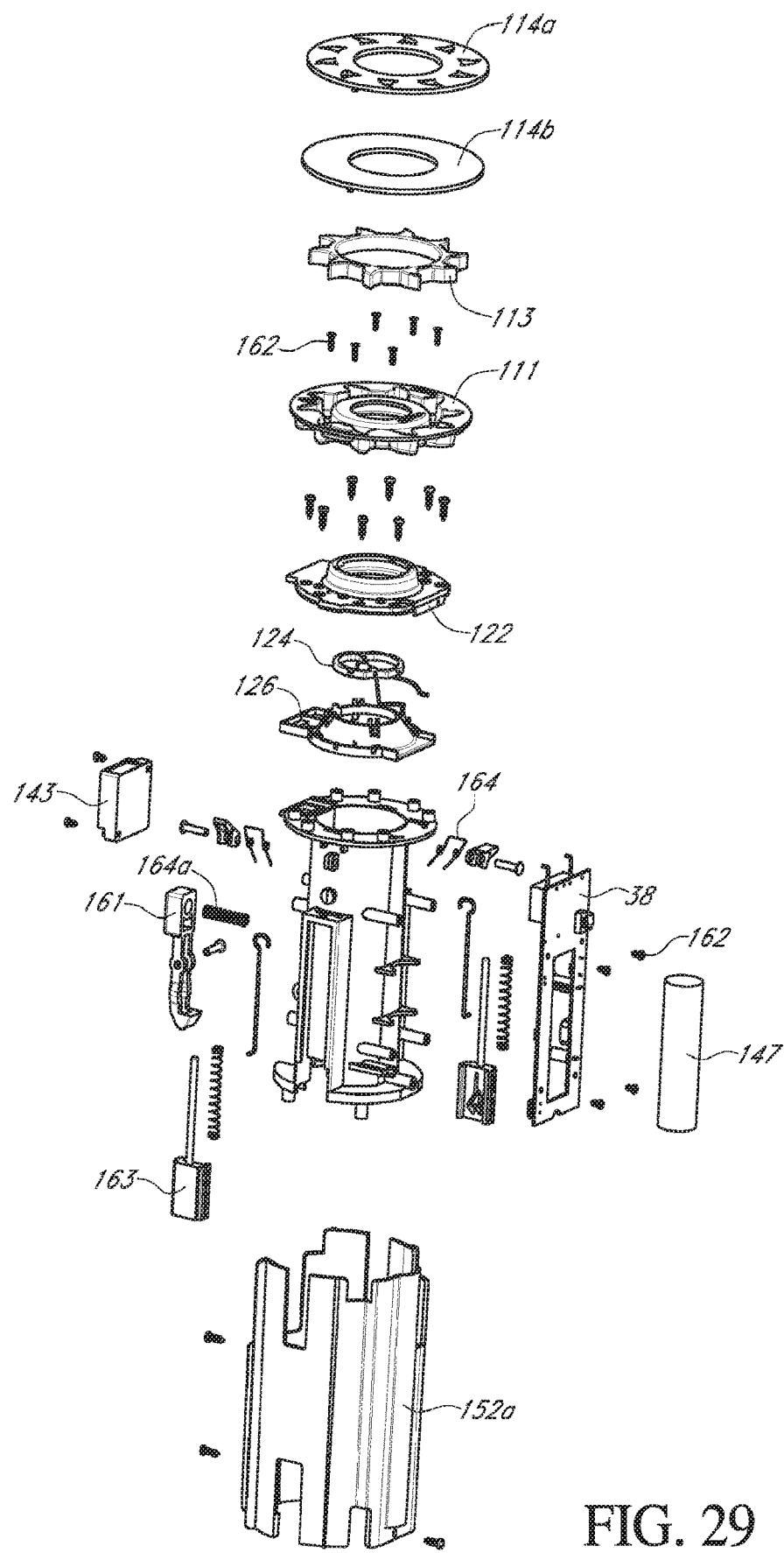
FIG. 29 is another exploded view of a Smart Candle Platform and System as related to the protective cover, support frame, push/push cam mechanism and ignitor assembly as disclosed discussed throughout.

FIG. 28 is an exploded view of a Smart Candle Platform and System 10 illustrating different layers between the interior of the Smart Candle Platform and System 10 as related to the outer shell 151, the inner cover 152 and the cartridge 130 as disclosed. FIG. 29 is another exploded view of an inner cover 152 and the top cover 110 of a Smart Candle Platform and System 10 which embodies some of the various features as disclosed as shown in FIG. 28.

Dependent on the particular application, the inner cover 152 may be constructed to be interchangeable or fixed (integral with outer shell 151) without any limitation and/or restriction. Also, dependent on the particular material and/or purpose, the shell support 152c, the protective cover 152b and the support frame 152a may be constructed together or constructed separately and conventionally attached together without any limitation and/or restriction unless otherwise indicated in the following claims.

Figure 30:
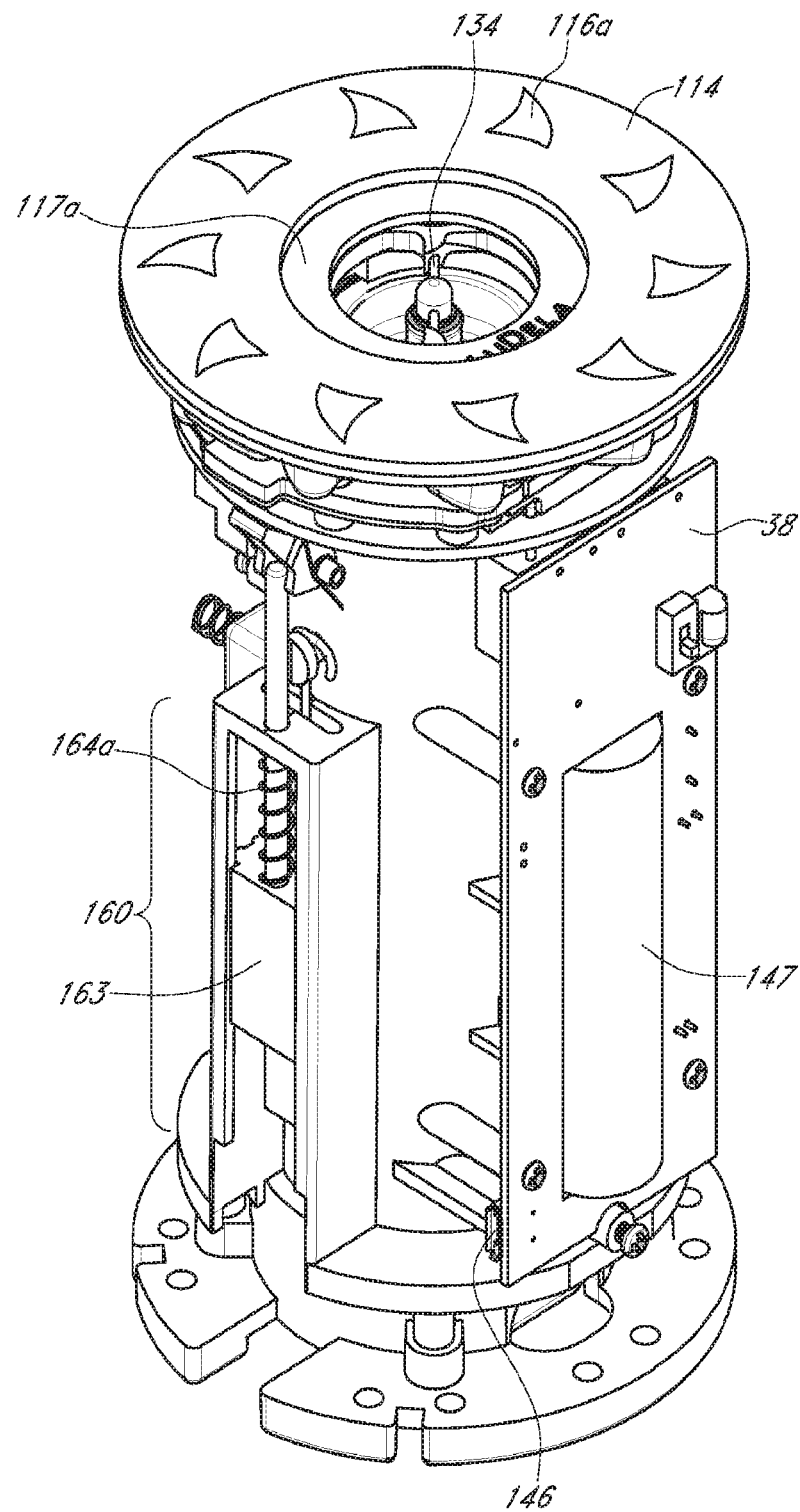
FIG. 30 is a perspective view of a Smart Candle Platform and System with the outer shell removed and a scent pan system affixed to the inner cover as shown herein.
Figure 31:
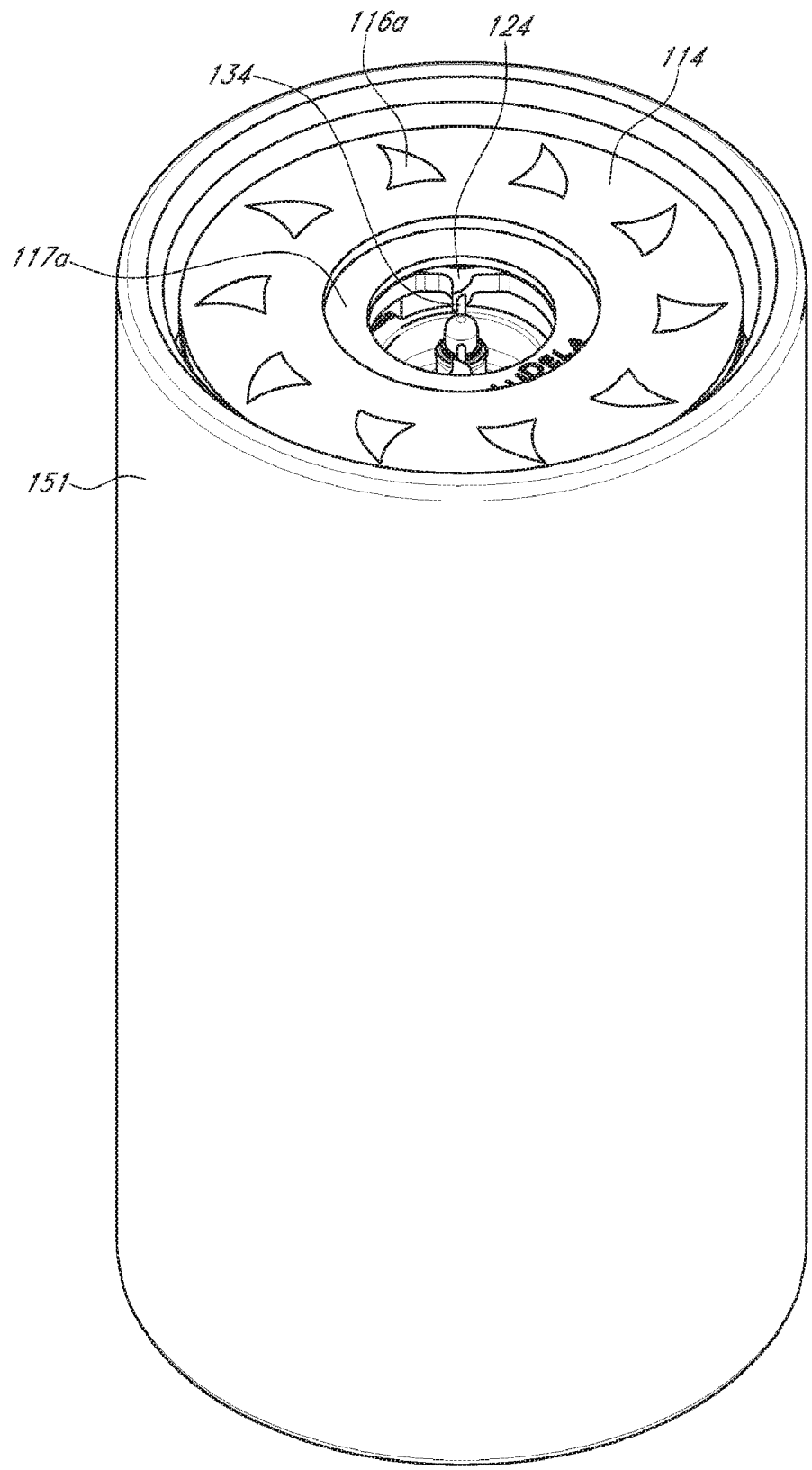
FIG. 31 is a perspective view of a Smart Candle Platform and System assembly as shown and disclosed herein.

In another embodiment, FIG. 30 is a perspective view of a Smart Candle Platform and System 10 with the outer shell 151 removed and the top cover 110 (as shown in FIGS. 25-27) affixed to the inner cover 152 as shown herein. FIG. 31 is a perspective view of a Smart Candle Platform and System 10 assembly as shown and disclosed herein. As shown and illustrated in FIGS. 30 and 31, the scent pan cover 114 has an opening 116b that allows the cartridge 130 to be refilled quickly and directly with ease. The top cover 110, the scent pan 111 and the inner cover 152 may be constructed together or constructed separately and conventionally attached together without any limitation and/or restriction.

Figure 32B:
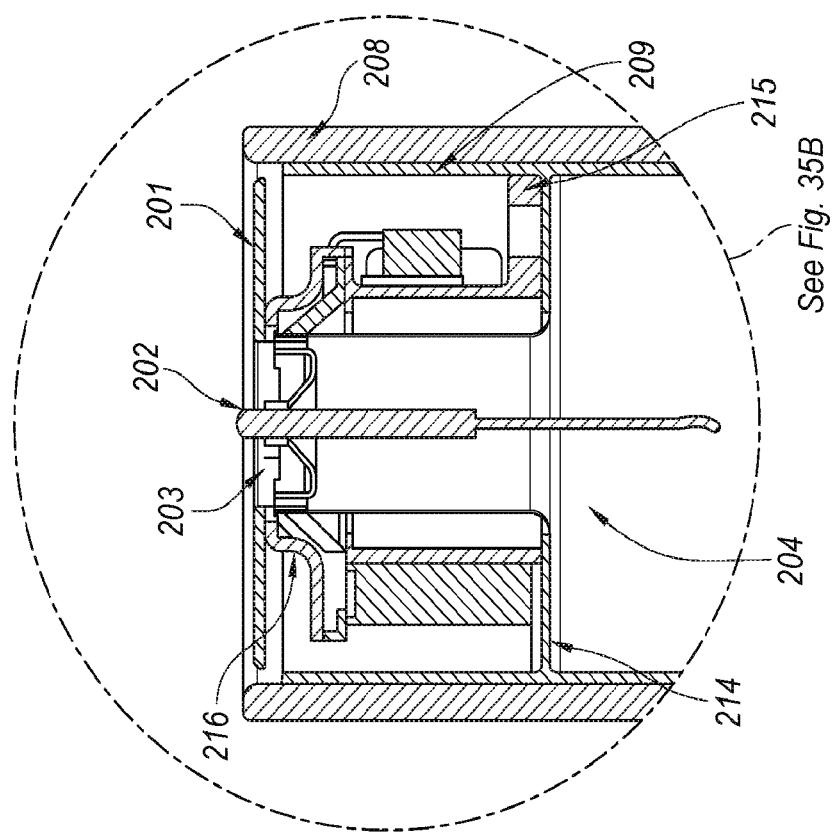
FIG. 32B is a detailed side view of the internals of the upper portion of at least one embodiment of the Smart Candle Platform and System assembly as shown and disclosed herein.
Figure 32A:
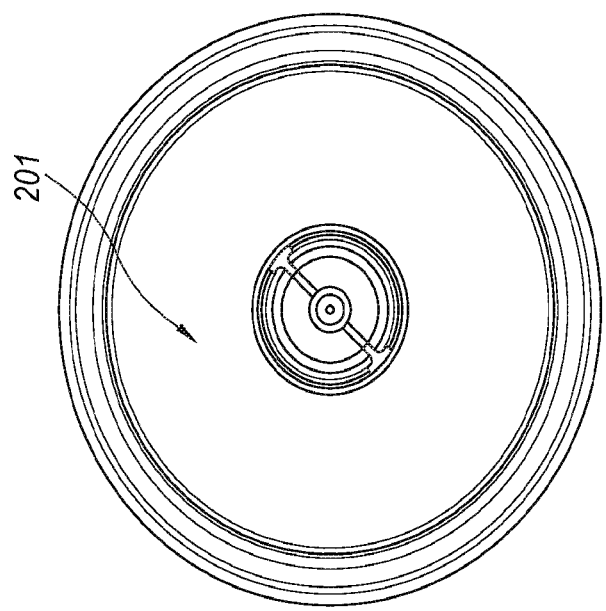
FIG. 32A is a top view of a decorative trip plate which may be used with at least one embodiment of the Smart Candle Platform and System assembly as shown and disclosed herein.

In another embodiment, FIG. 32A is a top view of a decorative trim plate 201 which may be used with at least one embodiment of the Smart Candle Platform and System assembly 10 as shown and disclosed herein. In the embodiments illustrated in FIGS. 32-38, the internal components have been re-configured to allow reduction of their footprint and allow the various control and ignition components (e.g., battery 211, charge printed circuit board (PCB) 217, extinguishing fan 206, ignition assembly 216, ignitor PCB 207, as shown in detail in FIG. 37B) to be supported using an ignitor mount 215 providing a groove or annular 218 around its mid-section and sitting on top of a support plate 214 and around a neck portion of a refill bottle fuel source, the refill bottle configured for holding a fuel (e.g., oil) and may be single-use or refillable. FIG. 32B is a detailed side view of the internals of an upper portion of at least one embodiment of the Smart Candle Platform and System assembly as shown and disclosed herein. FIG. 32B shows high performance ignitors 203, quick igniting wick 202, and decorative trim plate 201 called out in detail. As shown in FIG. 32B, the wick 202 is positioned in a fuel source 204 with an exposed portion of the wick extending from an upper end of the fuel source.

Figure 33B:
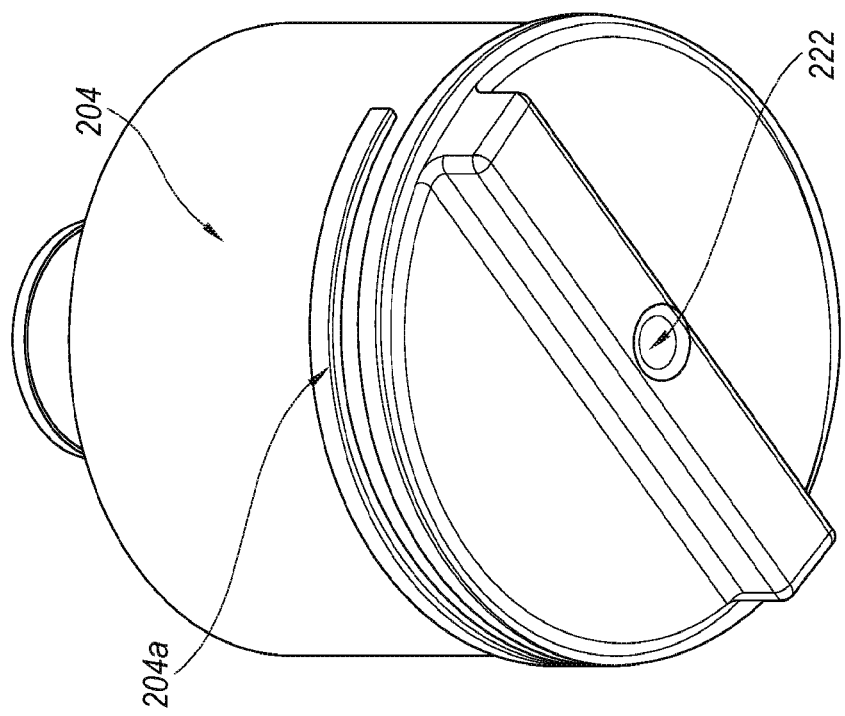
FIG. 33B is a view of the bottom of the large refill bottle of FIG. 33A configured for use with at least one embodiment of the Smart Candle Platform and System assembly as shown and disclosed herein.
Figure 33A:
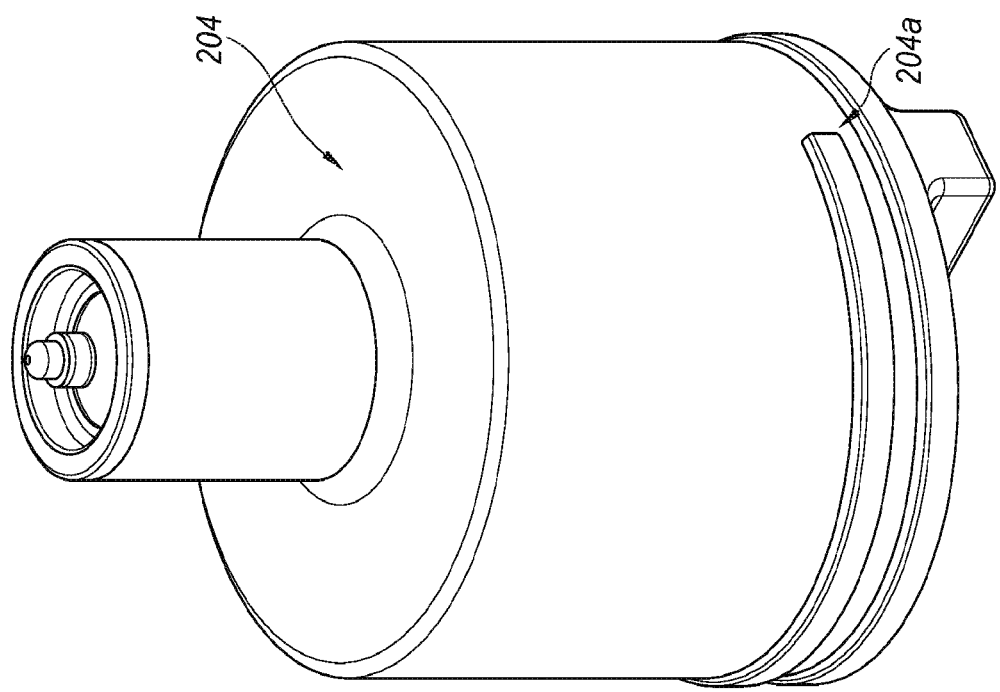
FIG. 33A is a perspective view of a large refill bottle configured for use with at least one embodiment of the Smart Candle Platform and System assembly as shown and disclosed herein.

FIG. 33A is a perspective view of the large refill bottle fuel source 204 configured for use with at least one embodiment of the Smart Candle Platform and System assembly as shown and disclosed herein. FIG. 33B is a view of a bottom of the large refill bottle 204 of FIG. 33A. FIGS. 33A and 33B illustrate that the fuel source 204 has a cylindrical shape with an upper section of the fuel source having a smaller diameter than a lower section of the fuel source. FIGS. 33A and 33B further illustrate that the fuel source 204 includes a first set of threads thereon for engagement with a corresponding second set of threads of an inner shell 209 positioned within a hollow interior of an outer shell 208 so as to allow the fuel source to be secured within a hollow inner volume of the inner shell. The hollow interior of the outer shell 208 is connecting a first opening 208a at an upper end of the outer shell and a second opening 208b at a lower end of the outer shell. FIGS. 33A and 33B also illustrate that the first set of threads includes regular right-hand threads 204a positioned on the lower section of the bottle 204 for engagement with the inner shell 209 as shown in further detail in FIG. 35B.

Figure 33D:
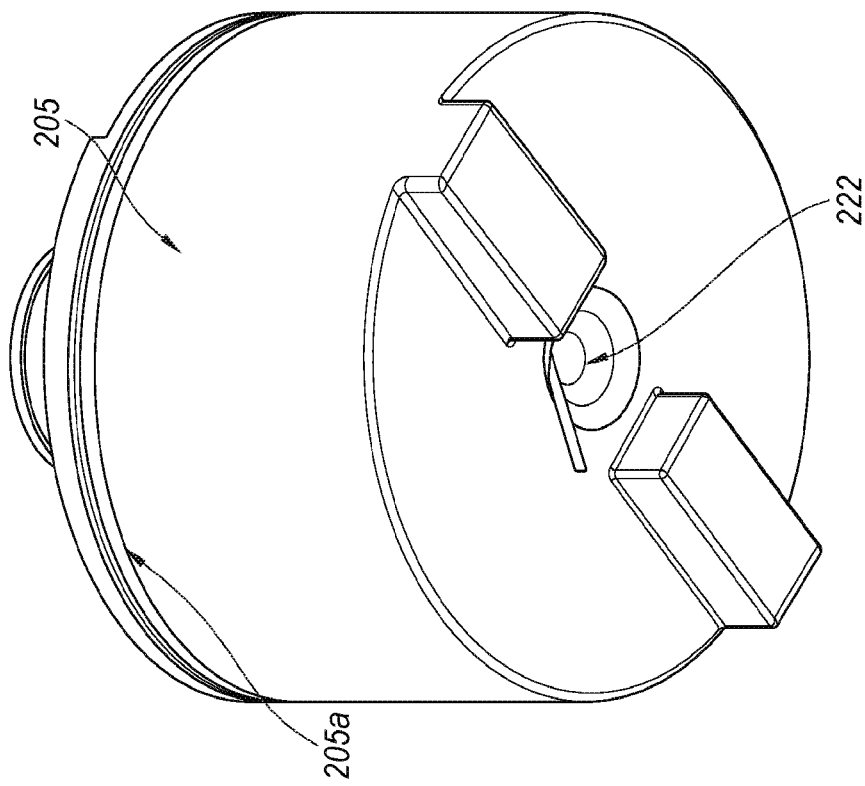
FIG. 33D is a view of the bottom of the large refill bottle having reverse threads of FIG. 33C configured for use with at least one embodiment of the Smart Candle Platform and System assembly as shown and disclosed herein.
Figure 33C:
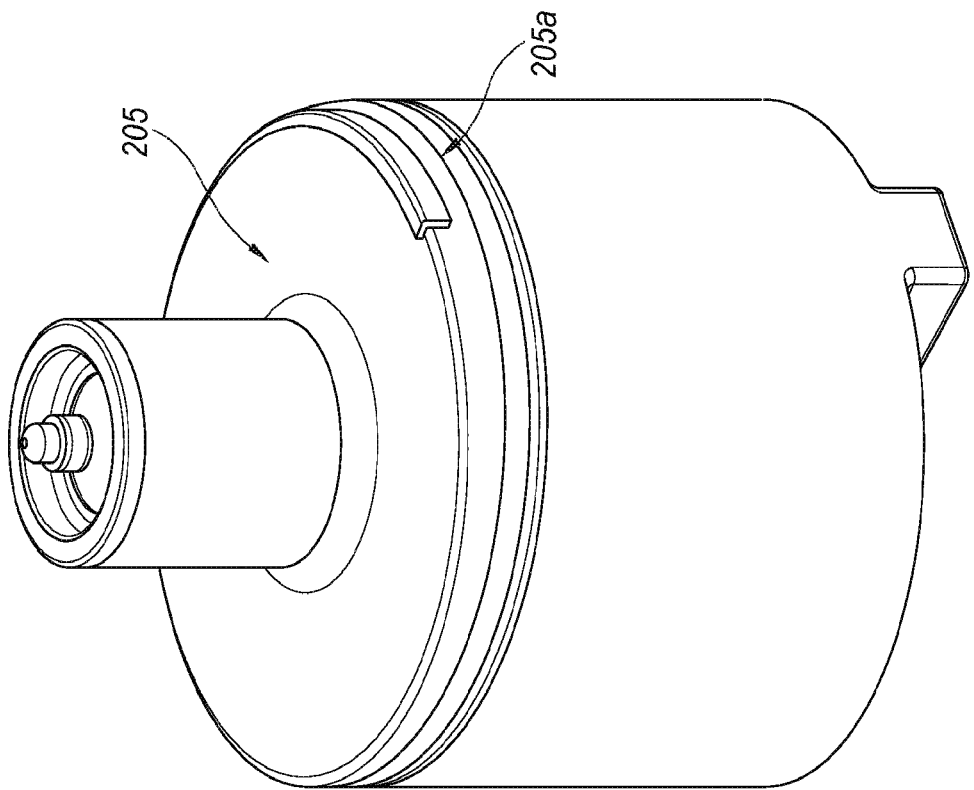
FIG. 33C is a perspective view of a large refill bottle having reverse threads configured for use with at least one embodiment of the Smart Candle Platform and System assembly as shown and disclosed herein.

FIG. 33C is a perspective view of a large refill bottle fuel source 205 configured for use with at least one embodiment of the Smart Candle Platform and System assembly as shown and disclosed herein. FIG. 33D is a view of a bottom of the large refill bottle 205 of FIG. 33C. FIGS. 33C and 33D illustrate that the fuel source 205 has a cylindrical shape with an upper section of the fuel source having a smaller diameter than a lower section of the fuel source. FIGS. 33C and 33D further illustrate that the fuel source 205 includes a first set of threads thereon for engagement with a corresponding second set of threads of the inner shell 209 so as to allow the fuel source to be secured within the hollow inner volume of the inner shell. FIGS. 33C and 33D also illustrate that the first set of threads includes reverse threads (left-hand) 205a positioned on the lower section of the bottle 205 for engagement with the inner shell 209 as shown in further detail in FIGS. 35C-35D.

One of ordinary skill will appreciate that either the configuration as disclosed in FIGS. 33A and 33B or the configuration as disclosed in FIGS. 33C and 33D may be used without restriction or limitation and may be suitable for any particular application. At least one advantage of a threaded large volume refill bottle fuel source (e.g., 204 or 205) is that the threaded version of the bottle reduces the potential for incorrect insertion by users. One of ordinary skill will appreciate that the lower section or the bottom of the bottle may or may not be configured with a space 222 located, e.g., in the middle of the bottle's bottom and configured to accept a pillar candle spike.

Figure 34:
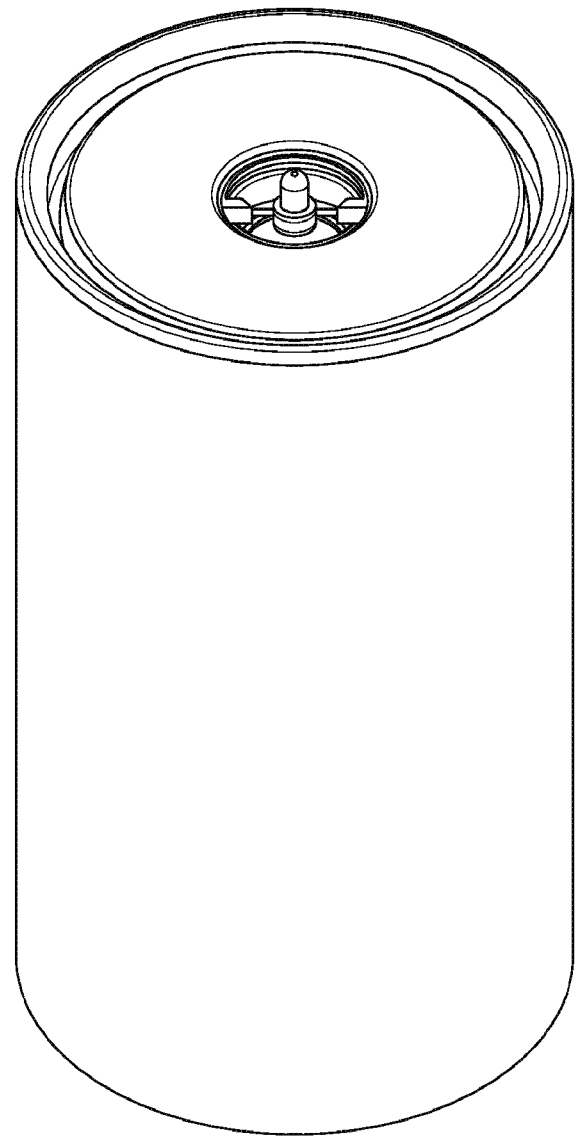
FIG. 34 is a perspective view of an embodiment of the Smart Candle Platform and System assembly as shown and disclosed herein in FIGS. 33-36.

FIG. 34 is a perspective view of an embodiment of the Smart Candle Platform and System assembly as shown and disclosed herein in FIGS. 32-38. FIG. 35A is a side view of the embodiment of the Smart Candle Platform and System assembly shown in FIG. 34 using a large volume refill bottle fuel source with regular threads. FIG. 35B is a cut-away side view of the embodiment of the Smart Candle Platform and System assembly shown in FIG. 35A.

Figure 35B:
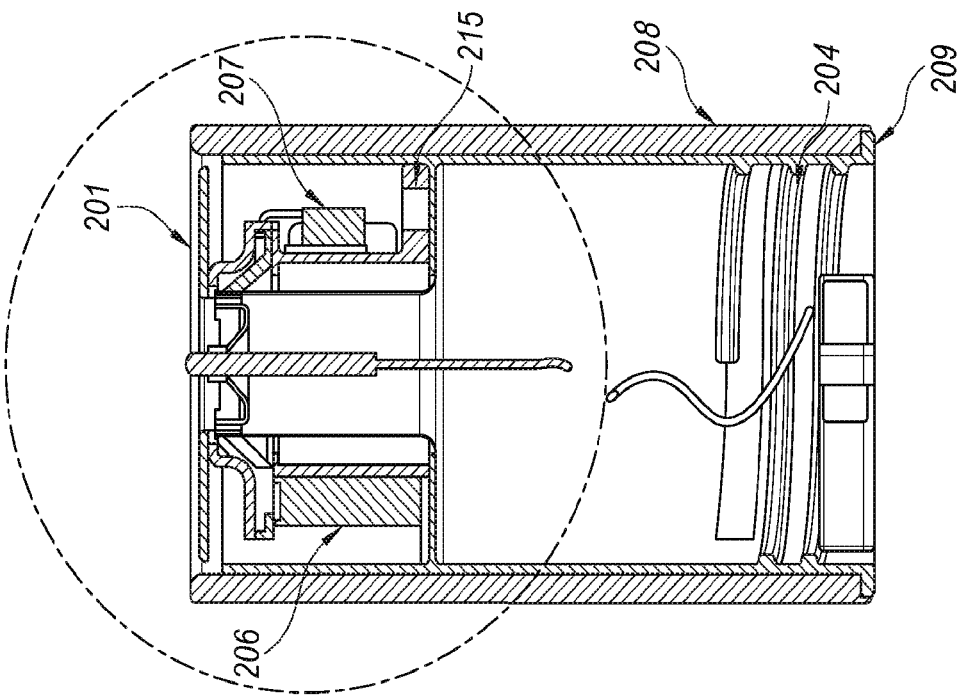
FIG. 35B is a cut-away side view of the embodiment of the Smart Candle Platform and System assembly as shown and disclosed herein in FIG. 35A.
Figure 35A:
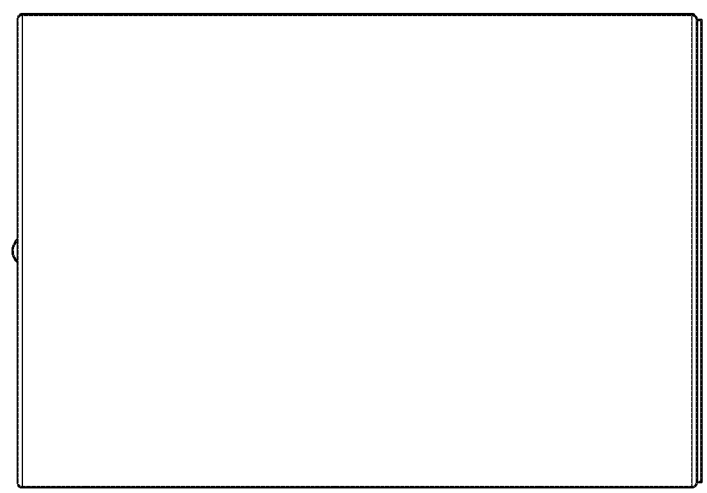
FIG. 35A is a side view of the embodiment of the Smart Candle Platform and System assembly as shown and disclosed herein in FIGS. 33-36 using a large volume re-fill with regular threads.
Figure 35D:
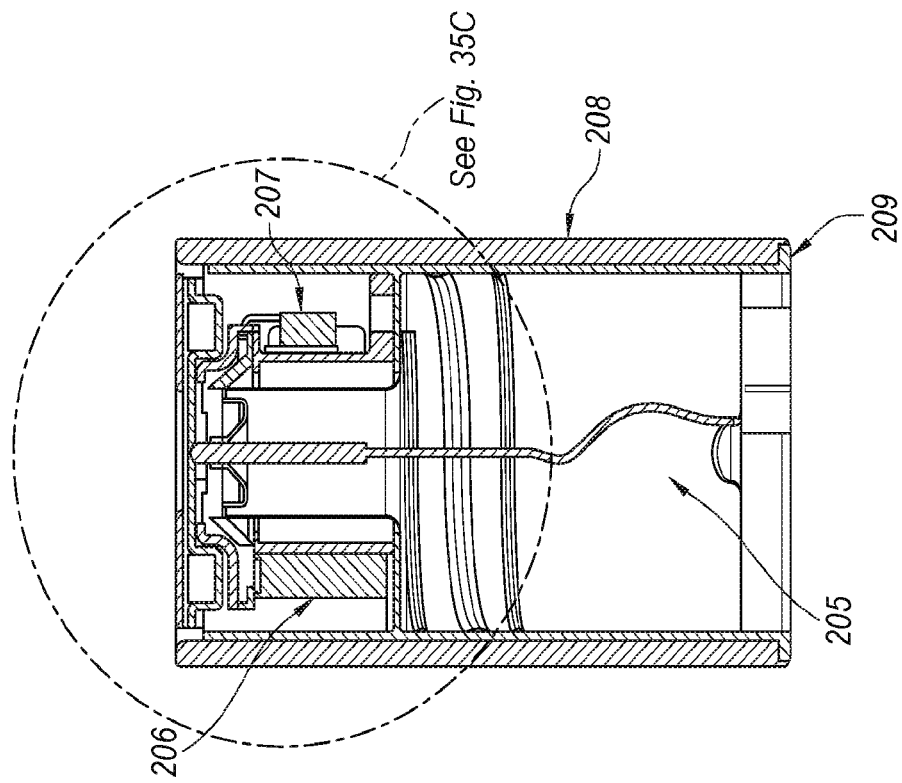
FIG. 35D is a cut-away side view of the embodiment of the Smart Candle Platform and System assembly as shown and disclosed herein in FIG. 35C as configured for use with the large volume refill having reverse threads as disclosed in FIGS. 33C and 33D.
Figure 35C:
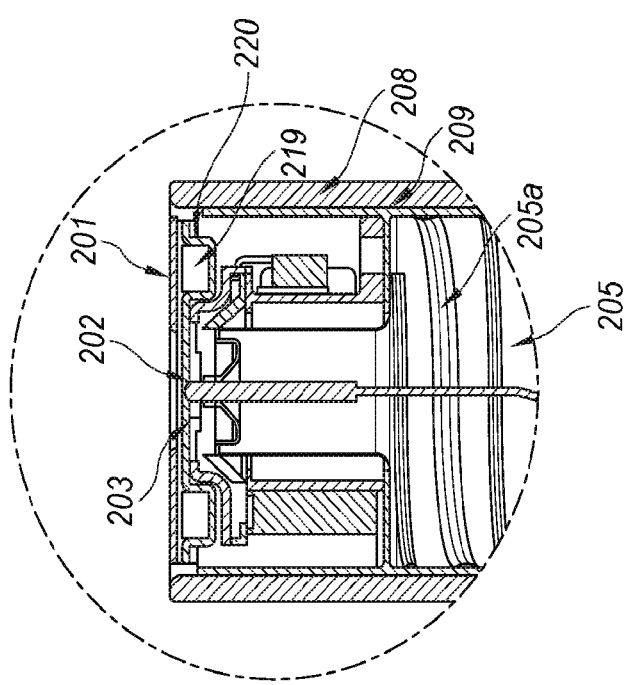
FIG. 35C is a detailed side view of the internals of the upper portion of at least one embodiment of the Smart Candle Platform and System assembly as shown and disclosed herein when the large volume re-fill is configured with reverse threads.

FIG. 35C is a detailed side view of the internals of an upper portion of at least one embodiment of the Smart Candle Platform and System assembly as shown and disclosed herein when the large volume refill bottle 205 is configured with reverse threads 205a positioned on the lower section of the bottle 205 for engagement with the inner shell 209. FIG. 35C shows the high performance ignitors 203, the quick igniting wick 202, and the decorative trim plate 201 called out in detail. As shown in FIG. 35C, the wick 202 is positioned in the fuel source 205 with an exposed portion of the wick extending from an upper end of the fuel source. FIG. 35D is a cut-away side view of the embodiment of the Smart Candle Platform and System assembly as shown and disclosed herein in FIG. 35C as configured for use with the large volume refill bottle 205 having reverse threads 205a as disclosed in FIGS. 33C and 33D with the extinguishing fan 206 and ignitor PCB 207 called out. The outer shell 208 the Smart Candle Platform and System assembly can be made of wax but is not so limited and may be constructed from other materials, similar to the inner shell 209.

FIG. 36A is a perspective view of the embodiment of the Smart Candle Platform and System assembly as shown and disclosed herein in FIGS. 32-38 with a clear shell to show the position of the internals including the control PCBs 210 as called out. FIG. 36B is a cut-away top view of the embodiment of the Smart Candle Platform and System assembly shown in FIG. 36A. As disclosed, an on-off switch (not shown) may be positioned proximate to the upper portion of the System near a top charging port. The arrangement disclosed allows a Universal Serial Bus (USB) charging port 212 to be incorporated along with a large capacity battery 211, as shown, to improve usability. USB port 212 can be configured to provide power to the Smart Candle Platform and System assembly and/or to charge the battery 211. At least one magnet 213 can be positioned in the interior of the ignition assembly 216 for retention of the trim plate 201. As shown in FIG. 36B, four (4) magnets 213 are positioned in the interior of the ignition assembly 216 for retention of the trim plate 201.

Figure 37A:
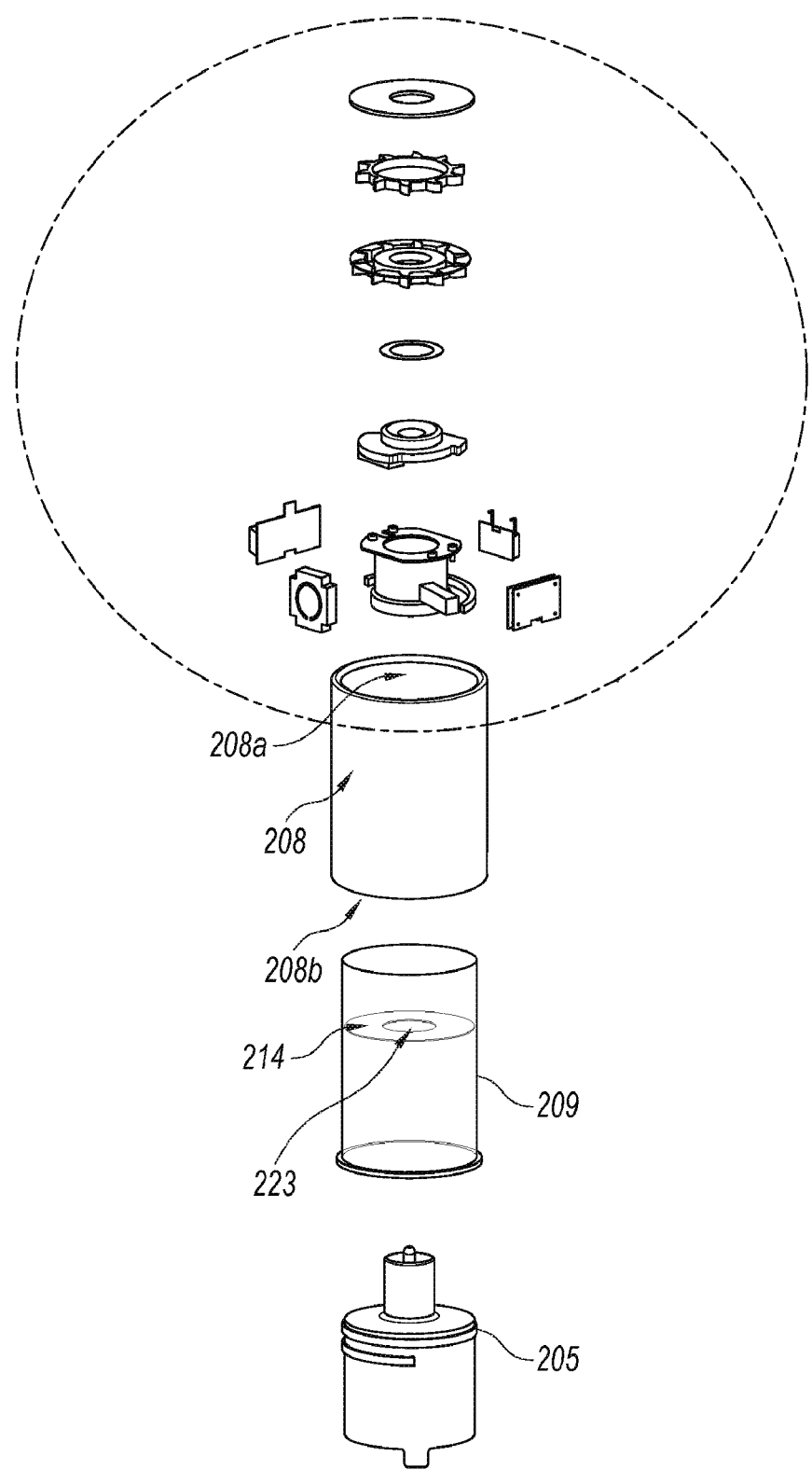
FIG. 37A is an exploded view of the embodiment of the Smart Candle Platform and System disclosed in FIGS. 32-36 as related to the entire assembly and particularly with a large volume refill having reverse threads.
Figure 37B:
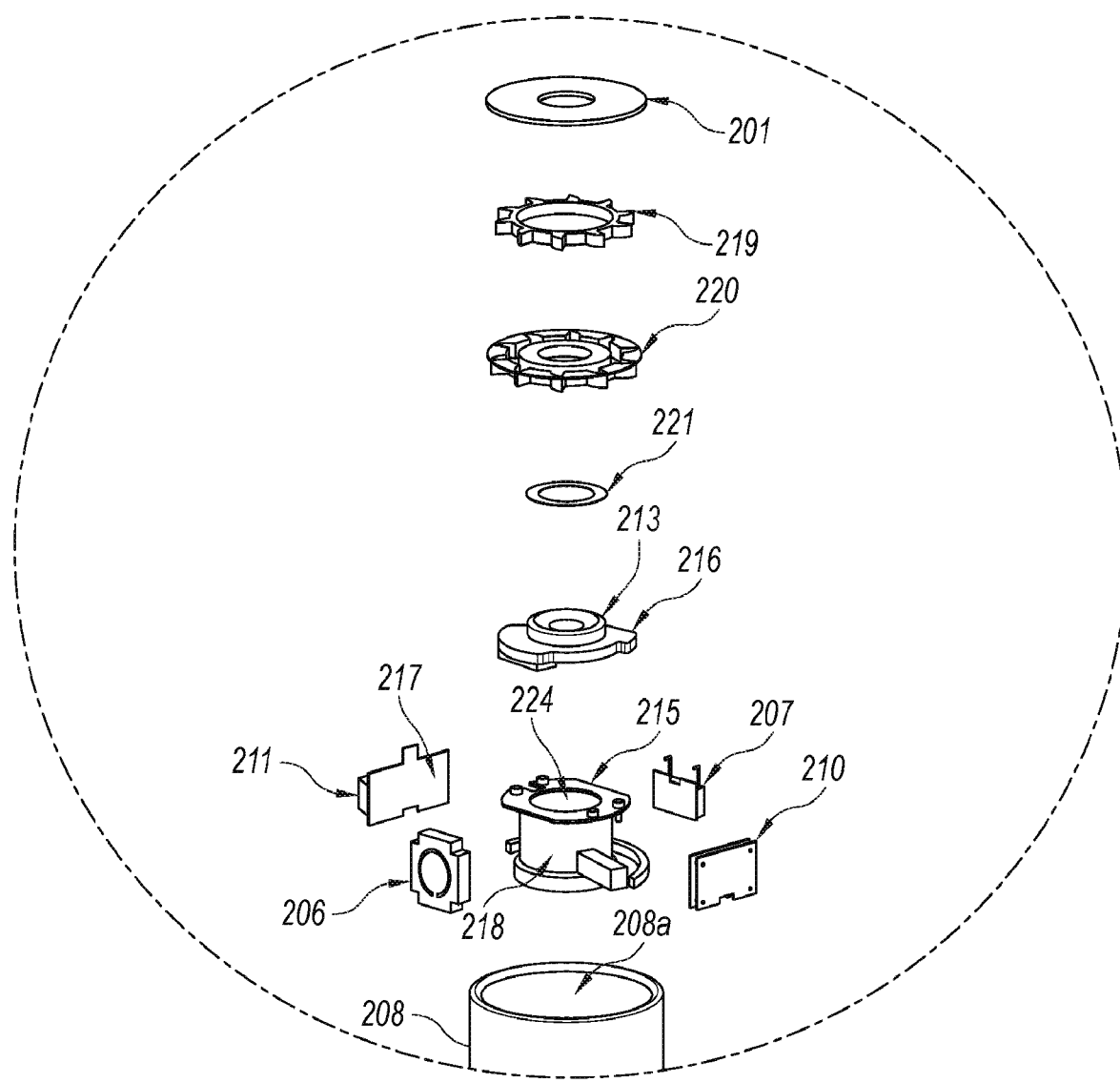
FIG. 37B is a detailed view of FIG. 37A as related to the ignition system and control systems which may be mounted in the upper portion of the inner support shell and above the refill bottle which is shown as large volume refill having reverse threads.

FIG. 37A is an exploded view of the embodiment of the Smart Candle Platform and System disclosed in FIGS. 32-38 as related to the entire assembly and particularly with the large volume refill bottle 205 having reverse threads. FIG. 37B is a detailed view of FIG. 37A as related to the ignition system and control systems which may be mounted in an upper portion of the inner support shell and above the refill bottle fuel source which is shown as large volume refill bottle 205 having reverse threads in FIG. 37A. The ignition assembly can be positioned within the hollow inner volume of the inner shell 209 proximate to the first opening 208a of the outer shell 208. The ignition assembly can be positioned between the ignitor mount 215 and the first opening 208a of the outer shell 208. As shown in FIG. 37B, the ignition assembly can be positioned underneath the decorative trim plate 201. As shown in FIG. 37B, the decorative trim plate 201 rests above a removable scent ring 219 which may be positioned in an optional scent pan 220 positioned between the trim plate 201 and the ignition assembly 216. A steel ring 221 for the scent pan retention may be positioned underneath the scent pan 220 and in the interior of the ignition assembly 216 having four (4) locating magnets 213 positioned therein. The ignition assembly 216 rests upon and engages with the ignitor mount 215 having the groove 218 in its mid-section in which the battery 211 and charge PCB 217 may be positioned along with the control components including the extinguishing fan 206, control PCBs 210 an/or ignitor PCB 207. The ignition assembly 216 can be coupled to an ignition control system (e.g., ignitor PCB 207 and/or control PCBs 210) which is electronically controlled. The ignitor mount 215 and control components are then positioned within the hollow inner volume of the inner shell 209 to rest upon the support plate 214 positioned within the hollow inner volume of the inner shell and having a hollow channel through a mid-section thereof and/or a threaded refill bottle (e.g., 204 or 205). The outer shell 208 is then slidably extended over the inner shell 209 to form one embodiment of the Smart Candle Platform in which the ignitor mount is positioned between the support plate 214 and the first opening 208a of the outer shell 208.

Figure 38:
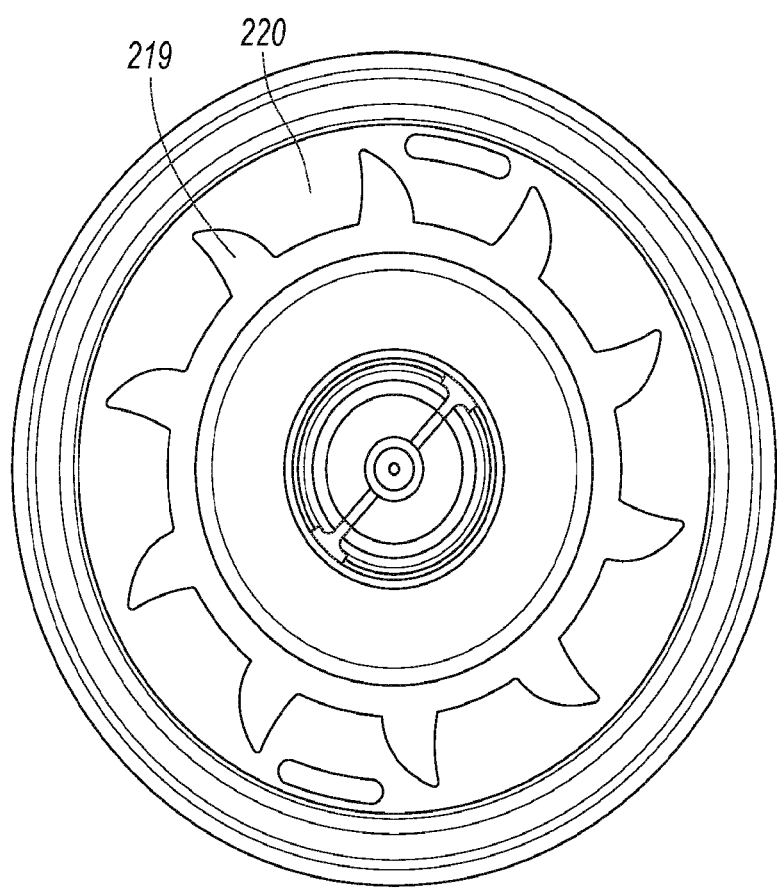
FIG. 38 is another embodiment of the scent pan configured for use with at least one embodiment of the Smart Candle Platform and System as disclosed herein.

FIG. 38 is another embodiment of the optional scent pan 220 configured for use with at least one embodiment of the Smart Candle Platform and System as disclosed herein wherein the scent pan 220 is removable and the scent ring 219 is interchangeable. The scent pan 220 as shown in FIGS. 36 and 38 may be constructed from steel and configured to engage with magnets 213.

The Smart Candle Platform and System assembly as shown and disclosed herein in FIGS. 32-38 may comprise at least one sensor, wherein the at least one sensor is coupled to a control system (e.g., control PCBs 210) which is electronically controlled. The at least one sensor may comprise a continuity sensor, an accelerometer, a gyroscope, a proximity sensor (which can be a magnetic based proximity sensor, or a visual based proximity sensor), a fuel level sensor, a flame sensor, an infrared (IR) sensor, or a thermopile sensor, among others. The control system may comprise an on/off switch, an ignition control system, an extinguisher system, an infrared (IR) remote control system, a timer, a fuel control system, a fuel feed control system, a fuel storage control system, or a fuel level control system, among others. The at least one sensor and/or the control system can be located in the groove 218 of the ignitor mount 215 along with the extinguishing fan 206. The Smart Candle Platform and System assembly can further comprise a thermo-electric charging system installed alone or in combination with a battery and configured to produce electrical current using heat produced by a burning fuel.

One of ordinary skill will appreciate that other configurations allowing single or multiple ignitors may be selected for any particular application without departure from the spirit and intent of the present disclosure. One of ordinary skill appreciate that other types of methods of flame sensing/monitoring including pyrometers may be used with Smart Candle Platform 10 as disclosed herein without departure from spirit and intent of the disclosure.

Having described the preferred embodiments, other features of the Smart Candle Platform will undoubtedly occur to those versed in the art, as will numerous modifications and alterations in the embodiments as illustrated herein, all of which may be achieved without departing from the spirit and scope of the Smart Candle Platform disclosed herein. Accordingly, the methods and embodiments pictured and described herein are for illustrative purposes only, and the scope of the present disclosure extends to all method and/or structures for providing increased functionality, comfort, longevity, enjoyment and aesthetics in the use and access of Smart Candle Platforms and aesthetic controllable natural lighting systems. Furthermore, the methods and embodiments pictured and described herein are no way limiting to the scope of the Smart Candle Platform and method of use unless so stated in the following claims.

It should be noted that the Smart Candle Platform is not limited to the specific embodiments pictured and described herein, but is intended to apply to all similar apparatuses and methods for providing the various benefits and/or features of a Smart Candle Platform. Modifications and alterations from the described embodiments will occur to those skilled in the art without departure from the spirit and scope of the Smart Candle Platform. It is understood that the Smart Candle Platform as disclosed herein extends to all alternative combinations of one or more of the individual features mentioned, evident from the text and/or drawings, and/or inherently disclosed. All of these different combinations constitute various alternative aspects of the Smart Candle Platform and/or components thereof. The embodiments described herein explain the best modes known for practicing the Smart Candle Platform and/or components thereof and will enable others skilled in the art to utilize the same. The claims are to be construed to include alternative embodiments to the extent permitted by the prior art.

While the Smart Candle Platform has been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. It will be apparent to those skilled in the art that various modifications and variations can be made without departing from the scope or spirit. Other embodiments will be apparent to those skilled in the art from consideration of the specification and practice disclosed herein. It is intended that the specification and examples be considered as illustrative only, with a true scope and spirit being indicated by the following claims.

I claim:

1. A living flame candle platform comprising:
   an outer shell having a hollow interior connecting a first opening at an upper end of the outer shell and a second opening at a lower end of the outer shell;
   an inner shell positioned within the hollow interior of the outer shell and having a hollow inner volume;
   a support plate positioned within the hollow inner volume of the inner shell, the support plate having a hollow channel through a mid-section thereof;
   an ignition assembly positioned within the hollow inner volume of the inner shell; and
   a fuel source positioned within the hollow inner volume of the inner shell, the fuel source having a cylindrical shape, wherein an upper section of the fuel source has a smaller diameter than a lower section of the fuel source such that the upper section of the fuel source extends towards the first opening through the hollow channel of the support plate, the fuel source further including a first set of threads thereon for repeatable engagement with a corresponding second set of threads of the inner shell so as to allow the fuel source to be removably secured within the hollow inner volume of the inner shell.

2. The living flame candle platform according to claim 1, wherein the first set of threads is located on the lower section of the fuel source.

3. The living flame candle platform according to claim 1, comprising an ignitor mount positioned within the hollow inner volume of the inner shell, the ignitor mount having a second hollow channel through the ignitor mount that corresponds to the hollow channel of the support plate, and a side wall around the second hollow channel through the ignitor mount, wherein the side wall has a groove around the second hollow channel through the ignitor mount.

4. The living flame candle platform according to claim 3, wherein the ignitor mount is positioned between the support plate and the first opening of the outer shell.

5. The living flame candle platform according to claim 4, wherein the ignition assembly is positioned between the ignitor mount and the first opening of the outer shell.

6. The living flame candle platform according to claim 1, wherein the ignition assembly is positioned underneath a trim plate.

7. The living flame candle platform according to claim 6, wherein the trim plate has an aperture, and the trim plate is positioned in the hollow interior of the outer shell proximate to the upper end of the outer shell.

8. The living flame candle platform according to claim 6, including a scent pan that is positioned between the trim plate and the ignition assembly.

9. The living flame candle platform according to claim 8, including a scent ring that is positioned in the scent pan.

10. The living flame candle platform according to claim 1, including a wick that is positioned in the fuel source with an exposed portion of the wick extending from an upper end of the fuel source.

11. The living flame candle platform according to claim 1, wherein the ignition assembly is coupled to an ignition control system which is electronically controlled.

12. The living flame candle platform according to claim 1, comprising at least one sensor, wherein the at least one sensor is coupled to a control system which is electronically controlled.

13. The living flame candle platform according to claim 12, wherein the at least one sensor comprises a continuity sensor, an accelerometer, a gyroscope, a proximity sensor, a fuel level sensor, a flame sensor, an infrared (IR) sensor, or a thermopile sensor.

14. The living flame candle platform according to claim 13, wherein the proximity sensor comprises a magnetic based proximity sensor, or a visual based proximity sensor.

15. The living flame candle platform according to claim 12, wherein the control system comprises an on/off switch, an ignition control system, an extinguisher system, an infrared (IR) remote control system, a timer, a fuel control system, a fuel feed control system, a fuel storage control system, or a fuel level control system.

16. The living flame candle platform according to claim 1, comprising a Universal Serial Bus (USB) port configured to provide power to the living flame candle platform and/or to charge a battery.

17. The living flame candle platform according to claim 12, wherein the at least one sensor, or the control system, or an extinguishing fan is located in a groove of an ignitor mount.

18. The living flame candle platform according to claim 6, wherein the ignition assembly comprises at least one magnet for retention of the trim plate.

19. The living flame candle platform according to claim 1, wherein the lower section of the fuel source is configured with a space configured to accept a pillar candle spike.

20. The living flame candle platform according to claim 1, comprising a thermo-electric charging system installed alone or in combination with a battery and configured to produce electrical current using heat produced by a burning fuel.

* * * * *